(12) United States Patent
Ronco et al.

(10) Patent No.: US 9,290,750 B2
(45) Date of Patent: *Mar. 22, 2016

(54) 7,11-METHANOCYCLOOCTA [B] QUINOLINE DERIVATIVE AS HIGHLY FUNCTIONALIZABLE ACETYLCHOLINESTERASE INHIBITORS

(71) Applicant: UNIVERSITE DE ROUEN, Mont-Saint-Aignan (FR)

(72) Inventors: Cyril Ronco, Jena (DE); Pierre Yves Renard, Paris (FR); Ludovic Jean, Rouen (FR); Florian Nachon, Saint Martin D'heres (FR); Anthony Romieu, Rouen (FR)

(73) Assignee: UNIVERSITE DE ROUEN, Mont-Saint-Aignan (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/669,160

(22) Filed: Mar. 26, 2015

(65) Prior Publication Data

US 2015/0197735 A1    Jul. 16, 2015

Related U.S. Application Data

(62) Division of application No. 13/640,182, filed as application No. PCT/EP2011/055565 on Apr. 8, 2011, now Pat. No. 9,040,506.

(60) Provisional application No. 61/322,348, filed on Apr. 9, 2010.

(30) Foreign Application Priority Data

Apr. 9, 2010 (EP) .................... 10305366

(51) Int. Cl.
    *C07D 221/22* (2006.01)
    *C12N 9/18* (2006.01)
    *C07D 401/08* (2006.01)
    *C07D 401/14* (2006.01)

(52) U.S. Cl.
CPC ............... *C12N 9/18* (2013.01); *C07D 221/22* (2013.01); *C07D 401/08* (2013.01); *C07D 401/14* (2013.01); *C12Y 301/01008* (2013.01)

(58) Field of Classification Search
CPC ...................................... C07D 221/22
See application file for complete search history.

(56) References Cited

U.S. PATENT DOCUMENTS 5,965,569 A    10/1999    Camps Garcia et al.

FOREIGN PATENT DOCUMENTS

EP    0 796 849 A1    9/1997
WO    97/13754    4/1997

OTHER PUBLICATIONS

Pelayo Camps et al. "Synthesis, in vitro pharmacology, and molecular modeling of very potent tacrine—huperzine A hybrids as acetylcholinesterase inhibitors of potential interest for the treatment of Alzheimer's disease", Journal of Medicinal Chemistry, American Chemical Society, Washington, US, vol. 42, n° 17, Aug. 26, 1999, p. 3227-3242.

Ronco Cyril et al. "Synthesis and structure-activity relationship of huprine derivatives as human acetylcholinesterase inhibitors", Bioorganic & Medicinal Chemistry, Pergamon, GB, vol. 17, n° 13, Jul. 1, 2009, p. 4523-4536.

*Primary Examiner* — Wu-Cheng Winston Shen
*Assistant Examiner* — Christopher R Stone
(74) *Attorney, Agent, or Firm* — Young & Thompson

(57) ABSTRACT

New highly functionalizable Huprine derivatives of formula I:

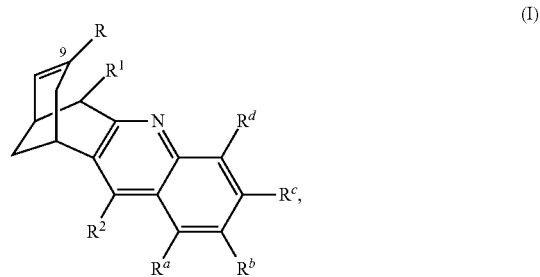

and a method for preparing such compounds and their use for treating neurological diseases in which the level of acetylcholine is affected such as Alzheimer's disease.

19 Claims, No Drawings

7,11-METHANOCYCLOOCTA [B] QUINOLINE DERIVATIVE AS HIGHLY FUNCTIONALIZABLE ACETYLCHOLINESTERASE INHIBITORS

The present invention concerns new highly functionalizable Huprine derivatives and a method for preparing such compounds. Huprine derivatives are acetylcholinesterase inhibitors and, for this reason, are promising candidates for treating neurological diseases in which the level of acetylcholine is affected such as Alzheimer's disease.

Alzheimer's disease is nowadays a main public health subject having economic and human impact which is intended to grow with the ageing of the population. Among the different solutions investigated for treating neurodegenerative diseases, and especially Alzheimer's disease, the only treatment resulting in efficient compounds which are currently commercialized is a symptomatic treatment of the cholinergic deficiencies: acetylcholinesterase (AchE), the key enzyme ending the process of nerve impulse transmission, is inhibited by continuously administrating reversible acetylcholinesterase inhibitors. Currently, the four compounds approved by international regulatory organizations regarding public health are Tacrine (Cognex®), Donepezil (E2020, Aricept®), Rivastigmine (Exlon®) and Galanthamine (Reminyl®). However, those compounds and their derivatives have low liposolubility and thus do not easily cross the blood-brain barrier. Furthermore, besides the fact that the treatment is assumed to be a life-time treatment and that it involves non negligible side effects, those compounds do not exhibit a sufficiently high affinity to the AChE. Therefore, the need remain for alternative new compounds having a higher efficiency than Donepezil which is the reference among currently commercialized and able to cross the blood-brain barrier. Moreover, prodrugs delivering the active compound only when the target is reached, would allow decreasing the toxicity of such life-time treatment.

At the end of the 90s, Camps et al. discovered new hybrid compounds of Tacrine and Huperzine, named Huprines, which are the most efficient monomeric inhibitors of AChE currently known (Huprines X and Y have an $IC_{50}$ around 1 nM). However, those compounds still exhibit rendering hepatic toxicity and decreasing the effective amount needed for the treatment is essential. The Huprines derivatives described in WO 97/13754 present some possibilities for structural arrangement but the functionalization of those compounds is limited. Therefore, the need of highly functionalizable Huprine derivatives remains to adapt the desired pharmacologic properties.

The inventors have now found a new process for preparing Huprine derivatives. This process is fast, efficient and allows introducing an ester function on position 9 which is easily modified into various functions through additional reaction steps.

In the present invention, the term "pharmaceutically acceptable salts" refer to salts which are not deleterious to the patient and compatible with a use in a pharmaceutical composition. Pharmaceutically acceptable salts of the compounds of the invention include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine, 2-(diethylamino)ethanol, ethanolamine, morpholine, 4-(2-hydroxyethyl)morpholine and zinc salts. Hemisalts of acids and bases may also be formed, for example, hemisulphate and hemicalcium salts. Preferred, pharmaceutically acceptable salts include hydrochloride/chloride, hydrobromide/bromide, bisulphate/sulphate, nitrate, citrate, and acetate.

In the present invention, the term "prodrug" refers to any compound which is a metabolic precursor of the compounds of the invention. It includes any compound transformable to deliver an effective amount of a pharmaceutically active compound of the invention said transformation can be chemical, enzymatic or any other transformation resulting in the in vivo delivery of the compound of the invention. A prodrug can be an inactive compound when administrated to the patient. The prodrugs of the compounds of the invention can be easily determined by the skilled person in the art.

In the present invention the term "neurological condition" refers to a group of disorders that involve any part of the nervous system resulting from damage to the brain, spinal column or nervous system caused by illness or injury. In particular, neurological conditions include Alzheimer's disease, multiple sclerosis, cognitive disorders, memory disorder, depressive disorders, bipolar disorder and schizophrenic disorders, Parkinson's' disease, Huntington's disease, vascular dementia, fronto-temporal dementia, Lewy bodies dementia, Creutzfeld-Jacob disease, epilepsy, migraine, anxiety, panic, psychosis, hypersensitive syndrome or pain.

The present invention thus concerns highly functionalizable Huprine derivatives of formula I:

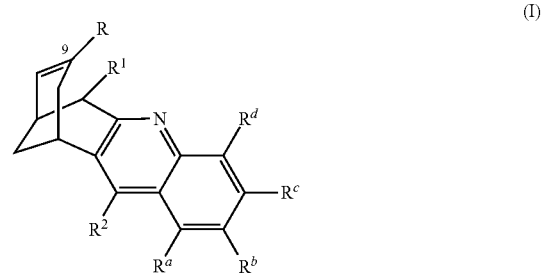

wherein,

R is a moiety comprising at least one functional group selected from the group consisting of a double bond, halo, cyano, hydroxy, sulfonyl, aldehyde, carbonyl, carboxy, ether, ester, carboxamide, amine, hydrazinyl, ammonium, azide and 5- or 6-membered heterocyclic group with the proviso that R is not allyl;

$R^a$, $R^b$, $R^c$ and $R^d$ are independently H, halogen, cyano, carboxy, —O($C_1$-$C_4$ alkyl), —S($C_1$-$C_4$ alkyl), or —$CH_2$S ($C_1$-$C_4$ alkyl); preferably H, halogen, cyano, —$SCH_3$ or —$CH_2SCH_3$; more preferably H or Cl; even more preferably $R^a$, $R^b$ and $R^d$ are H and $R^c$ is H or Cl;

$R^1$ is H or =$CH_2$; and $R^2$ is Cl or $NR^3R^{t3}$ wherein $R^3$ and $R^{t3}$ are independently H, acetyl, $C_1$-$C_4$ alkyl, —CO($C_1$-$C_4$ alkyl) or any hydrocarbyl chain linked to a ligand of the peripheral site of the AChE, preferably selected from phenyltetraisoquinoline derivatives, beta-carboline derivatives, indole derivatives or coumarine derivatives; preferably, $R^3$ and $R'^3$ are independently H, acetyl, $C_1$-$C_4$ alkyl or —CO($C_1$-$C_4$ alkyl); more preferably, $R^3$ and $R'^3$ are independently H or acetyl.

Preferably, R is a moiety of formula:

-A-Y-Z wherein,

A is $C_1$-$C_4$ alkylene or $C_2$-$C_4$ alkenylene; in a preferred embodiment, A is a linear $C_1$-$C_4$ alkylene or a linear $C_2$-$C_4$ alkenylene; more preferably, A is a linear $C_1$-$C_4$ alkylene or —CH═CH—; in another preferred embodiment, A is a branched $C_1$-$C_4$ alkylene or a branched $C_2$-$C_4$ alkenylene;

Y is a single bond, —O—, —C(O)—, —C(O)O—, —OC(O)—, —OS(O)$_2$—, —NH—, —N($R^4$)— or

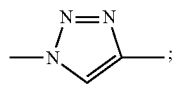

Z is H, halo, cyano, hydroxy, azide, hydrazinyl, —OR$^5$, —C(O)OR$^6$, —NR$^6$R$^7$, —N$^+$R$^6$R$^7$R$^8$, —CH(COOR$^6$)$_2$, —CH(CH$_2$OH)$_2$, CH$_2$—OC(O)—R$^9$, $C_1$-$C_4$ alkyl, $C_1$-$C_4$ alkyl substituted with halogen or hydroxy, $C_2$-$C_4$ alkenyl or $C_2$-$C_4$ alkenyl substituted with halogen or hydroxy; preferably Z is H, halo, cyano, hydroxy, azide, hydrazinyl, —OR$^5$, —C(O)OR$^6$, —NR$^6$R$^7$, —N$^+$R$^6$R$^7$R$^8$, —CH(COOR$^6$)$_2$, —CH(CH$_2$OH)$_2$, CH$_2$—OC(O)—R$^9$, methyl, ethyl, ethenyl, hydroxymethyl or trifluoromethyl;

$R^4$ and $R^5$ are independently $C_1$-$C_4$ alkyl or $C_1$-$C_4$ alkyloxycarbonyl; preferably, $R^4$ and $R^5$ are independently methyl or butyloxycarbonyl;

$R^6$, $R^7$ and $R^8$ are independently H or $C_1$-$C_4$ alkyl; preferably, $R^6$, $R^7$ and $R^8$ are independently H, methyl or ethyl; and $R^9$ is $C_1$-$C_4$ alkyl or $C_1$-$C_4$ alkyl substituted with halogen; preferably, $R^9$ is methyl or trifluoromethyl;

with the proviso that R is not alkyl or allyl.

More preferably, R is selected from the group consisting of —CH$_2$—COO—C$_2$H$_5$, —(CH$_2$)$_2$—OH, —CH═CH$_2$, —(CH$_2$)$_2$—OCO—CH$_3$, —(CH$_2$)$_2$—OCO—CF$_3$, —(CH$_2$)$_2$—O—CH$_3$, —(CH$_2$)$_2$—I, —(CH$_2$)$_2$—CN, —(CH$_2$)$_2$—Cl, —(CH$_2$)$_2$—F, —CH$_2$—COOH, —(CH$_2$)$_2$—N$_3$, —(CH$_2$)$_2$—OSO$_2$—CH$_3$, —(CH$_2$)$_2$—NH—NH$_2$, —(CH$_2$)$_2$—NH—OH, —(CH$_2$)$_2$—N(boc)-O(boc), —(CH$_2$)$_2$—OCO—NH$_2$, —(CH$_2$)$_2$—OCO—CH═CH$_2$, —CH$_2$—CO—N(CH$_3$)$_2$, —CH$_2$—CONH$_2$, —(CH$_2$)$_2$—N$^+$H(CH3)$_2$, —(CH$_2$)$_2$—(C$_2$H$_2$N$_3$)—COOCH$_3$, —(CH$_2$)$_2$—(C$_2$H$_2$N3)-CH$_2$OH, —(CH$_2$)$_2$—N$^+$H$_3$, —(CH$_2$)$_2$—N$^+$(CH$_3$)$_3$, —(CH$_2$)$_2$—CH—(COOCH$_3$)$_2$, —(CH$_2$)$_2$—CH—(COOC$_2$H$_5$)$_2$, —(CH$_2$)$_2$—CH—(CH$_2$OH)$_2$, —(CH$_2$)$_3$—COO—CH3, —(CH$_2$)$_4$—OH, —(CH$_2$)$_4$—OSO$_2$—CH$_3$, —(CH$_2$)$_4$—N$_3$, —(CH$_2$)$_4$—(C$_2$H$_2$N$_3$)—COOCH$_3$, —(CH$_2$)$_4$—(C$_2$H$_2$N$_3$)—CH$_2$OH, —(CH$_2$)$_4$—(C$_2$H$_2$N$_3$)—CH$_2$OCOCF$_3$, —(CH$_2$)$_3$—COO—C$_2$H$_5$.

The invention also concerns the pharmaceutically acceptable salts and prodrugs of compounds of formula I.

The expression "$C_2$-$C_4$ alkenyl" represents any monovalent radical of a linear or branched hydrocarbon chain comprising 2 to 4 carbon atom and at least one double bond, such as ethenyl, n-propenyl, i-propenyl, n-butenyl, i-butenyl, s-butenyl or t-butenyl.

The expression "$C_2$-$C_4$ alkenyl" represents any monovalent radical of a linear or branched hydrocarbon chain comprising 2 to 4 carbon atom and at least one double bound, such as ethenyl, n-propenyl, i-propenyl, n-butenyl, i-butenyl, s-butenyl or t-butenyl.

The expressions "$C_1$-$C_4$ alkyl substituted with halogen or hydroxy" or "$C_2$-$C_4$ alkenyl substituted with halogen or hydroxy" represent any $C_1$-$C_4$ alkyl or $C_2$-$C_4$ alkenyl group substituted with at least one halogen atom (selected from F, Cl or Br) or at least one hydroxy group, such as halomethyl, dihalomethyl, trihalomethyl, haloethyl, dihaloethyl, trihaloethyl, hydroxymethyl, hydroxyethyl, hydroxypropyl or hydroxybutyl.

The expression "$C_1$-$C_4$ alkylene" represents any divalent radical of a linear or branched hydrocarbon chain comprising 1 to 4 carbon atom, such as —CH$_2$—, —(CH$_2$)$_2$—, —(CH$_2$)$_3$—, —(CH$_2$)$_4$—. —CH(CH$_3$)—, —CH(CH$_3$)—CH$_2$—, —CH$_2$—CH(CH$_3$)—, —CH$_2$—CH$_2$—CH(CH$_3$)—, —CH$_2$—CH(CH$_3$)—CH$_2$— or —CH(CH$_3$)—CH$_2$—CH$_2$—.

The expression "$C_2$-$C_4$ alkenylene" represents any divalent radical of a linear or branched hydrocarbon chain comprising 2 to 4 carbon atom and at least one double bond, such as —CH═CH—, —CH═CH—CH$_2$—, —CH$_2$—CH═CH—, —CH═CH—CH$_2$—CH$_2$—, —CH$_2$—CH$_2$—CH═CH— or —CH$_2$—CH═CH—CH$_2$—.

The expression "5- or 6-membered heterocyclic group" represents 5- or 6-membered saturated rings comprising at least one heteroatom selected from N, 0 or S or unsaturated rings comprising at least one heteroatom selected from N, 0 or S and at least one double bond. Such heterocyclic group are for example pyrrolidine, pyrroline, pyrrole, imidazolidine, pyrazolidine, imidazole, imidazoline, pyrazole, pyrazoline, triazole, tetrazole, piperidine, pyridine, piperazme, diazine, triazine, tetrazine, tetrahydrofuran, dihydrofuran, dihydrofuran, furan, tetrahydropyran, pyran, dioxolane, dioxane, trioxane, dioxine, tetrahydrothiophene, dihydrothiophene, thiophene, dithiolane, thiane, dithiane or thiopyran.

The abbreviation "Me" represents a methyl group.

The abbreviation "Et" represents an ethyl group.

The abbreviation "Ac" represents an acetyl group.

The abbreviation "boc" represents a t-butyloxycarbonyl group.

In a first embodiment, the present invention concerns highly functionalizable Huprine derivatives of formula Ia:

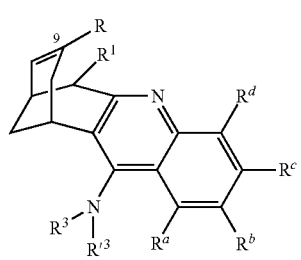

(Ia)

wherein R, $R^1$, $R^3$, $R'^3$, $R^a$, $R^b$, $R^c$ and $R^d$ are as defined in formula I; preferably, $R^a$, $R^b$ and $R^d$ are H and R, $R^1$, $R^3$, $R'^3$ and $R^c$ are as defined in formula I;

and pharmaceutically acceptable salts thereof.

In a first alternative of this embodiment, the present invention concerns highly functionalizable Huprine derivatives of formula Ia-1:

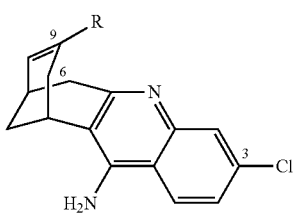
(Ia-1)

wherein R is as defined in formula I;
and pharmaceutically acceptable salts thereof.

In a second alternative of this embodiment, the present invention concerns highly functionalizable Huprine derivatives of formula Ia-2:

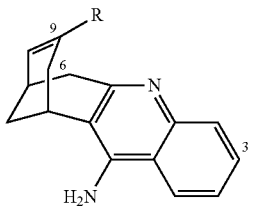
(Ia-2)

wherein R is as defined in formula I; preferably, R is —(CH$_2$)$_2$—N$_3$, —(CH$_2$)$_2$—OSO$_2$—CH$_3$, —(CH$_2$)$_2$—N$^+$H$_3$ or —(CH$_2$)$_4$—(C$_2$H$_2$N$_3$)—CH$_2$OH;
and pharmaceutically acceptable salts thereof.

In a third alternative of this embodiment, the present invention concerns highly functionalizable Huprine derivatives of formula Ia-3:

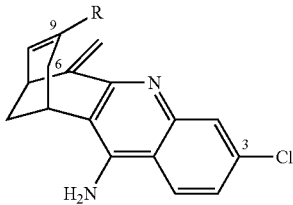
(Ia-3)

wherein R is as defined in formula I; preferably, R is —CH$_2$—COO—C$_2$H$_5$, —(CH$_2$)$_4$—OH or —(CH$_2$)$_4$—(C$_2$H$_2$N$_3$)—CH$_2$OCOCF$_3$;
and pharmaceutically acceptable salts thereof.

In a second embodiment, the present invention concerns highly functionalizable Huprine derivatives of formula Ib:

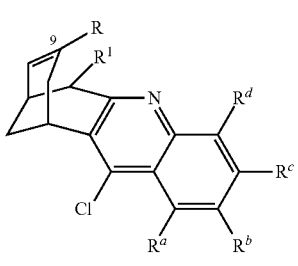
(Ib)

wherein R, R$^1$, R$^3$, R$^{t3}$, R$^a$, R$^b$, R$^c$ and R$^d$ are as defined in formula I; preferably, R$^a$, R$^b$ and R$^d$ are H and R, R$^1$, R$^3$, R$^{t3}$ and R$^c$ are as defined in formula I;
and pharmaceutically acceptable salts thereof.

In an alternative of this embodiment, the present invention concerns highly functionalizable Huprine derivatives of formula Ib-1:

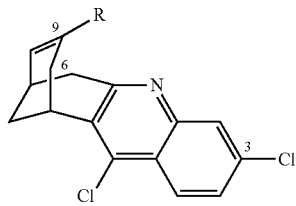
(Ib-1)

wherein R is as defined in formula I; preferably, R is —CH$_2$—COO—C$_2$H$_5$;
and pharmaceutically acceptable salts thereof.

In a particularly preferred embodiment, the compounds of the present invention are selected from the group consisting of:

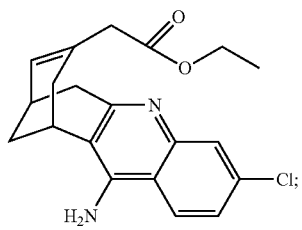
(HUP 1)

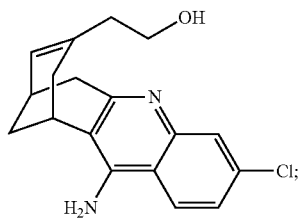
(HUP 2)

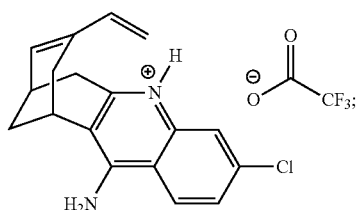
(HUP 3)

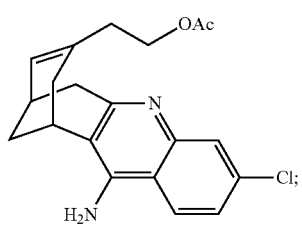
(HUP 4)

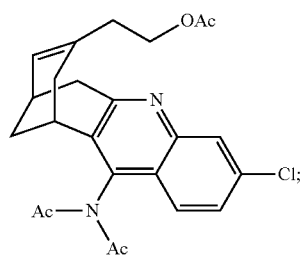
(N,N-diacyl-HUP 4)
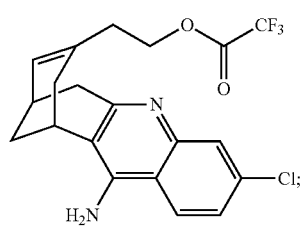
(HUP 5)
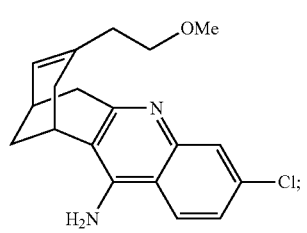
(HUP 6)
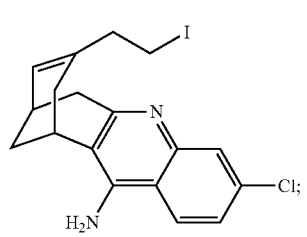
(HUP 7)
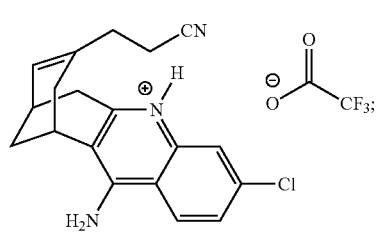
(HUP 8)
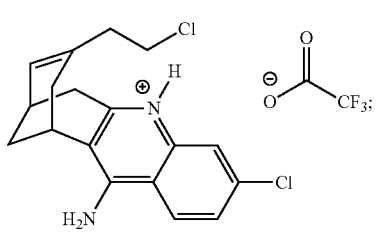
(HUP 9)
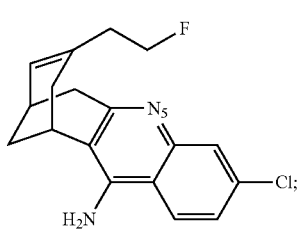
(HUP 10)
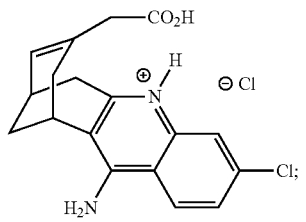
(HUP 11)
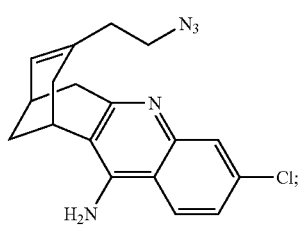
(HUP 12)
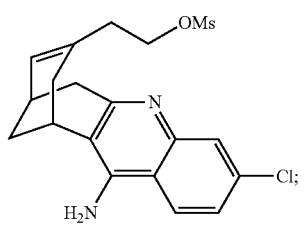
(HUP 13)
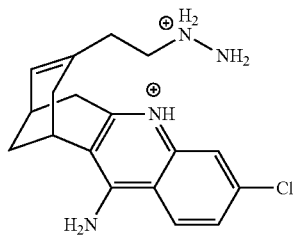
(HUP 14)
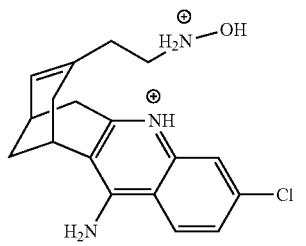
(HUP 15)
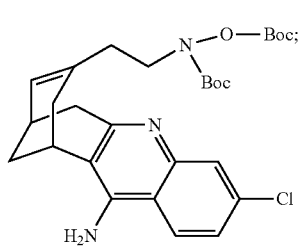
(HUP 16)
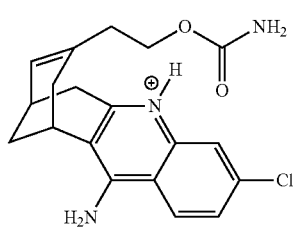
(HUP 17)

-continued
(HUP 18)
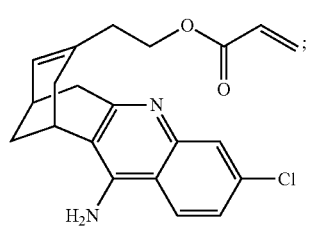
(HUP 19)
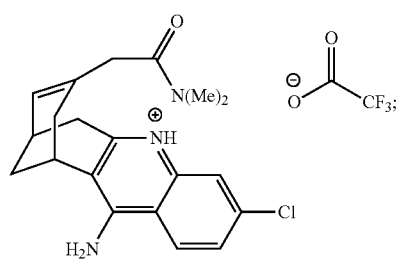
(HUP 20)
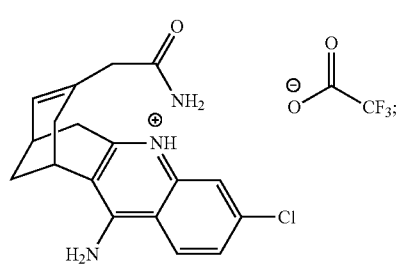
(HUP 21)
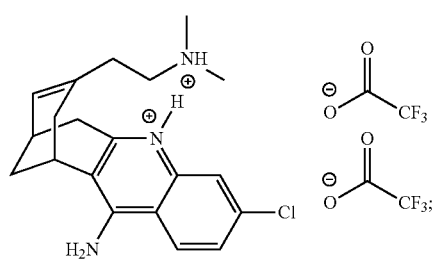
(HUP 22)
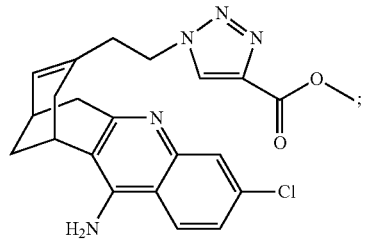
(HUP 23)
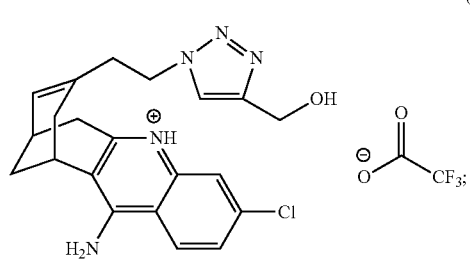
-continued
(HUP 24)
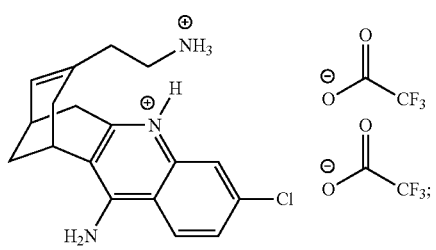
(HUP 25)
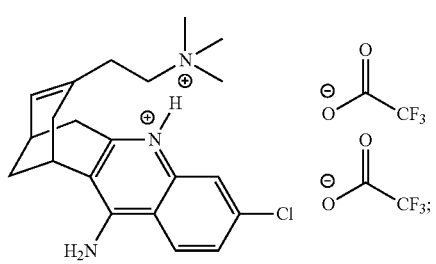
(HUP 26)
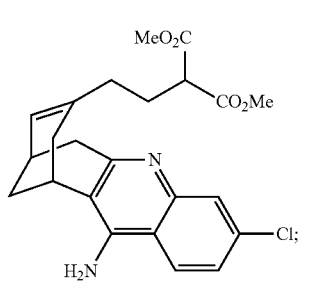
(HUP 27)
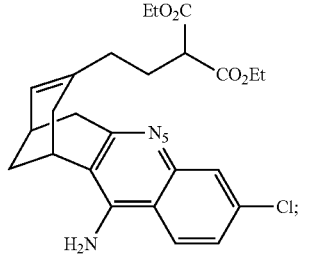
(HUP 28)
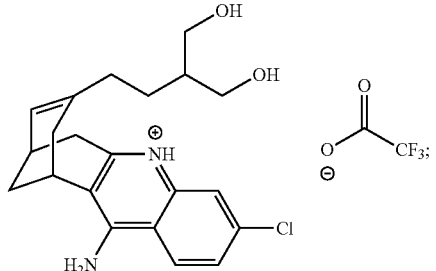
(HUP 29)
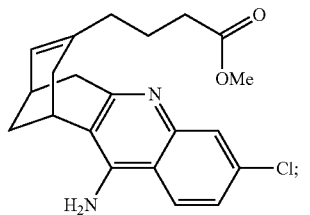

11
-continued
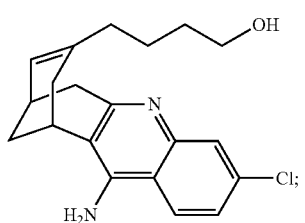
(HUP 30)
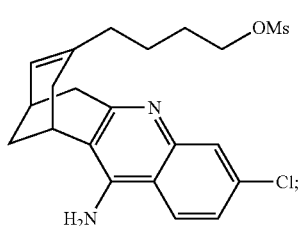
(HUP 31)
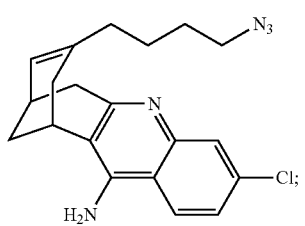
(HUP 32)
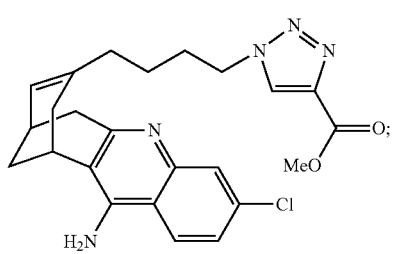
(HUP 33)
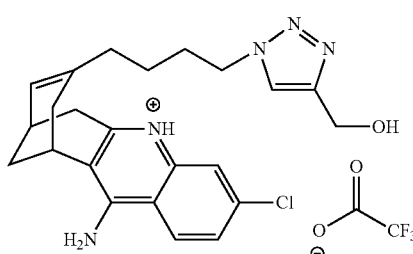
(HUP 34)
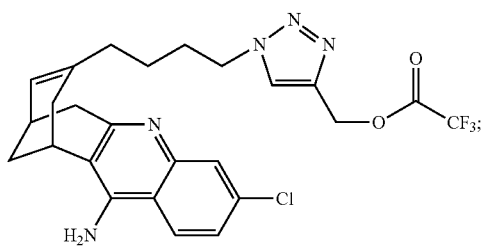
(HUP 35)
12
-continued
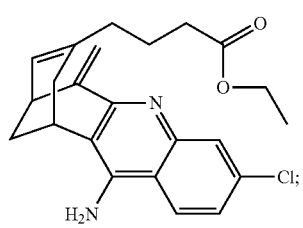
(HUP 36)
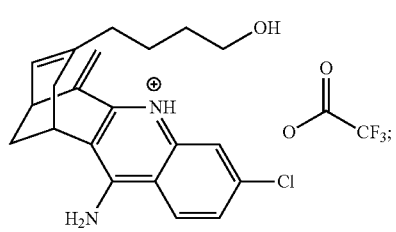
(HUP 37)
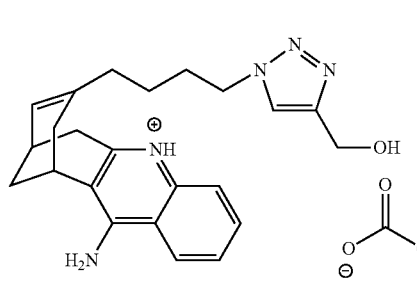
(HUP 38)
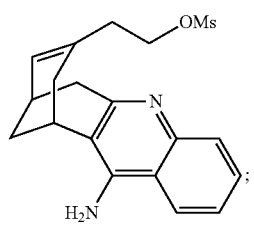
(HUP 39)
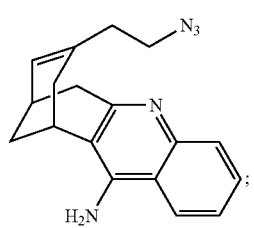
(HUP 40)
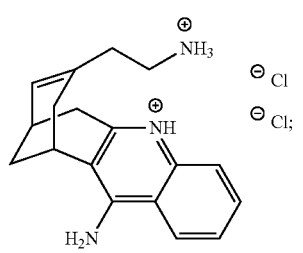
(HUP 41)

-continued

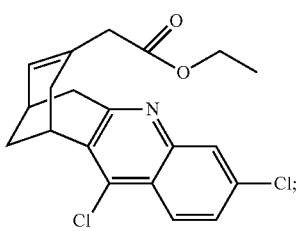
(HUP 42)

and pharmaceutically acceptable salts thereof.

This invention also relates to a method for preparing highly functionalizable Huprine derivatives of formula I comprising the steps of:

a) contacting the diketone of formula 1

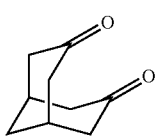
(1)

with an α-haloester, to obtain the compound of formula 2

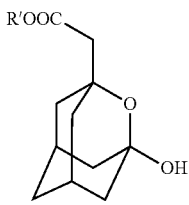
(2)

wherein R' is a $C_1$-$C_4$ alkyl;

b) transforming the alcoholic group of the compound of formula 2 into a leaving group to obtain the compound of formula 3

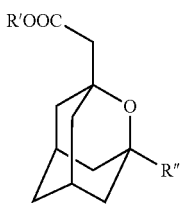
(3)

wherein R" is a leaving group;

b') eventually converting the compound of formula 3 into the compound of formula 4

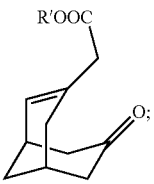
(4)

c) contacting the compound of formula 3 or 4 with the compound of formula 5

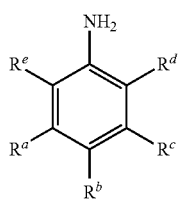
(5)

wherein $R^a$, $R^b$, $R^c$ and $R^d$ are as defined in formula I, and $R^e$ is CN or COOH, to obtain the compound of formula HUP

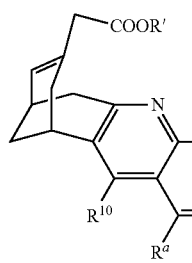
(HUP)

wherein R' is a $C_1$-$C_4$ alkyl and $R^{10}$ is $NH_2$ or Cl.

The diketone of formula 1 is commercially available and is also obtainable from 1,1,3,3-tetramethoxypropane and methyl acetone-1,3-dicarboxylate (Berz S. H., *J. Org. Chem.* 1985, 50, 3585).

The step a), introducing the functionalization, can be obtained by the addition of an organometallic compound, such as zinc, magnesium or lithium derivative organometallic compounds, to the diketone of formula 1. Preferably, step a) is based on the reaction of Reformatsky by condensing the diketone of formula 1 with an α-haloester using zinc metal. The haloester is preferably a compound of formula X'CH2COOR', wherein X' is a halogen and R' is a C1-C4 alkyl; more preferably, X' is Br and R' is a C1-C4 alkyl; even more preferably, X' is Br and R' is methyl or ethyl. This reaction is preferably carried out in a polar solvent; more preferably in tetrahydrofurane (THF) under reflux.

In step b), the alcoholic function of compound 2 is transformed into a leaving group. The leaving group R" can be selected from Br, carbonate, an arylsulfonyloxy such as tosylate, an alkylsulfonyloxy such as mesylate, or a haloalkylsulfonyloxy such as triflate. This step is obtained by contacting the compound of formula 2 with an appropriate reactant well known by the skilled man, for example $Br_2$, an arylsulfonylhalide, an alkylsulfonylhalide or a haloalkylsulfonyloxy. The reactant is preferably selected from methylsulfonylchloride and p-toluenesulfonylchloride leading to compound 3 wherein R" is mesylate or tosylate. The reaction condition can be easily determined by the skilled person. Preferably, step b) is carried out in a polar aprotic solvent, for example dichloromethane, in presence of a base, such as triethylamine, at 0° C.

The conversion of the compound 3 into compound 4 in step b') can be made by using a silica gel in an apolar aprotic solvent, such as 1,2-dichloroethane, under reflux. This conversion is however preferably obtained more quickly and with a higher yield in an apolar aprotic solvent, such as 1,2-dichloroethane, under reflux in the presence of a Lewis acid, for example aluminium trichloride.

The condensation of compound 3 or 4 with the compound 5 in step c) is carried out by following the Friedländer reaction. This reaction is made in apolar aprotic solvent, preferably 1,2-dichloroethane, under reflux in presence of a Lewis acid, such as aluminium trichloride. When compound 5 is chosen among aminobenzonitril derivatives (i.e. when $R^e$ is CN), step c) leads to the compound of formula (HUP) wherein $R^{10}$ is $NH_2$. Preferred aminobenzonitril derivatives are 2-aminobenzonitrile ($R^e$ is CN, and $R^a$, $R^b$, $R^c$ and $R^d$ are H) or 4-chloro-2-aminobenzonitrile ($R^e$ is CN, $R^a$, $R^b$ and $R^d$ are H and $R^c$ is Cl). When the compound of formula 5 is chosen among aminobenzoic acid derivatives (i.e. when $R^e$ is COOH), a further reaction in presence of phosphorous oxychloride leads to the compound of formula (HUP) wherein $R^{10}$ is Cl. Preferred aminobenzoic acid derivatives are 2-aminobenzoic acid ($R^e$ is COOH, and $R^a$, $R^b$, $R^c$ and $R^d$ are H) or 4-chloro-2-aminobenzoic acid ($R^e$ is COOH, $R^a$, $R^b$ and $R^d$ are H and $R^c$ is Cl).

In a first embodiment, the method of the invention comprises the steps of:

a) contacting the diketone of formula 1

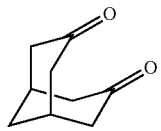

(1)

with an α-haloester, to obtain the compound of formula 2

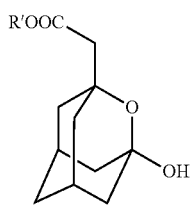

(2)

wherein R' is a $C_1$-$C_4$ alkyl;

b) transforming the alcoholic group of the compound of formula 2 into a leaving group to obtain the compound of formula 3

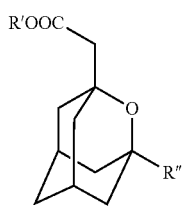

(3)

wherein R" is a leaving group;

b') converting the compound of formula 3 into the compound of formula 4

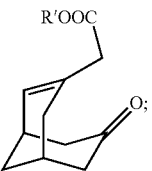

(4)

c) contacting the compound of formula 4 with the compound of formula 5

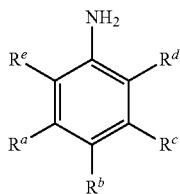

(5)

wherein $R^a$, $R^b$, $R^c$ and $R^d$ are as defined in formula I, and $R^e$ is CN or COOH, to obtain the compound of formula HUP

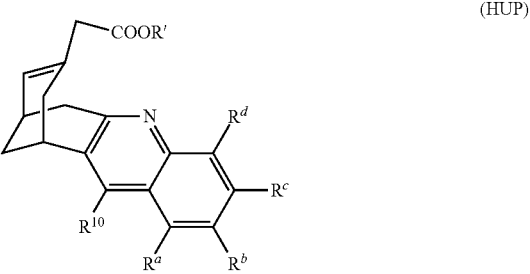

(HUP)

wherein R' is a $C_1$-$C_4$ alkyl and $R^{10}$ is $NH_2$ or Cl.

In a second embodiment, the method of the invention comprises the steps of:

a) contacting the diketone of formula 1

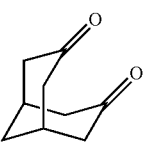

(1)

with an α-haloester, to obtain the compound of formula 2

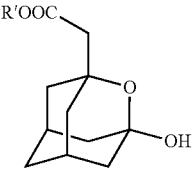

(2)

wherein R' is a $C_1$-$C_4$ alkyl;

b) transforming the alcoholic group of the compound of formula 2 into a leaving group to obtain the compound of formula 3

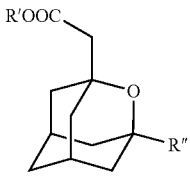

(3)

wherein R" is a leaving group;
c) contacting the compound of formula 3 with the compound of formula 5

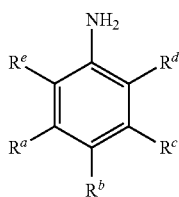

(5)

wherein $R^a$, $R^b$, $R^c$ and $R^d$ are as defined in formula I, and $R^e$ is CN or COOH, to obtain the compound of formula HUP

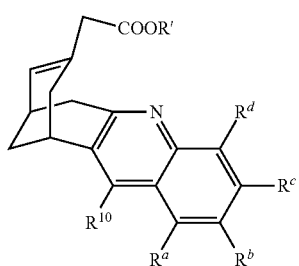

(HUP)

wherein R' is a $C_1$-$C_4$ alkyl and $R^{10}$ is $NH_2$ or Cl.

The advantage of this embodiment is that compound 3 is directly transformed into the compound HUP in a one-pot fragmentation-Friedländer's condensation reaction carried out in step c).

The compounds of formula I can be obtained from the compound of formula HUP through further additional steps which are easily determined by the skilled person in the art for rearranging the functionalization on position 9. Some of the possible functional rearrangements are detailed in the following examples.

The compounds of the invention exhibit high affinity towards the AChE and the BuChE (butyrylcholinesterase), with a high specificity toward AChE when a chlorine atome si substitutes on position 3 of the compounds of the invention. Moreover, such compounds are accessible via relatively simple synthesis allowing a high adaptability of their molecular structure, especially on position 9. Consequently, the compounds of the invention can be use in various applications exploiting their high affinity toward the AChE and the BuChE and their high functionalizability. Among possible applications, the compounds of the invention can be used, for example, as an inhibitor of the AChE or the BuChE, especially for treating neurodegenerative diseases or for the structural analysis of the complex AChE-inhibitor; as probes for the evolution of neurodegenerative disease through mapping of the functional cholinergic neurons; taking into account their high selectivity towards AChE or BuChE, as selector or chiral selector for affinity chromatography and purification of those enzymes; or, taking into account their particular structures, as enantioselective catalyst.

Due to their high affinity towards the AChE and the BuChE, the compounds of the invention can be used as inhibitors of the AChE or the BuChE. The present invention also concerns an inhibitor or part of an inhibitor of the AChE or the BuChE of general formula I. It also concerns the use of a compound of formula I as an inhibitor of the AChE or the BuChE.

Several inhibitor of the AChE, as disclosed above, are already available. However, although many compounds exhibit high affinity in vitro, only few compounds can be used as active principle because those compounds and their derivatives risk having a low liposolubility and thus do not cross easily the blood-brain barrier. On the contrary, in addition to the nanomolar affinity and the high selectivity of the compounds of the invention for the AChE, lipophilic vector can be easily coupled to the compounds of the invention. The high functionalizability of the compounds of the invention can be used to mask the hydrophilic properties of the inhibitor thanks to an enzymolabil function or a function labil under particular conditions such as redox chemical delivery systems based on NADH models developed by Bodor et al. (Eur. J. Med. Chem. Volume 39, Issue 8, 2004, Pages 715-727). It is thus possible to produce a highly lipophilic pharmaceutically inactive prodrug of an inhibition of the AChE allowing the inhibitor to cross the blood-brain barrier. Once inside the central nervous system, the prodrug is transformed into the hydrosoluble active form which is trapped inside the blood-brain barrier. The availability of the active compound towards the target is then increased and the effective dose can be reduced. Consequently, the side effects and peripheral effects induced by those compounds are minimized. For example, the hydrosoluble compound (HUP 2), having an activity as high as the Huprine X, comprises an alcohol function which can be coupled into a lipophilic vector such as acetate (HUP 4) or trifluoroacetate (HUP 5). A gain up to 1.5 units for the log P is obtained compared to the Huprine X. More generally, long chain fatty acid esters or other lipophilic substituent can be branched on the adequately functionalized position 9 allowing adapting the lipophilic properties of the compound.

The present invention also concerns dimeric compounds consisting of the compound of formula I further coupled to another molecular structure. Since any desired function can be branched on the position 9, the compound of the invention can be further coupled to another molecular structure so as to form a dimeric compound. Therefore, the compound of formula I is advantageously coupled to said molecular structure through an appropriate functionalization on position 9. The molecular structure coupled to the compound of formula I is chosen among compounds having their own activity so as to confer specific properties to the dimeric compound, e.g. enhanced inhibiting properties or additional properties such as a role in the aggregation of beta-amyloïd peptides. Said molecular structure is for example selected from phenyltetraisoquinoline derivatives, beta-carboline derivatives, indole derivatives or coumarine derivatives.

Alzheimer disease is the most prevalent type of senile dementia. The invariable histological hallmark of the disease is the deposition in the brain tissue of amyloid plaques, whose main constituent is a 40-42 amino-acids peptide referred to the amyloid-beta peptide. The beta-amyloid peptide forms oligomeric and fibrillar assemblies that have both been shown to be toxic. Accumulating evidence from in vitro studies suggest that toxicity is greater for oligomers compared to fibrils.

In addition to the plaques, a decrease in acetylcholine levels is observed in the brains of Alzheimer disease patients. Therefore, symptomatic treatment has focused so far on AChE reversible inhibition. This is illustrated by the fact that four out of the five currently approved Alzheimer disease drugs targeted the AChE active site. It has been shown that beta-amyloid peptide interacts with AChE following a mechanism involving its peripheral site and residues 12-28 of the beta-amyloid peptide. This interaction results in the acceleration of beta-amyloid peptide/fibrils deposition and an increase of amyloid-plaques neurotoxicity. Second-generation anti-Alzheimer disease drugs are therefore intended to exert their action by targeting both the peripheral and the active site of AChE, thereby restoring brain acetylcholine levels, on one hand, and inhibiting AChE-mediated acceleration of amyloid-beta peptide fibrillation, on the other hand. In this context, dimeric compounds consisting of the compound of formula I coupled to a ligand of AChE peripheral site have been designed. The huprine moiety tightly binds to AChE active site, while the ligand of the peripheral site is anchored at the peripheral site. Accordingly, such dimeric compounds, such as HUP32-COU1, are very potent inhibitors of AChE that feature a dissociation constant in the picomolar-range.

Among such dimeric compounds, dimeric inhibitors are particularly interesting. Indeed, the AChE presents two active sites, an acylation site and a peripheral site, connected through an internal gorge. The compounds of formula I have a high affinity towards the acylation site. In a particular embodiment, the present invention concerns a dimeric compound consisting of the compound of formula I further coupled to a ligand of the peripheral site of the AChE or the BuChE. The length of the substituent of the 9 position of the Huprine of formula I can be adapted so that the dimeric inhibitor presents an adapted structure to inhibit at the same time the two active sites of the AChE. Noteworthingly, all such dimeric inhibitors have been designed to date through modification of the aniline function at the position 12 of Huprines and Tacrines. Yet, providing an X-ray crystallographic structure of derivative (HUP2) in the acylation site of human AChE allowed us to discover that the 9 position offered a more flexible access to the peripheral site of AChE. The coupling of the Huprines of formula I and the ligand of the peripheral site can for example be performed with a Huisgen 1,3-dipolar cyloaddition. The compounds of formula I are preferably coupled to a ligand of the peripheral site of the AChE selected from phenyltetraisoquinoline derivatives, beta-carboline derivatives, indolic derivatives and coumarin derivatives. More preferably, the dimeric inhibitor is selected from compounds of formula HUP32-PIQ1, HUP32-PIQ2, HUP32-PIQ3, HUP32-PIQ4, HUP32-COU1, HUP32-COU2, HUP32-COU3, HUP32-IND1, HUP32-IND2, HUP32-TPI1, HUP32-TPI2, HUP32-PPI1 and HUP32-PPI2:

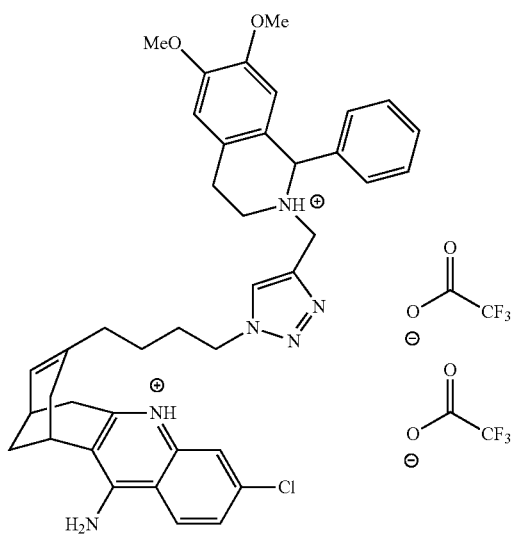

(HUP32-PIQ1)

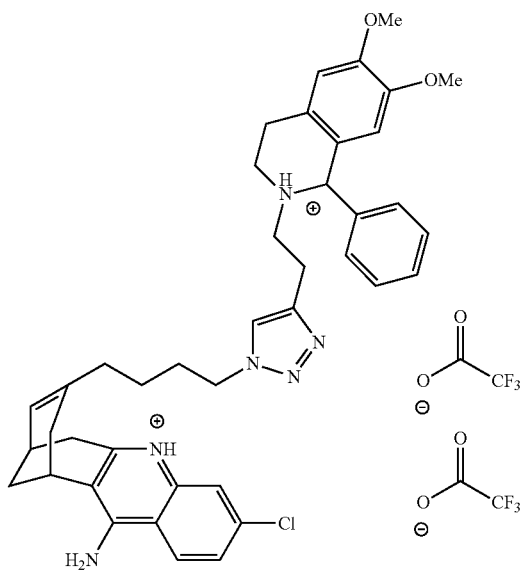

(HUP32-PIQ2)

21
-continued
(HUP32-PIQ3)
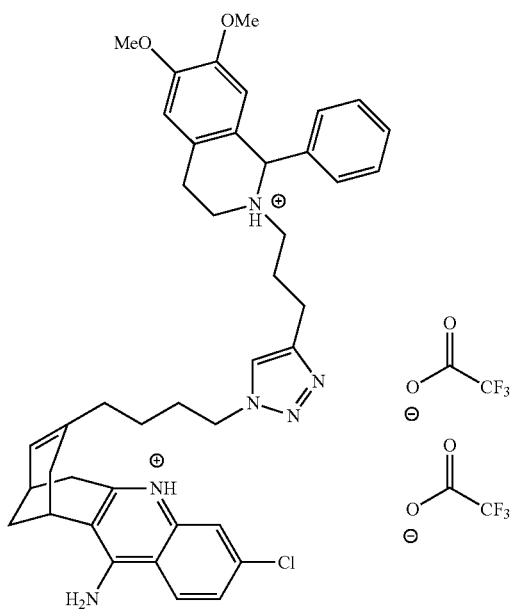
22
-continued
(HUP32-COU1)
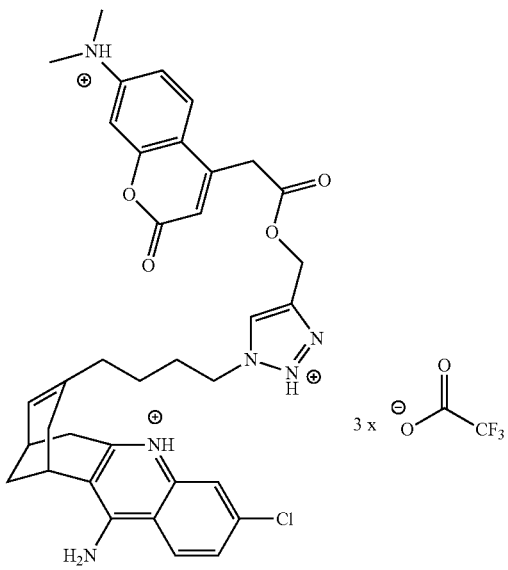
(HUP32-PIQ4)
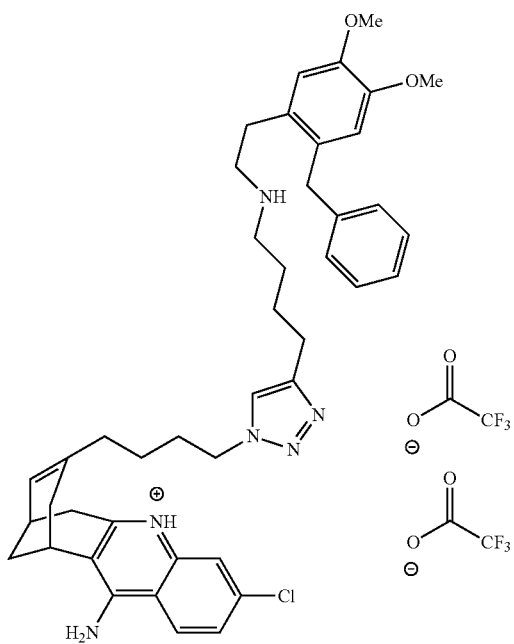
(HUP32-COU2)
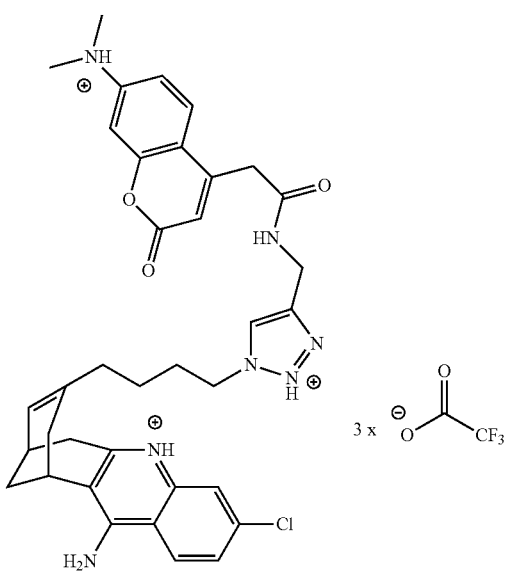

(HUP32-COU3)
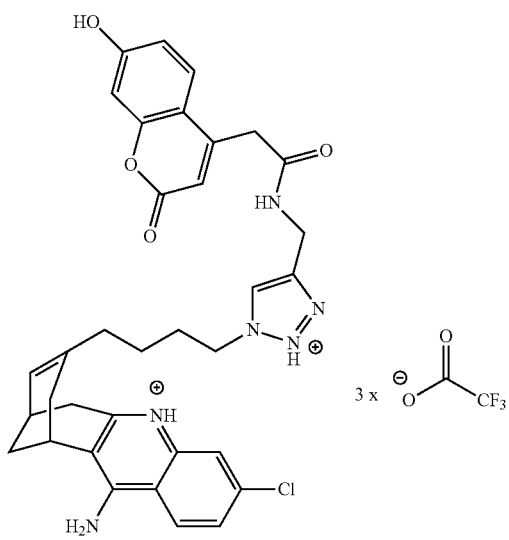
(HUP32-TPI1)
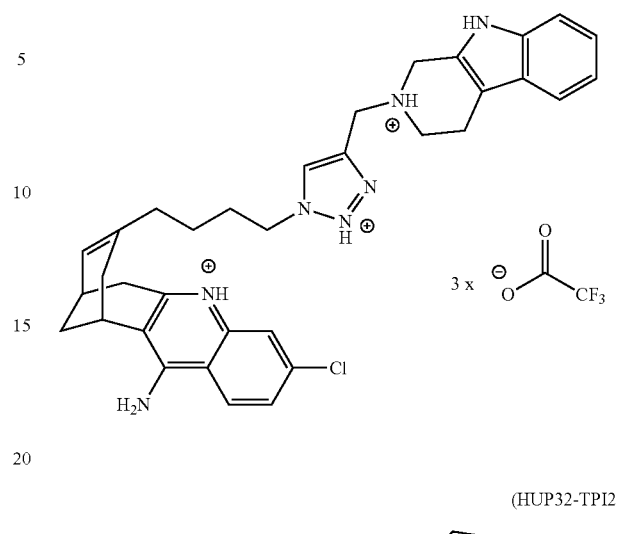
(HUP32-IND1)
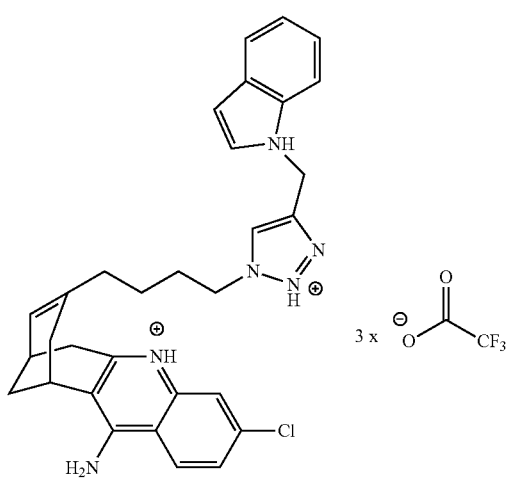
(HUP32-TPI2)
(HUP32-IND2)
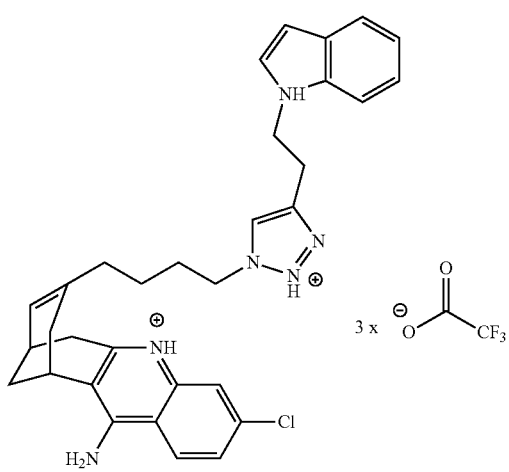
(HUP32-PPI1)
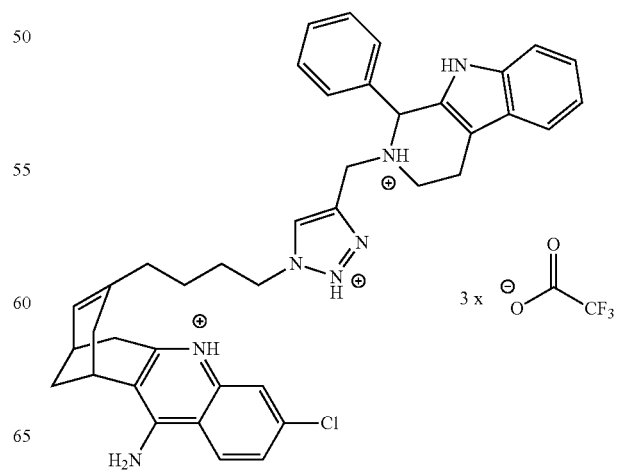

-continued (HUP32-PPI2)

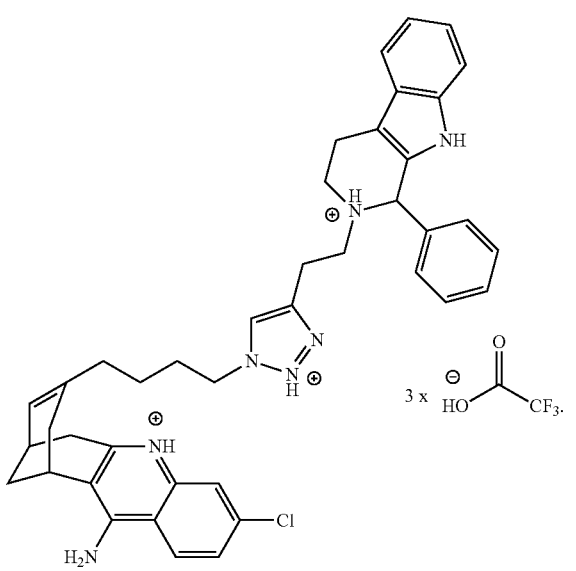

The present invention also concerns a dimeric inhibitor of the AChE or the BuChE selected form dimeric compounds consisting of the compound of formula I further coupled to a ligand of the peripheral site of the acetylcholinesterase or the butyrylcholinesterase, preferably selected from phenyltetraisoquinoline derivatives, beta-carboline derivatives, indolic derivatives and coumarin derivatives, more preferably selected from compounds of formula HUP32-PIQ1, HUP32-PIQ2, HUP32-PIQ3, HUP32-PIQ4, HUP32-COU1, HUP32-COU2, HUP32-COU3, HUP32-IND1, HUP32-IND2, HUP32-TPI1, HUP32-TPI2, HUP32-PPI1 and HUP32-PPI2. The present invention also concerns the use of such dimeric compounds as a dimeric inhibitor of the AChE or the BuChE. The dimeric inhibitors have an increased affinity towards the AChE compared to the compounds of formula I. Also, the dimeric compounds can have a role upstream from neurodegenerative diseases through the prevention of β-amyloid plaques deposit responsible for such diseases.

AChE inhibitors inhibit the cholinesterase enzyme from breaking down acetylcholine, increasing both the level and duration of action of the neurotransmitter acetylcholine. The compounds of formula I are therefore useful for treating neurological conditions where cholinergic deficiencies are involved. An object of the invention is therefore the compound of formula I, the inhibitor of formula I or the dimeric inhibitor as defined above for the manufacture of a medicament. Especially, the present invention also concerns the compound of formula I, the inhibitor of formula I or the dimeric inhibitor as defined above for the manufacture of a medicament for the treatment, preferably the palliative treatment, of neurological condition.

The invention is also dedicated to the use of a the compound of formula I, the inhibitor of formula I or the dimeric inhibitor as defined above for the manufacture of a medicament, preferably a medicament for the treatment of neurological condition, more preferably, the palliative treatment of neurological condition.

The invention also concerns the compound of formula I or the dimeric compound as defined above for use in the therapeutical treatment of the human body, preferably in the treatment or prevention of a neurological condition.

The neurological condition is preferably selected from the group consisting of Alzheimer's disease, multiple sclerosis, cognitive disorders, memory disorder, depressive disorders, bipolar disorder and schizophrenic disorders, Parkinson's' disease, Huntington's disease, vascular dementia, fronto-temporal dementia, Lewy bodies dementia, Creutzfeld-Jacob disease, epilepsy, migraine, anxiety, panic, psychosis, hypersensitive syndrome and pain. More preferably, the neurological condition is Alzheimer's disease.

The invention also concerns a pharmaceutical composition comprising an effective amount of a compound of formula I, an inhibitor of formula I, a dimeric inhibitor as defined above, a pharmaceutically acceptable salt thereof or a prodrug thereof. The pharmaceutical composition mentioned above may be administered in any suitable way, for example orally or parenterally, and it may be presented in any suitable form such as in the form of tablets, capsules, powders, syrups or solutions or dispersions for injection.

The present invention also concerns the use of a compound of formula I for affinity chromatography. The compound of formula I can be fixed on appropriate support material, for example polymeric resins, through introduction at the position 9 of a reactive linker suitable for the covalent grafting onto the polymeric support, such as an amine. Such affinity resins containing appropriately functionalized Huprine of formula I are very useful for the purification of the large scale produced BuChE or AChE.

The invention also concerns the use of a compound of formula I as enantioselective catalyst. The compound of formula I have a 4-aminopyridine type structure close to the structure of N,N-dimethylaminopyridine (DMAP). The appropriate functionalization of the position 9 offers the possibility to obtain catalysts having both a Lewis base part (4-aminopyridine) and a Brønsted acid, Lewis acid or another Lewis base on the substituent on position 9.

The following examples illustrate different method for preparing the compounds of the present invention. These examples represent specific embodiments of the invention and are not intended as limiting the scope of the invention.

In general, column chromatography purifications were performed on silica gel (40-63 μm) from SdS. Thin-layer chromatography (TLC) was carried out on Merck DC Kieselgel 60 F-254 aluminium sheets. Compounds were visualized by one of the two following methods: (1) illumination with a short wavelength UV lamp (λ=254 nm) or (2) staining with a 3.5% (w/v) phosphomolybdic acid solution in absolute ethanol. All solvents were dried following standard procedures ($CH_2Cl_2$, 1,2-dichloroethane and $CH_3CN$: distillation over $P_2O_5$, DMF and DMSO: distillation over BaO under reduced pressure, THF, toluene and $Et_2O$: distillation over Na/benzophenone). Triethylamine (TEA) and pyridine were distilled from $CaH_2$ and stored over BaO or KOH.

Melting points were recorded on a LEICA VMHB Kofler system at atmospheric pressure and were uncorrected. Microanalyses were carried out on Carlo-Erba 1106. Infrared spectra were recorded as KBr pellets using a Perkin Elmer FT-IR Paragon 500 spectrometer with frequencies given in reciprocal centimeters ($cm^{-1}$). $^1H$ and $^{13}C$ NMR spectra were recorded on a Bruker DPX 300 spectrometer (Bruker, Wissembourg, France). Chemical shifts are expressed in parts per million (ppm) from $CDCl_3$ ($\delta_H$=7.26, $\delta_C$=77.16), DMSO-$d_6$ ($\delta_H$=2.50, $\delta_C$=39.52) or $CD_3OD$ ($\delta_H$=3.31, $\delta_C$=49.00). $^1J$ values are expressed in Hz. Mass spectra were obtained with a Finnigan LCQ Advantage MAX (ion trap) apparatus equipped with an electrospray source. All analyses were performed in the positive mode.

Analytical HPLC was performed on a Thermo Electron Surveyor instrument equipped with a PDA detector under the following conditions: Thermo Hypersil GOLD C18 column (5μ, 4.6×150 mm) with $CH_3CN$ and 0.1% aqueous TFA as eluents [90% TFA (5 min), linear gradient from 0 to 100% of $CH_3CN$ (40 min)] at a flow rate of 1.0 mL·$min^{-1}$ dual UV detection at 254 and 270 nm. Two chromatographic systems were used for the preparative HPLC purification steps:

System A: reversed-phase HPLC (C18, Thermo Hypersil GOLD, 5μ, 21.2×250 mm) with $CH_3CN$ and trifluoroacetic acid 0.1% (TFA 0.1%, pH 2.0) as the eluents [100% TFA (5 min), then linear gradient from 0 to 100% (50 min) of $CH_3CN$] at a flow rate of 20.0 mL/min. UV-Visible detection was achieved at 264 nm.

System B: reversed-phase HPLC (C18, Thermo Hypersil GOLD, 5μ, 21.2×250 mm) with MeOH and trifluoroacetic acid 0.1% (TFA 0.1%, pH 2.0) as the eluents [100% TFA (5 min), then linear gradient from 0% to 20% (10 min) of MeOH, then linear gradient from 20% to 100% (40 min) of MeOH] at a flow rate of 15.0 mL/min. UV-Visible detection was achieved at 264 nm.

EXAMPLE 1

Ethyl (12-Amino-3-chloro-6,7,10,11-tetrahydro-7,11-methanocycloocta[b]quinolin-9-yl)acetate (HUP 1)

Preparation of tetramethyl 3,7-Dihydroxybicyclo[3.3.1]nona-2,6-diene-2,4,6,8-tetracarboxylate A mixture of 1,1,3,3 tetramethoxypropane (32.8 g, 0.20 mol) and 2 M HCl (100 mL) was stirred for 1.5 h at room temperature. To this mixture cooled at 0° C. was added successively and carefully an aqueous solution of 5 M NaOH within 30 min (pH=8) and MeOH (100 mL). At 0° C., dimethyl-3-oxoglutarate (69.6 g, 0.40 mol) was added, followed by addition of MeOH (70 mL). The reaction mixture was allowed to warm to room temperature and stirred for 3 days. The reaction mixture was acidified to pH=3 with 10 M HCl. Filtrating fractionwise, washing with water and drying at the dessicator afford the desired tetra ester as a white solid (39.2 g, 51%).

Preparation of bicyclo[3.3.1]nonane-3,7-dione (1)

A suspension of tetramethyl 3,7-dihydroxybicyclo[3.3.1]nona-2,6-diene-2,4,6,8-tetracarboxylate (19.2 g, 50 mmol) in an aqueous solution of 10 M HCl (50 mL), water (50 mL) and glacial acetic acid (100 mL) was heated at 130° C. for 6 h. After cooling at room temperature, the reaction mixture was poured onto crushed ice (200 mL) and extracted with DCM (4×200 mL). The combined organic layers were washed with an aqueous saturated solution of $NaHCO_3$. The organic layer was dried over $MgSO_4$, and concentrated under reduced pressure to give an orange solid. This crude product was dissolved in acetone and the salts which precipitated were filtered. Concentration of the filtrate and washing with $Et_2O$ afford the desired diketone (1) as a white solid (6.5 g, 85%).

Preparation of ethyl (3-Hydroxy-2-oxatricyclo[3.3.1.1³,⁷]dec-1-yl)acetate (2)

Zn solid was activated just prior to perform Reformatsky reaction as followed: Zn dust was stirred at r.t. in 2 M aqueous HCl solution until the bubbling ceased (≈40 min for 15 g Zn). The solid was then filtered and washed with water (50 mL), the EtOH (50 mL), acetone (50 mL), then $Et_2O$ (50 mL) and the thin solid was heated using an air gun under vacuum to complete drying. Reformasky reaction: to a suspension of such activated Zn* solid (2.29 g, 35 mmol) in dry THF (70 mL) warmed to reflux temperature under argon was added dropwise through the condenser over 40 min a mixture of ethylbromoacetate (1.75 mL, 15 mmol) and diketone (1) (0.761 g, 5 mmol) in dry THF (125 mL). The green mixture was stirred at reflux temperature for 5 h, then cooled to r.t. and hydrolyzed by quite slow addition of saturated aqueous $NH_4Cl$ solution (until pH=5-6): the resulting colorless solution with the Zn solid floating around was stirred for 10 min at r.t. before extraction with DCM (3×80 mL). The combined org. layers were washed with saturated solution of $NaHCO_3$ (80 mL), then brine (80 mL), then water (80 mL), dried with $MgSO_4$ and concentrated under reduced pressure to afford an orange oil. This crude product was then filtered trough a plug of silica gel and washed with AcOEt/cyclohexane mixtures, then with pure AcOEt to afford the desired acetal (2) as yellow oil pure enough to carry on the synthesis. A purer product can be obtained as white crystals (1.044 g, 87%) after flash chromatography (AcOEt/cyclohexane 4/6, v/v).

Preparation of ethyl {3-[(Methylsulfonyl)oxy]-2-oxatricyclo[3.3.1.1³,⁷]dec-1-yl}acetate (3)

A solution of adamantanol (2) (600 mg, 2.5 mmol) and triethylamine (540 μL, 3.75 mmol) in dry DCM (12 mL) under argon was cooled to 0° C. Methane sulfonyl chloride (290 μL, 3.75 mmol) was then added dropwise and the cooling bath was allowed to melt. After 30 min stirring, the solution was carefully poured onto a mixture of 2 M aqueous HCl solution (20 mL) and crushed ice. The organic layer was separated and the aqueous one extracted with DCM (3×20 mL). The combined organic layers were washed with saturated solution of $NaHCO_3$ (20 mL), then brine (20 mL), then water (20 mL), dried with $MgSO_4$ and concentrated under reduced pressure to afford an orange oil. This crude product is then filtered trough a plug of silica gel and washed with AcOEt/cyclohexane 3/7, v/v mixture to afford the desired methanesulfonate as quite yellow oil (800 mg, quantitative). Purification by flash chromatography (AcOEt/cyclohexane 2/8, v/v) afforded the desired product (3) as white crystals (755 mg, 95%).

Preparation of ethyl (7-Oxobicyclo[3.3.1]non-2-en-3-yl)acetate (4)

Method 1

A mixture of mesylate (3) (4.0 g, 12.55 mmol) and dry silica (40-63 μm, dried in oven at 110° C. for at least 12 h) in distilled 1,2-dichloroethane (40 mL) was stirred under argon at reflux temperature for 18 h. The cooled reaction mixture was then filtered and the residue washed with AcOEt/cyclohexane 3/7, v/v. Concentration of the dark pink filtrate then purification by chromatography (AcOEt/cyclohexane 0/10 to 3/7, v/v) afforded a colorless oil (910 mg, 4.094 mmol) along with some hydrolysed product adamantanol (2) (135 mg, 0.561 mmol), ratio desired enone (4)/adamantanol (2) 8.5/1, global yield 37% over 3 steps.

Method 2

A mixture of mesylate (3) (1.435 g, 4.5 mmol) and anhydrous aluminium trichloride (720 mg, 5.4 mmol) in distilled 1,2-dichloroethane (12 mL) was stirred was stirred under argon at reflux temperature for 10 min then cooled to r.t. The reaction mixture was diluted with water (24 mL) and THF (24 mL), made basic with 5 M NaOH (30 mL) and stirred at r.t. 30 min before extraction with DCM (2×50 mL), then with AcOEt (2×50 mL). The combined organic layers were dried with $MgSO_4$ and concentrated under reduced pressure to afford a pale yellow oil. Purification by flash chromatography (AcOEt/cyclohexane 0/10 to 3/7, v/v) afforded the desired enone (4) as colorless oil (920 mg, 92%).

Preparation of ethyl (12-Amino-3-chloro-6,7,10,11-tetrahydro-7,11-methanocycloocta[b]quinolin-9-yl)acetate (HUP 1)

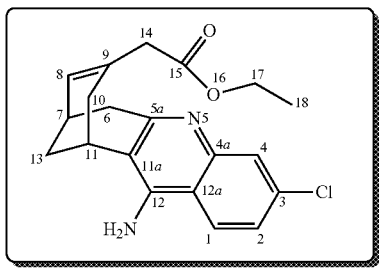

$C_{20}H_{21}ClN_2O_2$
Mol. Wt.: 356.85

Method 1 (from ethyl (7-Oxobicyclo[3.3.1]non-2-en-3-yl)acetate (4))

To a suspension of anhydrous $AlCl_3$ (980 mg, 7.35 mmol) and 4-chloro-2-aminobenzonitrile (1.12 g, 7.35 mmol) in distilled 1,2-dichloroethane (10 mL) under argon was added a solution of enone (4) (1.09 g, 4.9 mmol) in dry 1,2-dichloroethane (10 mL) dropwise over 10 min at r.t. The reaction mixture was stirred at reflux for 14 h then cooled to r.t. The solution was diluted with water (25 mL) and THF (25 mL), basified by addition of 5 M NaOH solution (30 mL) and stirred at r.t. for 30 min. The solution was then extracted with DCM (2×50 mL) then with AcOEt (3×50 mL). The combined organic layers were dried with $MgSO_4$ and concentrated to afford a yellow solid. Purification by flash chromatography (cyclohexane/AcOEt 1/1 to AcOEt/MeOH 95/5, v/v) afforded the desired Huprine (HUP 1) as a pale yellow solid (1.59 g, 91%).

Method 2 (from 3-ethylacetate-2-oxa-1-adamantyl methanesulfonate (3))

A suspension of anhydrous $AlCl_3$ (417 mg, 3.13 mmol) and mesylate (3) (830 mg, 2.6 mmol) in dry 1,2-dichloroethane (4 mL) was stirred at reflux. The reaction mixture became orange and exothermic. After 5 minutes, a suspension of 4-chloro-2-aminobenzonitrile (438 mg, 2.87 mmol) in dry 1,2-dichloroethane (5 mL) was added dropwise to the refluxing mixture and the reflux was maintained for 8 h. The reaction mixture was then cooled to r.t., diluted with water (10 mL) and THF (10 mL), basified by addition of 5 M NaOH solution (10 mL) and stirred at r.t. for 30 min. The phases were separated (DCM was added if necessary) and the aqueous layer was extracted with AcOEt (3×20 mL). The combined organic layers were dried with $Na_2SO_4$ and concentrated under reduced pressure to afford a yellow solid. Purification by flash chromatography (cyclohexane/AcOEt 10/0 to AcOEt/MeOH 9/1, v/v) afforded a pale yellow solid. Recrystallisation from petroleum ether/AcOEt, 8/2, v/v afforded the desired Huprine (HUP 1) as a white solid (799 mg, 88%).

Rf (AcOEt/MeOH 9/1, v/v)=0.33.
m.p.=179-180° C.
IR (KBr): ν=3352, 3209, 2929, 1727, 1648, 1609, 1559, 1490, 1426, 1371, 1308, 1285, 1258, 1154, 1031, 929 $cm^{-1}$.
$^1$H NMR (300 MHz, $CDCl_3$): δ=0.99 (t, J=7.2 Hz, 3H, $H_{18}$), 1.88-1.93 (m, 1H, $H_{10}$), 2.02-2.08 (m, 2H, $H_{10}$, $H_{13}$), 2.57 (dd, J=17.1 Hz, J=3.9 Hz, 1H, $H_{13}$), 2.70-2.74 (m, 1H, $H_7$), 2.72-2.77 (m, 2H, $H_{14}$), 2.94 (d, J=17.7 Hz, 1H, $H_6$), 3.11 (dd, J=17.5 Hz, J=5.5 Hz, 1H, $H_6$), 3.16-3.20 (m, 1H, $H_{11}$), 3.92 (q, J=7.1 Hz, 2H, $H_{17}$), 5.05 (brs, 2H, $NH_2$), 5.67 (d, J=5.1 Hz, 1H, $H_8$), 7.21 (dd, J=9.0 Hz, J=1.9 Hz, 1H, $H_2$), 7.65 (d, J=9.0 Hz, 1H, $H_1$), 7.81 (d, J=1.9 Hz, 1H, $H_4$).
$^{13}$C NMR (75 MHz, $CDCl_3$): δ=14.0 ($C_{18}$), 27.4 ($C_{11}$), 28.4 ($C_7$), 28.8 ($C_{10}$), 33.9 ($C_{13}$), 39.2 ($C_6$), 43.3 ($C_{14}$), 60.6 ($C_{17}$), 114.9 ($C_{11a}$ or $C_{12a}$), 115.8 ($C_{11a}$ or $C_{12a}$), 121.9 ($C_1$), 124.7 ($C_2$), 127.1 ($C_4$), 129.5 ($C_8$), 129.8 ($C_9$), 134.6 ($C_3$), 146.4 ($C_{4a}$ or $C_{12}$), 146.9 ($C_{4a}$ or $C_{12}$), 158.1 ($C_{5a}$), 171.5 ($C_{15}$).
MS (ESI+): m/z (%): 357.33 (100) $[M+H]^+$, 359.20 (36).
$IC_{50}$ rh-AChE: 3.90±0.50 nM.
$IC_{50}$ rh-BuChE: 137±11 nM.
$IC_{50}$ erythrocyte h-AChE: 38.3 nM.

EXAMPLE 2

2-(12-Amino-3-chloro-6,7,10,11-tetrahydro-7,11-methanocycloocta[b]quinolin-9-yl) Ethanol (HUP 2)

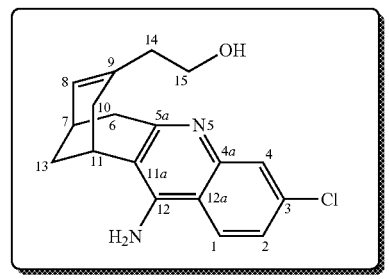

$C_{18}H_{19}ClN_2O$
Mol. Wt.: 314.81

To a cooled (0° C.) stirred suspension of anhydrous $LiAlH_4$ (400 mg, 10 mmol) in dry THF (50 mL) was added dropwise a solution of ester (HUP 1) (1.78 g, 5.0 mmol) in dry THF (15 mL). The solution was stirred 1 h (0° C. to r.t.) then quenched carefully at 0° C. by the addition of water (1.75 mL), then 5 M NaOH solution (1.75 mL), then water (5 mL). The reaction mixture was stirred 10 min at r.t. then dried with $Na_2SO_4$. Filtration and concentration afforded the desired Huprine (HUP 2) as a very pale yellow solid (1.60 g, quantitative). Recrystallisation from acetone afforded a white solid.

Rf (AcOEt/MeOH 8/2, v/v)=0.15.
m.p.=174° C. (decomposition).
IR (KBr): ν=3352, 3252, 2894, 1645, 1609, 1573, 1490, 1424, 1373, 1309, 1285, 1046, 928, 818, 770 $cm^{-1}$.
$^1$H NMR (300 MHz, MeOD): δ=1.84-1.89 (m, 1H, $H_{10}$), 2.00-2.06 (m, 4H, $H_{10}$, $H_{13}$, $H_{14}$), 2.49 (dd, J=17.3 Hz, J=4.1 Hz, 1H, $H_{13}$), 2.65-2.69 (m, 1H, $H_7$), 2.82 (d, J=17.5 Hz, 1H, $H_6$), 3.02 (dd, J=17.5 Hz, J=5.6 Hz, 1H, $H_6$), 3.27-3.31 (m, 1H, $H_{11}$), 3.46 (t, J=7.0 Hz, 2H, $H_{15}$), 5.57 (d, J=4.9 Hz, 1H, $H_8$), 7.23 (dd, J=9.0 Hz, J=1.9 Hz, 1H, $H_2$), 7.64 (d, J=1.9 Hz, 1H, $H_4$), 7.99 (d, J=9.0 Hz, 1H, $H_1$).

$^{13}$C NMR (75 MHz, MeOD): δ=28.3 ($C_{11}$), 29.6 ($C_7$), 30.2 ($C_{10}$), 35.2 ($C_{13}$), 40.2 ($C_6$), 42.6 ($C_{14}$), 61.5 ($C_{15}$), 115.5 ($C_{11a}$ or $C_{12a}$), 117.1 ($C_{11a}$ or $C_{12a}$), 124.6 ($C_1$), 124.8 ($C_2$), 126.3 ($C_4$), 127.3 ($C_8$), 135.0 ($C_3$), 135.5 ($C_9$), 148.0 ($C_{4a}$ or $C_{12}$), 150.0 ($C_{4a}$ or $C_{12}$), 159.2 ($C_{5a}$).

MS (ESI+): m/z (%): 315.27 (100) [M+H]$^+$, 317.27 (35).

$IC_{50}$ rh-AChE: 1.05±0.13 nM.

$IC_{50}$ rh-BuChE: 1240 nM.

$IC_{50}$ erythrocyte h-AChE: 6.15 nM.

EXAMPLE 3

3-Chloro-9-vinyl-6,7,10,11-tetrahydro-7,11-methanocycloocta[b]quinolin-12-amine Trifluoroacetic Acid (HUP 3)

$C_{20}H_{18}ClF_3N_2O_2$
Mol. Wt.: 410.82

To a partially soluble suspension of iodinated compound (HUP 7) (71 mg, 0.167 mmol) in MeCN (2 mL) was added a solution of 1 M trimethylamine in THF (1.7 mL, 1.67 mmol), and the mixture was heated to 55° C. for 13 h. The reaction mixture was concentrated to dryness then purified by preparative HPLC (System A) and freeze dried to afford the di-trifluoroacetate salt of the desired Huprine (HUP 3) as a white solid (37.7 mg, 55%) along with quaternary ammonium (HUP 25) (26.3 mg, 27%) as substitution byproduct.

Rf (AcOEt/MeOH 8/2, v/v)=0.38.

m.p.=150° C. (decomposition).

$^1$H NMR (300 MHz, MeOD): δ=1.98-2.04 (m, 1H, $H_{10}$), 2.09-2.16 (m, 1H, $H_{10}$), 2.31-2.37 (m, 1H, $H_{13}$), 2.53-2.62 (m, 1H, $H_{13}$), 2.88-2.97 (m, 2H, $H_7$, $H_6$), 3.23-3.29 (m, 1H, $H_6$), 3.46-3.49 (m, 1H, $H_{11}$), 4.86-4.91 (m, 1H, $H_{15}$), 5.09 (d, J=17.5 Hz, 1H, $H_{15}$), 5.90 (d, J=5.5 Hz, 1H, $H_8$), 6.30 (dd, J=17.5 Hz, J=10.7 Hz, 1H, $H_{14}$), 7.56 (dd, J=9.0 Hz, J=1.5 Hz, 1H, $H_2$), 7.71 (d, J=1.5 Hz, 1H, $H_4$), 8.34 (d, J=9.0 Hz, 1H, $H_1$).

$^{13}$C NMR (75 MHz, MeOD): δ=26.9 ($C_{11}$), 28.4 ($C_7$), 29.4 ($C_{10}$), 29.9 ($C_{13}$), 35.4 ($C_6$), 112.1 ($C_{15}$), 115.2 ($C_{11a}$ or $C_{12a}$), 115.3 ($C_{11a}$ or $C_{12a}$), 119.2 ($C_4$), 126.3 ($C_1$), 127.7 ($C_2$), 132.1 ($C_8$), 136.5 ($C_3$), 139.5 ($C_9$), 140.3 ($C_{14}$), 140.5 ($C_{4a}$ or $C_{12}$), 152.7 ($C_{4a}$ or $C_{12}$), 156.8 ($C_{5a}$).

MS (ESI+): m/z (%): 297.33 (100) [M+H]$^+$, 299.26 (32).

$IC_{50}$ rh-AChE: 1.32±0.17 nM.

$IC_{50}$ rh-BuChE: 180±13 nM.

$IC_{50}$ erythrocyte h-AChE: 405 nM.

EXAMPLE 4

2-(12-Amino-3-chloro-6,7,10,11-tetrahydro-7,11-methanocycloocta[b]quinolin-9-yl)ethyl Acetate (HUP 4)

$C_{20}H_{21}ClN_2O_2$
Mol. Wt.: 356.85

To a cooled to 0° C. solution of alcohol (HUP 2) (78.5 mg, 0.25 mmol) and triethylamine (840 μL, 6 mmol) in THF (4 mL) was added dropwise acetic anhydride (570 μL, 6 mmol) and the resulting suspension was stirred at reflux for 21 h. The reaction mixture was partionned between 2 M aqueous HCl solution (12 mL) and AcOEt (15 mL). The aqueous phase was extracted with AcOEt (2×15 mL). The combined organic layers were dried with $Na_2SO_4$ and concentrated under reduced pressure to afford a brown residue. Purification by flash chromatography (AcOEt/MeOH 10/0 to 8.5/1.5 v/v) to afford the desired Huprine (HUP 4) as a white solid (16 mg, 18%) along with tri-acylated product N,N-diacyl-HUP 4 (66 mg, 60%).

Rf (AcOEt/MeOH 8/2, v/v)=0.45.

m.p.=97° C. (decomposition).

$^1$H NMR (300 MHz, CDCl$_3$): δ=1.80 (s, 3H, Ac), 1.89-2.00 (m, 3H, $H_{10}$, $H_{13}$), 2.05-2.12 (m, 2H, $H_{14}$), 2.45 (dd, J=17.3 Hz, J=4.3 Hz, 1H, $H_{13}$), 2.72-2.76 (m, 1H, $H_7$), 2.93 (d, J=17.7 Hz, 1H, $H_6$), 3.05-3.15 (m, 2H, $H_6$, $H_{11}$), 3.91-3.99 (m, 2H, $H_{15}$), 5.55 (d, J=5.3 Hz, 1H, $H_8$), 5.71 (brs, 2H, $NH_2$), 7.23 (dd, J=9.0 Hz, J=1.9 Hz, 1H, $H_2$), 7.77 (d, J=9.0 Hz, 1H, $H_1$), 7.81 (d, J=1.9 Hz, 1H, $H_4$).

$^{13}$C NMR (75 MHz, CDCl$_3$): δ=20.8 (Ac), 27.1 ($C_{11}$), 27.9 ($C_7$), 28.8 ($C_{10}$), 33.6 ($C_{13}$), 36.4 ($C_{14}$), 37.9 ($C_6$), 62.4 ($C_{15}$), 114.5 ($C_{11a}$ or $C_{12a}$), 115.3 ($C_{11a}$ or $C_{12a}$), 122.8 ($C_1$), 124.8 ($C_2$), 125.1 ($C_4$), 127.2 ($C_8$), 132.6 ($C_3$), 135.6 ($C_9$), 144.4 ($C_{4a}$ or $C_{12}$), 148.3 ($C_{4a}$ or $C_{12}$), 156.4 ($C_{5a}$), 171.0 (C=O).

MS (ESI+): m/z (%): 357.27 (100) [M+H]$^+$, 359.20 (36).

$IC_{50}$ rh-AChE: 1.44±0.18 nM.

$IC_{50}$ rh-BuChE: 37% at 1 μM.

$IC_{50}$ erythrocyte h-AChE: 12.0 nM.

EXAMPLE 5

2-[3-Chloro-12-(diacetylamino)-6,7,10,11-tetrahydro-7,11-methano cycloocta[b]quinolin-9-yl]ethyl Acetate (N,N-diacyl-HUP 4)

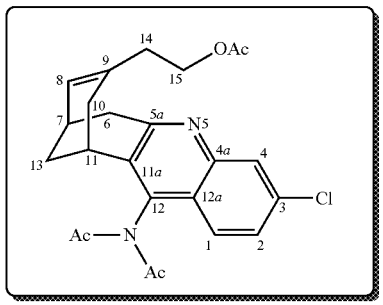

$C_{24}H_{25}ClN_2O_4$
Mol. Wt.: 440.92

To a cooled to 0° C. solution of alcohol (HUP 2) (78.5 mg, 0.25 mmol) and triethylamine (840 µL, 6 mmol) in THF (4 mL) was added dropwise acetic anhydride (570 µL, 6 mmol) and the resulting suspension was stirred at reflux for 21 h. The reaction mixture was partionned between 2 M aqueous HCl solution (12 mL) and AcOEt (15 mL). The aqueous phase was extracted with AcOEt (2×15 mL). The combined organic layers were dried with $Na_2SO_4$ and concentrated under reduced pressure to afford a brown residue. Purification by flash chromatography (cyclohexane/AcOEt/MeOH 7/3/0 to 0/8.5/1.5 with a 1% $Et_3N$, v/v) afforded the desired Huprine as a pale yellow solid (66 mg, 60%) along with mono-acylated product (HUP 4) (16 mg, 18%).

Rf (AcOEt)=0.85.

m.p.=50° C. (decomposition).

$^1$H NMR (300 MHz, $CDCl_3$): δ=1.79-1.90 (m, 2H, $H_{10}$, $H_{13}$), 1.86 (s, 3H, OAc), 2.07 (s, 3H, NAc), 2.07-2.10 (m, 3H, $H_{10}$, $H_{14}$), 2.44-2.53 (m, 1H, $H_{13}$), 2.52 (s, 3H, NAc), 2.80-2.85 (m, 1H, $H_7$), 3.18-3.28 (m, 3H, $H_6$, $H_{11}$), 3.91-3.99 (m, 2H, $H_{15}$), 5.63 (d, J=4.7 Hz, 1H, $H_8$), 7.44-7.45 (m, 2H, $H_2$, $H_1$), 8.03-8.04 (m, 1H, $H_4$).

$^{13}$C NMR (75 MHz, $CDCl_3$): δ=20.9 (OAc), 25.9 (NAc), 27.0 (NAc), 28.1 ($C_7$), 28.5 ($C_{10}$), 29.2 ($C_{11}$), 34.6 ($C_{13}$), 36.1 ($C_{14}$), 40.3 ($C_6$), 62.3 ($C_{15}$), 123.0 (3C, $C_{11a}$, $C_{12a}$, $C_1$), 127.4 ($C_8$), 128.2 ($C_4$), 128.5 ($C_2$), 132.0 ($C_3$), 133.1 ($C_9$), 141.9 ($C_{4a}$ or $C_{12}$), 148.2 ($C_{4a}$ or $C_{12}$), 161.2 ($C_{5a}$), 171.0 (C=O), 172.1 (C=O), 173.0 (C=O).

MS (ESI+): m/z (%): 441.16 (100) [M+H]$^+$, 443.09 (33), 399.25 (15).

EXAMPLE 6

2-(12-Amino-3-chloro-6,7,10,11-tetrahydro-7,11-methanocycloocta[b]quinolin-9-yl)ethyl Trifluoroacetate (HUP 5)

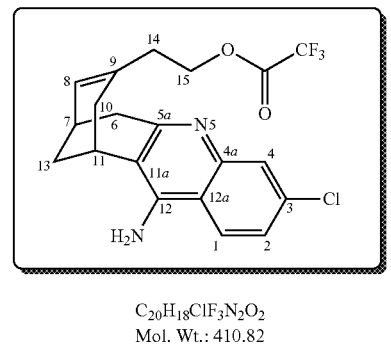

$C_{20}H_{18}ClF_3N_2O_2$
Mol. Wt.: 410.82

To a cooled to 0° C. solution of alcohol (HUP 2) (78.5 mg, 0.25 mmol) and triethylamine (53 µL, 0.375 mmol) in THF (4 mL) was added dropwise trifluoroacetic anhydride (52 µL, 0.375 mmol). The solution was stirred 40 min at r.t. The reaction mixture was concentrated under reduced pressure to dryness then partionned between 2M aqueous HCl solution (12 mL) and AcOEt (12 mL). The aqueous phase was extracted with AcOEt (3×15 mL). The combined organic layers were dried with $Na_2SO_4$ and concentrated under reduced pressure to afford a yellow solid. Purification by flash chromatography (cyclohexane/AcOEt 7/3, v/v) afforded the desired Huprine (HUP 5) as a white solid (85 mg, 83%).

Rf (cyclohexane/AcOEt 1/1, v/v)=0.59.

m.p.=124° C. (decomposition).

$^1$H NMR (300 MHz, MeOD): δ=1.98-2.08 (m, 3H, $H_{10}$, $H_{13}$), 2.23-2.30 (m, 2H, $H_{14}$), 2.63 (dd, J=17.4 Hz, J=4.8 Hz, 1H, $H_{13}$), 2.11-2.17 (m, 1H, $H_7$), 3.17 (d, J=18.3 Hz, 1H, $H_6$), 3.39 (dd, J=18.3 Hz, J=5.3 Hz, 1H, $H_6$), 3.58-3.64 (m, 1H, $H_{11}$), 4.23-4.31 (m, 2H, $H_{15}$), 5.69 (d, J=5.1 Hz, 1H, $H_8$), 7.72 (dd, J=9.0 Hz, J=1.7 Hz, 1H, $H_2$), 7.97 (d, J=9.0 Hz, 1H, $H_1$), 8.05 (d, J=1.7 Hz, 1H, $H_4$).

$^{13}$C NMR (75 MHz, MeOD): δ=28.4 ($C_{10}$), 28.5 ($C_7$), 29.8 ($C_{11}$), 35.8 ($C_{13}$), 37.0 ($C_{14}$), 38.5 ($C_6$), 66.5 ($C_{15}$), 116.8 (q, J=140.2 Hz, $CF_3$), 123.3 ($C_4$), 124.5 ($C_{11a}$ or $C_{12a}$), 126.6 ($C_1$), 129.3 ($C_8$), 130.3 ($C_2$), 133.6 ($C_{11a}$ or $C_{12a}$), 135.0 ($C_3$), 139.6 ($C_9$), 143.5 ($C_{4a}$ or $C_{12}$), 146.6 ($C_{4a}$ or $C_{12}$), 158.1 ($C_{5a}$), 160.9 (C=O).

$^{19}$F NMR (282 MHz, MeOD): −77.13, −76.75, −76.31.

MS (ESI+): m/z (%): 315.40 (100) [M+H—$COCF_3$]$^+$, 317.33 (37).

$IC_{50}$ rh-AChE: 1.69±0.16 nM.

$IC_{50}$ rh-BuChE: 1360 nM.

$IC_{50}$ erythrocyte h-AChE: 27.5 nM.

EXAMPLE 7

3-Chloro-9-(2-methoxyethyl)-6,7,10,11-tetrahydro-7,11-methanocycloocta[b]quinolin-12-amine (HUP 6)

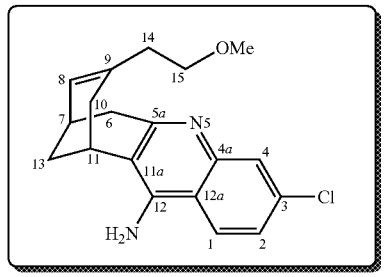

$C_{19}H_{21}ClN_2O$
Mol. Wt.: 328.84

To a solution of sodium pieces (about 50 mg, degreased in $Et_2O$) in MeOH (25 mL) was added at 0° C. dropwise over 5 min a solution of alcohol (HUP 2) (118 mg, 0.3 mmol) in MeOH (5 mL). The resulting solution was stirred 1 h at r.t., then at reflux for 24 h without change in TLC and $^1$H NMR. Water (3 mL) was added and the reaction mixture was concentrated to remove the methanol. The residue was partitioned between AcOEt and water (20 mL of each) and the aqueous phase was extracted with AcOEt (2×15 mL). The combined organic layers were dried with $Na_2SO_4$ and concentrated under reduced pressure to afford a yellow solid. Purification by flash chromatography (AcOEt/MeOH 100/0 to 85/15, v/v) afforded the desired Huprine (HUP 6) as a white solid (43.1 mg, 44%) along with alkene (HUP 3) (6.9 mg, 7.7%) as β-elimination by-product.

Rf (AcOEt/MeOH 8/2, v/v)=0.31.

m.p.=124° C. (decomposition).

IR (KBr): ν=3364, 3248, 2928, 1645, 1609, 1560, 1490, 1425, 1371, 1309, 1285, 1217, 1184, 1154, 1110, 928, 756 cm$^{-1}$.

$^1$H NMR (300 MHz, MeOD): δ=1.89-1.94 (m, 1H, $H_{10}$), 2.03-2.09 (m, 4H, $H_{10}$, $H_{13}$, $H_{14}$), 2.48 (dd, J=18.5 Hz, J=5.5 Hz, 1H, $H_{13}$), 2.69-2.73 (m, 1H, $H_7$), 2.83 (d, J=17.5 Hz, 1H, $H_6$), 3.06 (dd, J=17.5 Hz, J=5.5 Hz, 1H, $H_6$), 3.13 (s, 3H, MeO), 3.26-3.33 (m, 3H, $H_{11}$, $H_{15}$), 5.58 (d, J=5.5 Hz, 1H, $H_8$), 7.30 (dd, J=9.0 Hz, J=1.9 Hz, 1H, $H_2$), 7.66 (d, J=1.9 Hz, 1H, $H_4$), 8.06 (d, J=9.0 Hz, 1H, $H_1$).

$^{13}$C NMR (75 MHz, MeOD): δ=28.3 ($C_{11}$), 29.6 ($C_7$), 30.2 ($C_{10}$), 35.0 ($C_{13}$), 38.4 ($C_{14}$), 39.8 ($C_6$), 58.7 (MeO), 72.3 ($C_{15}$), 115.6 ($C_{11a}$ or $C_{12a}$), 117.0 ($C_{11a}$ or $C_{12a}$), 124.9 ($C_1$), 125.3 ($C_2$), 125.6 ($C_4$), 127.2 ($C_8$), 135.4 ($C_3$), 136.2 ($C_9$), 147.2 ($C_{4a}$ or $C_{12}$), 150.8 ($C_{4a}$ or $C_{12}$), 158.7 ($C_{5a}$).

MS (ESI+): m/z (%): 329.33 (100) [M+H]$^+$, 331.26 (37).

IC$_{50}$ rh-AChE: 1.75±0.21 nM.

IC$_{50}$ rh-BuChE: 401±26 nM.

IC$_{50}$ erythrocyte h-AChE: 4.50 nM.

EXAMPLE 8

3-Chloro-9-(2-iodoethyl)-6,7,10,11-tetrahydro-7,11-methanocycloocta[b]quinolin-12-amine (HUP 7)

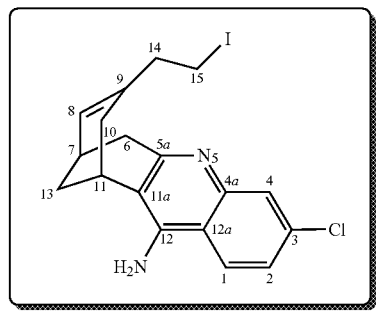

$C_{18}H_{18}ClIN_2$
Mol. Wt.: 424.71

To a stirred suspension of sodium iodide (1.35 g, 9 mmol) in acetone (10 mL) was added mesylate (HUP 13) (648 mg, 1.65 mmol) in acetone (7 mL). The reaction mixture was stirred at reflux for 12 h. The mesylate salts were filtered and the filtrate was concentrated under reduced pressure to give a yellow solid. This solid was redissolved acetone/AcOEt mixtures to precipitate the excess of sodium iodide. Filtration of the salts and evaporation of the filtrate afford the desired Huprine (HUP 7) as a pale yellow solid (378 mg, 54%) along with alkene (HUP 3) (64 mg, 13%) as β-elimination by-product.

Rf (AcOEt/MeOH 8/2, v/v)=0.40.

m.p.=111° C. (decomposition).

$^1$H NMR (300 MHz, MeOD): δ=1.84-2.03 (m, 3H, $H_{10}$, $H_{13}$), 2.26-2.33 (m, 2H, $H_{14}$), 2.43 (dd, J=21.3 Hz, J=4.7 Hz, 1H, $H_{13}$), 2.67-2.72 (m, 1H, $H_7$), 2.85 (d, J=17.5 Hz, 1H, $H_6$), 3.00-3.07 (m, 2H, $H_6$, $H_{11}$), 3.18-3.23 (m, 2H, $H_{15}$), 5.58 (d, J=4.9 Hz, 1H, $H_8$), 7.26 (dd, J=8.9 Hz, J=2.1 Hz, 1H, $H_2$), 7.64 (d, J=2.1 Hz, 1H, $H_4$), 8.02 (d, J=8.9 Hz, 1H, $H_1$).

MS (ESI+): m/z (%): 425.20 (100) [M+H]$^+$, 427.13 (32), 297.27 (17).

IC$_{50}$ rh-AChE: 2.70±0.82 nM.

IC$_{50}$ rh-BuChE: 141±7 nM.

EXAMPLE 9

3-(12-Amino-3-chloro-6,7,10,11-tetrahydro-7,11-methanocycloocta[b]quinolin-9-yl)propanenitrile Trifluoroacetic Acid (HUP 8)

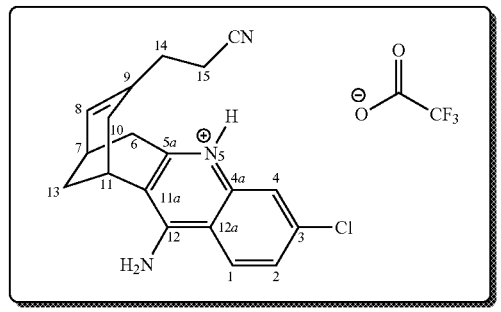

$C_{21}H_{19}ClF_3N_3O_2$
Mol. Wt.: 437.84

To a solution of mesylate (HUP 13) (98 mg, 0.25 mmol) was added a partially soluble suspension of potassium cyanide (81.4 mg, 1.25 mmol) and TBAI (30 mg, 0.3 mmol) in a MeCN/DMF/DMSO mixture (6 mL/3 mL/2 mL). The resulting suspension was stirred 5 h at 70° C. The reaction mixture was concentrated to dryness then purified by preparative HPLC (System A) and freeze dried to afford the trifluoroacetate salt of the desired Huprine (HUP 8) as a white solid (62.2 mg, 57%).

m.p.=127° C. (decomposition).

$^1$H NMR (300 MHz, MeOD): δ=1.91-2.15 (m, 3H, $H_{10}$, $H_{13}$), 2.16-2.21 (t, J=6.9 Hz, 2H, $H_{14}$), 2.44 (td, J=7.2 Hz, J=2.1 Hz, 2H, $H_{15}$), 2.56 (dd, J=21.3 Hz, J=5.5 Hz, 1H, $H_{13}$), 2.85-2.94 (m, 2H, $H_7$, $H_6$), 3.19-3.26 (m, 1H, $H_6$), 3.41-3.45 (m, 1H, $H_{11}$), 5.75 (d, J=4.3 Hz, 1H, $H_8$), 7.56 (dd, J=9.0 Hz, J=1.5 Hz, 1H, $H_2$), 7.71 (d, J=1.5 Hz, 1H, $H_4$), 8.34 (d, J=9.0 Hz, 1H, $H_1$).

$^{13}$C NMR (75 MHz, MeOD): δ=16.4 ($C_{15}$), 27.4 ($C_{11}$), 28.2 ($C_7$), 29.1 ($C_{10}$), 33.1 ($C_{14}$), 33.4 ($C_{13}$), 35.8 ($C_6$), 115.1 ($C_{11a}$ or $C_{12a}$), 115.4 ($C_{11a}$ or $C_{12a}$), 119.3 ($C_4$), 120.3 (CN), 126.4 ($C_1$), 127.7 ($C_2$), 127.8 ($C_8$), 135.7 ($C_3$), 139.6 ($C_9$), 140.4 ($C_{4a}$ or $C_{12}$), 153.0 ($C_{4a}$ or $C_{12}$), 156.8 ($C_{5a}$).

MS (ESI+): m/z (%): 324.27 (100) [M+H]$^+$, 326.27 (38).

IC$_{50}$ rh-AChE: 3.15±0.42 nM.
IC$_{50}$ rh-BuChE: 514±58 nM.

EXAMPLE 10

3-Chloro-9-(2-chloroethyl)-6,7,10,11-tetrahydro-7,11-methanocycloocta[b]quinolin-12-amine Trifluoroacetic Acid (HUP 9)

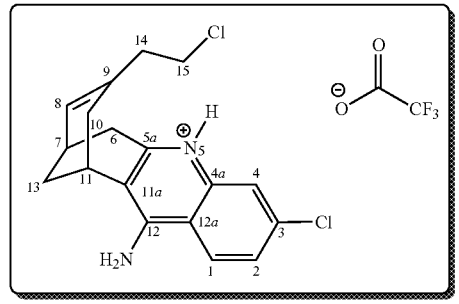

$C_{20}H_{19}Cl_2F_3N_2O_2$
Mol. Wt.: 447.28

To a partially soluble suspension of alcohol (HUP 2) (63 mg, 0.2 mmol) in AcOEt (10 mL) cooled to 0° C. was added dropwise thionyl chloride (300 μL, 4.14 mmol). The reaction mixture was stirred 14 h at 60° C., then concentrated to dryness. The residue was purified by preparative HPLC (System A) and freeze dried to afford the trifluoroacetate salt of the desired Huprine (HUP 9) as a white solid (22.0 mg, 25%).

Rf (AcOEt/MeOH 8/2, v/v)=0.44 (free base).

m.p.=132° C. (decomposition).

$^1$H NMR (300 MHz, MeOD): δ=1.96-2.13 (m, 3H, $H_{10}$, $H_{13}$), 2.28-2.34 (m, 2H, $H_{14}$), 2.53 (dd, J=17.2 Hz, J=4.5 Hz, 1H, $H_{13}$), 2.84-2.92 (m, 2H, $H_{11}$, $H_6$), 3.18-3.25 (m, 1H, $H_6$), 4.06-4.10 (m, 1H, $H_7$), 3.49 (t, J=6.7 Hz, 2H, $H_{15}$), 5.69 (d, J=4.3 Hz, 1H, $H_8$), 7.57 (dd, J=9.0 Hz, J=1.7 Hz, 1H, $H_2$), 7.74 (d, J=1.7 Hz, 1H, $H_4$), 8.34 (d, J=9.0 Hz, 1H, $H_1$).

$^{13}$C NMR (75 MHz, MeOD): δ=27.5 ($C_7$), 28.3 ($C_7$), 29.2 ($C_{10}$), 33.6 ($C_{13}$), 35.9 ($C_6$), 40.9 ($C_{14}$), 43.6 ($C_{15}$), 115.3 ($C_{11a}$ or $C_{12a}$), 115.4 ($C_{11a}$ or $C_{12a}$), 119.3 ($C_4$), 126.4 ($C_1$), 127.7 ($C_2$), 127.9 ($C_8$), 135.3 ($C_3$), 139.7 ($C_9$), 140.5 ($C_{4a}$ or $C_{12}$), 153.1 ($C_{4a}$ or $C_{12}$), 156.8 ($C_{5a}$).

MS (ESI+): m/z (%): 333.33 (100) [M+H]$^+$, 335.20 (62), 337.20 (12).

IC$_{50}$ rh-AChE: 3.56±0.20 nM.
IC$_{50}$ rh-BuChE: 207±12 nM.
IC$_{50}$ erythrocyte h-AChE: 5.09 nM.

EXAMPLE 11

3-Chloro-9-(2-fluoroethyl)-6,7,10,11-tetrahydro-7,11-methanocycloocta[b]quinolin-12-amine (HUP 10)

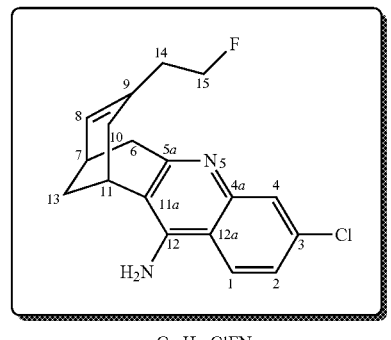

$C_{18}H_{20}ClFN_2$
Mol. Wt.: 316.80

To a partially soluble suspension of alcohol (HUP 2) (157 mg, 0.5 mmol) cooled to −78° C. was added dropwise DAST (75 μL, 0.6 mmol). The resulting suspension was stirred 1 h at r.t., after which the solubility proved total. The reaction mixture was cooled again to −78° C. and MeOH (200 μL) was added. The solution was additionally stirred for 30 min at r.t. then quenched by saturated solution of NaHCO$_3$ and extracted with AcOEt (2×15 mL) and DCM (15 mL). The combined organic layers were dried with Na$_2$SO$_4$ and concentrated under reduced pressure to afford a yellow solid (132 mg). Purification by flash chromatography (AcOEt/MeOH 100/0 to 90/10, v/v) afforded the desired Huprine (HUP 10) as a white solid (78 mg, 49%).

Rf (AcOEt/MeOH 8/2, v/v)=0.56.

m.p.=110° C. (decomposition).

$^1$H NMR (300 MHz, MeOD): δ=1.91-1.94 (m, 1H, $H_{10}$), 2.01-2.20 (m, 4H, $H_{10}$, $H_{13}$, $H_{14}$), 2.52 (dd, J=17.9 Hz, J=5.5 Hz, 1H, $H_{13}$), 2.69-2.73 (m, 1H, $H_7$), 2.84 (d, J=18.2 Hz, 1H, $H_6$), 3.06 (dd, J=17.5 Hz, J=5.5 Hz, 1H, $H_6$), 3.33-3.37 (m, 1H, $H_{11}$), 4.12 (td, J=47.5 Hz, J=6.3 Hz, 2H, $H_{15}$), 5.63 (d, J=5.5 Hz, 1H, $H_8$), 7.29 (dd, J=1.9 Hz, J=9.0 Hz, 1H, $H_2$), 7.65 (d, J=1.9 Hz, 1H, $H_4$), 8.05 (d, J=9.0 Hz, 1H, $H_1$).

$^{13}$C NMR (75 MHz, MeOD): δ=28.2 ($C_{11}$), 29.5 ($C_7$), 30.0 ($C_{10}$), 35.1 ($C_{13}$), 39.3 (d, $C_{14}$, J=20.3 Hz), 39.6 ($C_6$), 83.2 (d, $C_{15}$, J=165.8 Hz), 115.5 ($C_{11a}$ or $C_{12a}$), 116.9 ($C_{11a}$ or $C_{12a}$), 124.9 ($C_1$), 125.3 ($C_2$), 125.5 ($C_4$), 128.1 ($C_8$), 134.2 ($C_3$), 136.2 ($C_9$), 147.1 ($C_{4a}$ or $C_{12}$), 150.8 ($C_{4a}$ or $C_{12}$), 158.4 ($C_{5a}$).

$^{19}$F NMR (282 MHz, MeOD): δ=−76.9.

MS (ESI+): m/z (%): 317.36 (100) [M+H]$^+$, 319.22 (37), 320.15 (11).

IC$_{50}$ rh-AChE: 4.16±0.79 nM.
IC$_{50}$ rh-BuChE: 522±120 nM.

EXAMPLE 12

12-Amino-3-chloro-9-carboxymethyl-6,7,10,11-tetrahydro-7,11 methanocycloocta[b]quinoline Hydrochloride (HUP 11)

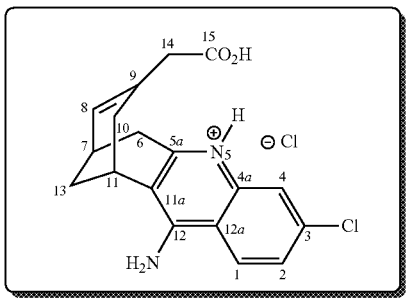

$C_{18}H_{18}Cl_2N_2O_2$
Mol. Wt.: 365.25

A suspension of alcohol (HUP 2) (166 mg, 0.47 mmol) in DMF (2 mL) and 2 M NaOH solution (23 mL) was heated at reflux for 6 h30. The reaction mixture was then cooled to r.t. and acidified with 2 M aqueous HCl solution (30 mL). The white crystals which appeared in the solution were filtered and dried at air to afford the hydrochloride of the desired Huprine (HUP 11) as a white solid (170 mg, 99%).

m.p.=148° C. (decomposition).
IR (KBr): ν=3342, 3236, 2933, 1713, 1657, 1588, 1468, 1415, 1375, 1229, 1155, 1084, 933 cm$^{-1}$.
$^1$H NMR (300 MHz, MeOD): δ=1.96-2.01 (m, 1H, $H_{10}$), 2.09-2.19 (m, 2H, $H_{10}$, $H_{13}$), 2.59 (dd, J=17.7 Hz, J=3.8 Hz, 1H, $H_{13}$,), 2.84-2.96 (m, 4H, $H_7$, $H_{14}$, $H_6$), 3.24 (dd, J=18.1 Hz, J=5.5 Hz, 1H, $H_6$), 3.39-3.43 (m, 1H, $H_{11}$), 5.74 (d, J=4.5 Hz, 1H, $H_8$), 7.60 (dd, J=9.0 Hz, J=1.9 Hz, 1H, $H_2$), 7.74 (d, J=1.9 Hz, 1H, $H_4$), 8.35 (d, J=9.0 Hz, 1H, $H_1$).
$^{13}$C NMR (75 MHz, MeOD): δ=27.5 ($C_{11}$), 28.3 ($C_7$), 28.9 ($C_{10}$), 34.1 ($C_{13}$), 35.7 ($C_6$), 43.4 ($C_{14}$), 115.3 ($C_{11a}$ or $C_{12a}$), 115.4 ($C_{11a}$ or $C_{12a}$), 119.2 ($C_4$), 126.5 ($C_1$), 127.7 ($C_2$), 129.1 ($C_8$), 132.9 ($C_3$), 139.6 ($C_9$), 140.4 ($C_{4a}$ or $C_{12}$), 152.9 ($C_{4a}$ or $C_{12}$), 156.8 ($C_{5a}$), 175.2 ($C_{15}$).
MS (ESI+): m/z (%): 329.33 (100) [M+H]$^+$, 331.27 (31).
HPLC: tr=14.4 (purity 93%).
$IC_{50}$ rh-AChE: 5.30±1.10 nM.
$IC_{50}$ rh-BuChE: <1% at 1 μM.

EXAMPLE 13

9-(2-Azidoethyl)-3-chloro-6,7,10,11-tetrahydro-7,11-methanocycloocta[b]quinolin-12-amine (HUP 12)

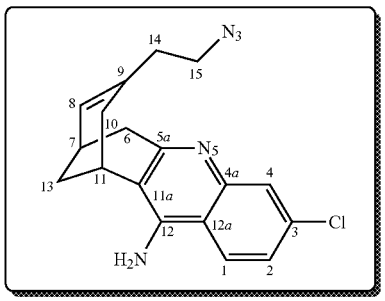

$C_{18}H_{18}ClN_5$
Mol. Wt.: 339.82

A suspension of mesylate (HUP 13) (236 mg, 0.6 mmol) and sodium azide (146 mg, 2.25 mmol) in dry DMF (3 mL) was stirred under argon at 70° C. for 6 h. The reaction mixture was then cooled to r.t. and water (5 mL) was added under stirring. Additional water (25 mL) was added. Aqueous phase was extracted with AcOEt (3×30 mL) and the combined organic layers were dried with $Na_2SO_4$ and concentrated to afford a yellow oil. Purification by flash chromatography (AcOEt/MeOH 100/0 to 95/5, v/v) afforded the desired Huprine (HUP 12) as a pale yellow solid (172 mg, 84%).

Rf (AcOEt/MeOH 9/1, v/v)=0.63.
m.p.=106° C. (decomposition).
$^1$H NMR (300 MHz, MeOD): δ=1.88-1.92 (m, 1H, $H_{10}$), 2.01-2.10 (m, 4H, $H_{10}$, $H_{13}$, $H_{14}$), 2.48 (dd, J=17.3 Hz, J=4.1 Hz, 1H, $H_{13}$,), 2.68-2.72 (m, 1H, $H_7$), 2.84 (d, J=17.3 Hz, 1H, $H_6$), 3.04 (dd, J=17.3 Hz, J=5.5 Hz, 1H, $H_6$), 3.15 (td, J=7.0 Hz, J=3.6 Hz, 2H, $H_{15}$), 3.29-3.33 (m, 1H, $H_{11}$), 5.64 (d, J=5.5 Hz, 1H, $H_8$), 7.25 (dd, J=9.0 Hz, J=1.9 Hz, 1H, $H_2$), 7.65 (d, J=1.9 Hz, 1H, $H_4$), 8.02 (d, J=9.0 Hz, 1H, $H_1$).
$^{13}$C NMR (75 MHz, MeOD): δ=28.2 ($C_{11}$), 29.7 ($C_7$), 30.0 ($C_{10}$), 34.6 ($C_{13}$), 37.7 ($C_{14}$), 39.9 ($C_6$), 50.4 ($C_{15}$), 115.3 ($C_{11a}$ or $C_{12a}$), 117.0 ($C_{11a}$ or $C_{12a}$), 124.7 ($C_1$), 124.9 ($C_2$), 126.1 ($C_4$), 128.4 ($C_8$), 134.7 ($C_3$), 135.7 ($C_9$), 147.9 ($C_{4a}$ or $C_{12}$), 150.2 ($C_{4a}$ or $C_{12}$), 158.9 ($C_{5a}$).
MS (ESI+): m/z (%): 340.11 (100) [M+H]$^+$, 342.11 (34).
$IC_{50}$ rh-AChE: 5.56±0.82 nM.
$IC_{50}$ rh-BuChE: 522±120 nM.

EXAMPLE 14

2-(12-Amino-3-chloro-6,7,10,11-tetrahydro-7,11-methanocycloocta[b]quinolin-9-yl) Ethyl Methanesulfonate (HUP 13)

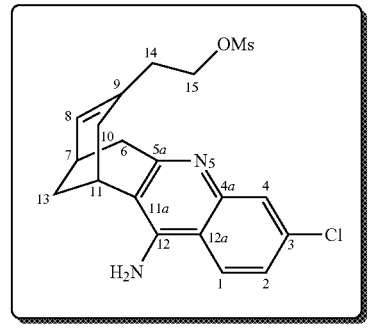

$C_{19}H_{21}ClN_2O_3S$
Mol. Wt.: 392.90

To a cooled (0° C.) stirred solution of alcohol (HUP 2) (944 mg, 3 mmol) and triethylamine (630 μL, 4.5 mmol) in dry THF (25 mL) was added methane sulfonyl chloride (350 μL, 4.5 mmol) dropwise over 10 min. The solution was stirred 2 h (0° C. to r.t.). The reaction mixture was then poured onto a saturated aqueous solution of $K_2CO_3$ and the aqueous phase was extracted with AcOEt (3×25 mL). The combined organic layers were washed with water (30 mL), dried with $MgSO_4$ and concentrated to afford a pale yellow solid (1.20 g, quantitative). Purification by flash chromatography (petroleum ether/AcOEt 3/7 then AcOEt then AcOEt/MeOH 8.5/1.5) afforded the desired Huprine (HUP 13) as an off white solid (1.11 g, 94%).

Rf (AcOEt/MeOH 8/2, v/v)=0.33.
m.p.=110° C. (decomposition).

IR (KBr): ν=3368, 3228, 2931, 1644, 1610, 1589, 1572, 1490, 1426, 1350, 1172, 1043, 956, 929, 772 cm$^{-1}$.

$^1$H NMR (300 MHz, MeOD): δ=1.90-1.94 (m, 1H, H$_{10}$), 2.05-2.11 (m, 2H, H$_{10}$, H$_{13}$), 2.24 (t, J=6.2 Hz, 2H, H$_{14}$), 2.50 (dd, J=17.5 Hz, J=4.2 Hz, 1H, H$_{13}$), 2.69-2.73 (m, 1H, H$_7$), 2.73 (s, 3H, OMs), 2.85 (d, J=17.7 Hz, 1H, H$_6$), 3.02 (dd, J=17.7 Hz, J=5.5 Hz, 1H, H$_6$), 3.27-3.31 (m, 1H, H$_{11}$), 4.10 (t, J=6.4 Hz, 2H, H$_{15}$), 5.67 (d, J=4.9 Hz, 1H, H$_8$), 7.28 (dd, J=9.0 Hz, J=1.9 Hz, 1H, H$_2$), 7.65 (d, J=1.9 Hz, 1H, H$_4$), 8.02 (d, J=9.0 Hz, 1H, H$_1$).

$^{13}$C NMR (75 MHz, MeOD): δ=27.9 (C$_{11}$), 29.1 (C$_7$), 29.6 (C$_{10}$), 34.3 (C$_{13}$), 36.9 (C$_6$), 37.6 (OMs), 39.6 (C$_{14}$), 69.7 (C$_{15}$), 115.3 (C$_{11a}$ or C$_{12a}$), 116.5 (C$_{11a}$ or C$_{12a}$), 123.2 (C$_4$), 125.5 (C$_1$), 126.1 (C$_2$), 128.9 (C$_8$), 133.8 (C$_3$), 137.7 (C$_9$), 144.4 (C$_{4a}$ or C$_{12}$), 153.1 (C$_{4a}$ or C$_{12}$), 156.4 (C$_{5a}$).

MS (ESI+): m/z (%): 393.27 (100) [M+H]$^+$, 395, 13 (40).

IC$_{50}$ rh-AChE: 8.50±1.10 nM.

IC$_{50}$ rh-BuChE: 415±97 nM.

EXAMPLE 15

3-Chloro-9-(2-hydrazinoethyl)-6,7,10,11-tetrahydro-7,11-methanocyclo octa[b]quinolin-12-amine Ditrifluoroacetic Acid (HUP 14)

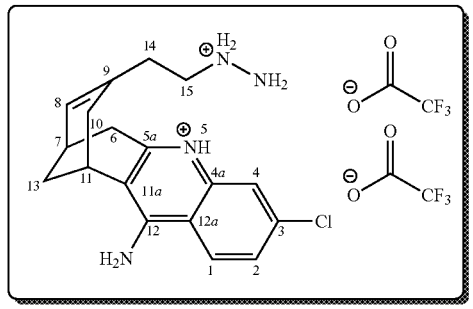

C$_{22}$H$_{23}$ClF$_6$N$_4$O$_4$
Mol. Wt.: 556.89

To a partially soluble suspension of iodinated compound (HUP 7) (7.1 mg, 0.017 mmol) in MeCN (2 mL) was added hydrazine monohydrate solution (8.2 μL, 0.169 mmol), and the mixture was heated to 55° C. for 13 h. The reaction mixture was concentrated to dryness then purified by preparative HPLC (System A) and freeze dried to afford the di-trifluoroacetate salt of the desired Huprine (HUP 14) as an off white solid (1.2 mg, 13%).

Rf (free base, AcOEt/MeOH 8/2, v/v)=0.43.

MS (ESI+): m/z (%): 329.33 (100) [M+H]$^+$, 331.27 (35).

IC$_{50}$ rh-AChE: 9.5±2.7 nM.

IC$_{50}$ rh-BuChE: 668±110 nM.

EXAMPLE 16

3-Chloro-9-[2-(hydroxyamino)ethyl]-6,7,10,11-tetrahydro-7,11-methano cycloocta[b]quinolin-12-amine Ditrifluoroacetic Acid (HUP 15)

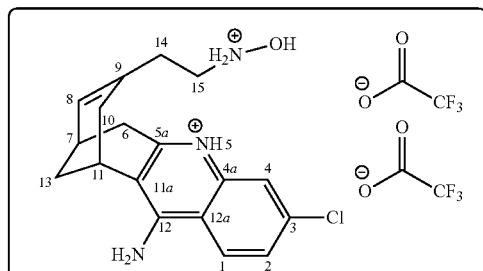

C$_{22}$H$_{23}$ClF$_6$N$_3$O$_5$
Mol. Wt.: 557.87

A solution of di-protected compound (HUP 16) (78 mg, 0.147 mmol) in anhydrous DCM (2 mL) was treated at 0° C. with trifluoroacetic acid (1 mL, 13.5 mmol). The solution was then stirred at r.t. 68 h. The reaction mixture was concentrated to dryness then purified by preparative HPLC (System A) to afford the desired Huprine (HUP 15) as a pale yellow solid (37 mg, 45%).

m.p.=130° C. (decomposition).

$^1$H NMR (300 MHz, MeOD): δ=1.94-2.16 (m, 3H, H$_{10}$, H$_{13}$), 2.24-2.37 (m, 2H, H$_{14}$), 2.60 (dd, J=17.6 Hz, J=4.4 Hz, 1H, H$_{13}$), 2.84-2.88 (m, 1H, H$_7$), 2.91 (d, J=18.1 Hz, 1H, H$_6$), 3.19-3.28 (m, 3H, H$_6$, H$_{15}$), 3.40-3.45 (m, 1H, H$_{11}$), 5.75 (d, J=4.7 Hz, 1H, H$_8$), 7.56 (dd, J=9.0 Hz, J=2.1 Hz, 1H, H$_2$), 7.73 (d, J=2.1 Hz, 1H, H$_4$), 8.34 (d, J=9.0 Hz, 1H, H$_1$).

$^{13}$C NMR (75 MHz, MeOD): δ=27.3 (C$_{11}$), 28.1 (C$_7$), 28.9 (C$_{10}$), 32.1 (C$_{14}$), 34.1 (C$_{13}$), 35.5 (C$_6$), 50.3 (C$_{15}$), 115.1 (C$_{11a}$ or C$_{12a}$), 115.4 (C$_{11a}$ or C$_{12a}$), 119.3 (C$_4$), 126.4 (C$_1$), 127.7 (C$_2$), 128.1 (C$_8$), 133.9 (C$_3$), 139.6 (C$_9$), 140.5 (C$_{4a}$ or C$_{12}$), 152.9 (C$_{4a}$ or C$_{12}$), 156.8 (C$_{5a}$).

MS (ESI+): m/z (%): 330.26 (100) [M+H]$^+$, 332.19 (36).

IC$_{50}$ rh-AChE: 18.5±2.2 nM.

IC$_{50}$ rh-BuChE: 43% at 1 μM.

EXAMPLE 17

Tert-butyl [2-(12-amino-3-chloro-6,7,10,11-tetrahydro-7,11-methano cycloocta[b]quinolin-9-yl)ethyl][(tert-butoxycarbonyl)oxy]carbamate (HUP 16)

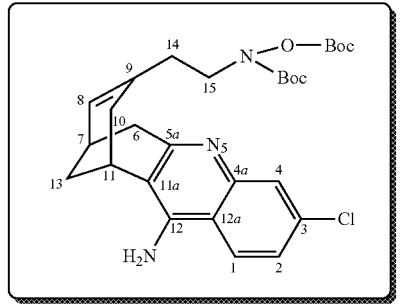

C$_{28}$H$_{36}$ClN$_3$O$_5$
Mol. Wt.: 530.06

A solution of tert-butyl-N-(tert-butoxycarbonyl)-carbamate (140 mg, 0.6 mmol) in anhydrous DMF (1.3 mL) was treated with sodium hydride (60% in oil, 26 mg, 0.65 mmol). The reaction mixture was stirred 40 min at r.t. and treated with a solution of mesylate (HUP 13) (157 mg, 0.4 mmol) in anhydrous DMF (2 mL). The reaction mixture was stirred at r.t. for 120 h, then at 60° C. for 5 h. The mixture was then diluted with water (50 mL) and extracted with AcOEt (3×30 mL). The combined organic layers were washed with brine (50 mL), then water (50 mL), dried with $Na_2SO_4$ and concentrated under reduced pressure to afford a yellow solid (313 mg). Purification by flash chromatography (AcOEt/MeOH 10/0 to 8/2, v/v) afforded the desired Huprine (HUP 16) as a white solid (98 mg, 46%).

Rf (AcOEt/MeOH 8/2, v/v)=0.50.

m.p.=114° C. (decomposition).

$^1$H NMR (300 MHz, $CDCl_3$): δ=1.41 (s, 9H, N-Boc or O-Boc), 1.46 (s, 9H, N-Boc or O-Boc), 1.84-2.02 (m, 3H, $H_{10}$, $H_{13}$), 2.10-2.22 (m, 2H, $H_{14}$), 2.52 (dd, J=17.1 Hz, J=3.4 Hz, 1H, $H_{13}$), 2.67-2.71 (m, 1H, $H_7$), 2.89 (d, J=17.5 Hz, 1H, $H_6$), 3.06 (dd, J=17.6 Hz, J=5.6 Hz, 1H, $H_6$), 3.14-3.18 (m, 1H, $H_{11}$), 3.66-3.88 (m, 2H, $H_{15}$), 5.03 (brs, 2H, $NH_2$), 5.56 (d, J=5.1 Hz, 1H, $H_8$), 7.21 (dd, J=9.0 Hz, J=1.9 Hz, 1H, $H_2$), 7.67 (d, J=9.0 Hz, 1H, $H_1$), 7.77 (d, J=1.9 Hz, 1H, $H_4$).

$^{13}$C NMR (75 MHz, $CDCl_3$): δ=27.4 ($C_{11}$), 27.6 (N-Boc or O-Boc), 28.1 (N-Boc or O-Boc), 28.2 ($C_7$), 28.9 ($C_{10}$), 33.8 ($C_{13}$), 34.8 ($C_{14}$), 39.4 ($C_6$), 68.1 ($C_{15}$), 82.3 (C-$Me_3$ of N-Boc), 84.9 (C-$Me_3$ of O-Boc), 115.1 ($C_{11a}$ or $C_{12a}$), 115.8 ($C_{11a}$ or $C_{12a}$), 122.0 ($C_1$), 124.6 ($C_2$), 126.9 ($C_4$), 127.0 ($C_8$), 132.9 ($C_3$), 134.6 ($C_9$), 146.5 ($C_{4a}$ or $C_{12}$), 147.0 ($C_{4a}$ or $C_{12}$), 152.2 (C=O of N-Boc), 154.8 (C=O of O-Boc), 158.3 ($C_{5a}$).

MS (ESI+): m/z (%): 530.20 (100) [M+H]$^+$, 532.20 (39).

$IC_{50}$ rh-AChE: 14.8±3.2 nM.

$IC_{50}$ rh-BuChE: 421±72 nM.

EXAMPLE 18

2-(12-Amino-3-chloro-6,7,10,11-tetrahydro-7,11-methanocycloocta[b]quinolin-9-yl)ethyl Carbamate Trifluoroacetic Acid (HUP 17)

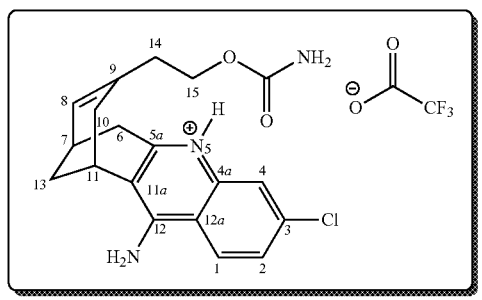

$C_{21}H_{21}ClF_3N_3O_4$
Mol. Wt.: 471.86

To a partially soluble suspension of alcohol (HUP 2) (94.4 mg, 0.3 mmol) in MeCN (5 mL) was added dropwise a solution of triphosgene (178 mg, 0.6 mmol) in MeCN (5 mL). The reaction mixture was stirred 20 min at 65° C. then at r.t. for 100 min, then the excess of triphosgene was quenched by bubbling ammoniac gas into the reaction mixture which led to the formation of the carbamate. The reaction mixture was concentrated to dryness then purified by preparative HPLC (System A) and freeze dried to afford the trifluoroacetate salt of the desired Huprine (HUP 17) as a brown solid (82.6 mg, 58%).

m.p.=118° C. (decomposition).

$^1$H NMR (300 MHz, MeOD): δ=1.93-1.97 (m, 1H, $H_{10}$), 2.03-2.09 (m, 2H, $H_{10}$, $H_{13}$), 2.18 (t, J=6.5 Hz, 2H, $H_{14}$), 2.55 (dd, J=13.6 Hz, J=3.8 Hz, 1H, $H_{13}$), 2.78-2.82 (m, 1H, $H_7$), 2.87 (d, J=18.3 Hz, 1H, $H_6$), 3.20 (dd, J=17.9 Hz, J=5.3 Hz, 1H, $H_6$), 3.80-3.84 (m, 1H, $H_{11}$), 3.87-4.00 (m, 2H, $H_{15}$), 5.66 (d, J=5.1 Hz, 1H, $H_8$), 7.55 (dd, J=9.0 Hz, J=1.7 Hz, 1H, $H_2$), 7.72 (d, J=1.7 Hz, 1H, $H_4$), 8.33 (d, J=9.0 Hz, 1H, $H_1$).

$^{13}$C NMR (75 MHz, MeOD): δ=27.5 ($C_{11}$), 28.2 ($C_7$), 29.1 ($C_{10}$), 34.1 ($C_{13}$), 35.8 ($C_6$), 37.8 ($C_{14}$), 63.6 ($C_{15}$), 115.3 ($C_{11a}$ or $C_{12a}$), 115.4 ($C_{11a}$ or $C_{12a}$), 119.3 ($C_4$), 126.4 ($C_1$), 127.3 ($C_2$), 127.6 ($C_8$), 135.2 ($C_3$), 139.6 ($C_9$), 140.4 ($C_{4a}$ or $C_{12}$), 152.9 ($C_{4a}$ or $C_{12}$), 156.8 (C=O), 159.7 ($C_{5a}$).

MS (ESI+): m/z (%): 358.27 (100) [M+H]$^+$, 360.20 (34).

$IC_{50}$ rh-AChE: 18.5±2.2 nM.

$IC_{50}$ rh-BuChE: 413±40 nM.

EXAMPLE 19

2-(12-Amino-3-chloro-6,7,10,11-tetrahydro-7,11-methanocycloocta[b]quinolin-9-yl)ethyl Acrylate (HUP 18)

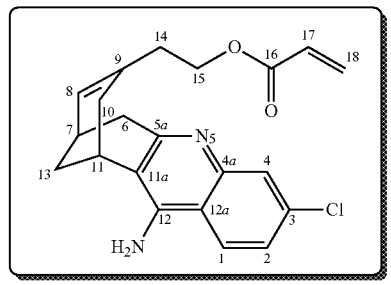

$C_{21}H_{21}ClN_2O_2$
Mol. Wt.: 368.86

To a cooled to 0° C. solution of alcohol (HUP 2) (20 mg, 63.5 µmol) and triethylamine (27 µL, 200 µmol) in THF (1 mL) was added dropwise acryloyl chloride (16 µL, 200 µmol). A white precipitate appeared: 0.5 mL THF was added. The mixture was stirred 1 h at r.t. then concentrated to dryness (additional 0.5 mL THF was added at 45 min). Purification by flash chromatography (AcOEt/EtOH/$NEt_3$ 100/0/0 to 84/14.4/1.6, v/v) afforded the desired Huprine (HUP 18) as a pale yellow solid (7.9 mg, 34%).

Rf (AcOEt/MeOH 8/2, v/v)=0.40.

$^1$H NMR (300 MHz, $CDCl_3$): δ=1.90-2.03 (m, 3H, $H_{10}$, $H_{10}$, $H_{13}$), 2.18 (t, J=6.8 Hz, 2H, $H_{14}$), 2.50 (dd, J=17.1 Hz, J=4.9 Hz, 1H, $H_{13}$), 2.73-2.77 (m, 1H, $H_7$), 2.95 (d, J=17.7 Hz, 1H, $H_6$), 3.12 (dd, J=18.1 Hz, J=5.8 Hz, 1H, $H_6$), 3.16-3.21 (m, 1H, $H_{11}$), 4.08 (q, J=5.5 Hz, 2H, $H_{15}$), 5.02 (brs, 2H, $NH_2$), 5.61 (d, J=5.1 Hz, 1H, $H_8$), 5.64 (dd, J=17.1 Hz, J=1.5 Hz, 1H, $H_{18}$), 5.86 (dd, J=17.3 Hz, J=10.4 Hz, 1H, $H_{18}$), 6.15 (dd, J=17.1 Hz, J=1.5 Hz, 1H, $H_{18}$), 7.28 (dd, J=9.0 Hz, J=1.7 Hz, 1H, $H_2$), 7.67 (d, J=9.0 Hz, 1H, $H_1$), 7.85 (d, J=2.1 Hz, 1H, $H_4$).

$^{13}$C NMR (75 MHz, $CDCl_3$): δ=27.5 ($C_{11}$), 28.3 ($C_7$), 29.0 ($C_{10}$), 33.6 ($C_{13}$), 36.5 ($C_{14}$), 39.1 ($C_6$), 62.5 ($C_{15}$), 115.0 ($C_{11a}$ or $C_{12a}$), 115.8 ($C_{11a}$ or $C_{12a}$), 122.0 ($C_1$), 124.9 ($C_2$), 127.2 ($C_4$), 127.7 ($C_8$), 128.2 ($C_{17}$), 130.7 ($C_{18}$), 132.3 ($C_3$), 139.9 ($C_9$), 141.2 ($C_{4a}$ or $C_{12}$), 146.6 ($C_{4a}$ or $C_{12}$), 157.9 ($C_{5a}$), 166.1 ($C_{16}$).

MS (ESI+): m/z (%): 369.05 (100) [M+H]$^+$, 317.11 (33).

IC$_{50}$ rh-AChE: 20.4±4.6 nM.

IC$_{50}$ rh-BuChE: 207±16 nM.

IC$_{50}$ erythrocyte h-AChE: 129 nM.

EXAMPLE 20

2-(12-Amino-3-chloro-6,7,10,11-tetrahydro-7,11-methanocycloocta[b]quinolin-9-yl)-N,N-dimethylacetamide Trifluoroacetic Acid (HUP 19)

$C_{20}H_{17}ClF_3N_2O_3$
Mol. Wt.: 425.81

A suspension of acid (HUP 11) (99 mg, 0.27 mmol) in DMF (1 mL) and SOCl$_2$ solution (0.2 mL, 2.74 mmol) was heated at 75° C. for 1 h30. The reaction mixture was then cooled to r.t. and carefully hydrolyzed with saturated aqueous K$_2$CO$_3$ solution (6 mL): a red precipitate appeared; then 1 M aqueous HCl solution (3 mL). The mixture was extracted with AcOEt (2×10 mL) then with DCM (2×20 mL). The combined organic layers were washed with water (2×20 mL), dried with MgSO$_4$ and concentrated under reduced pressure to afford brown oil. This residue was recrystalized in AcOEt/Et2O to afford the desired Huprine as a yellow solid (69 mg, 74%). Purification by preparative HPLC (System A) and freeze drying afforded the trifluoroacetate salt of the desired Huprine (HUP 19) as a pale yellow solid (71.3 mg, 62%).

Rf (free base, AcOEt)=0.66.

m.p. (free base)=217-218° C.

IR (free base, KBr): ν=3342, 3236, 2933, 1713, 1657, 1588, 1468, 1415, 1375, 1229, 1155, 1084, 933 cm$^{-1}$.

$^1$H NMR (300 MHz, MeOD): δ=1.94-2.10 (m, 3H, H$_{10}$, H$_{13}$), 2.50 (dd, 1H, H$_{13}$, J=17.3 Hz, J=4.1 Hz), 2.80 (s, 1H, NMe), 2.90 (s, 1H, NMe), 2.85-2.93 (m, 2H, H$_7$, H$_6$), 3.01 (s, 2H, H$_{14}$), 3.23 (dd, J=18.1 Hz, J=5.6 Hz, 1H, H$_6$), 3.98-4.02 (m, 1H, H$_{11}$), 5.66 (d, J=5.1 Hz, 1H, H$_8$), 7.58 (dd, J=9.2 Hz, J=2.1 Hz, 1H, H$_2$), 7.73 (d, J=2.1 Hz, 1H, H$_4$), 8.35 (d, J=9.2 Hz, 1H, H$_1$).

$^{13}$C NMR (75 MHz, MeOD): δ=27.5 ($C_{11}$), 28.3 ($C_7$), 29.0 ($C_{10}$), 34.3 ($C_{13}$), 35.7 ($C_6$), 35.8 (NMe), 38.1 (NMe), 43.0 ($C_{14}$), 115.3 ($C_{11a}$ or $C_{12a}$), 115.4 ($C_{11a}$ or $C_{12a}$), 119.2 ($C_4$), 126.4 ($C_1$), 127.7 ($C_2$), 128.2 ($C_8$), 133.3 ($C_3$), 140.0 ($C_9$), 140.5 ($C_{4a}$ or $C_{12}$), 152.9 ($C_{4a}$ or $C_{12}$), 156.9 ($C_{5a}$), 173.2 ($C_{15}$).

MS (ESI+): m/z (%): 356.28 (100) [M+H]$^+$, 358.20 (34).

HPLC: tr=14.7 (purity 84%)

IC$_{50}$ rh-AChE: 26.3±1.7 nM.

IC$_{50}$ rh-BuChE: 2760 nM.

EXAMPLE 21

2-(12-Amino-3-chloro-6,7,10,11-tetrahydro-7,11-methanocycloocta[b]quinolin-9-yl)acetamide Trifluoroacetic Acid (HUP 20)

$C_{20}H_{19}ClF_3N_3O_3$
Mol. Wt.: 441.11

To a partially soluble suspension of ester (HUP 1) (178 mg, 0.5 mmol) and sodium cyanide (25 mg, 0.25 mmol) in absolute EtOH (2 mL) was bubbled gaseous ammoniac for 2 min. The reaction mixture was refluxed for 6 days then the solvents were concentrated under reduced pressure to dryness. Aqueous ammonia solution (28-30% in water) was added and the suspension stirred for 2 days at r.t. The reaction mixture was concentrated to dryness then purified by preparative HPLC (System A) and freeze dried to afford the trifluoroacetate salt of the desired Huprine (HUP 20) as a white solid (15.3 mg, 7%).

m.p.=126° C. (decomposition).

$^1$H NMR (300 MHz, MeOD): δ=1.93-2.00 (m, 1H, H$_{10}$), 2.06-2.16 (m, 2H, H$_{10}$, H$_{13}$), 2.55 (dd, 1H, J=17.7 Hz, J=4.1 Hz, H$_{13}$), 2.78-2.81 (m, 2H, H$_{14}$), 2.83-2.87 (m, 1H, H$_7$), 2.91 (d, J=17.9 Hz, 1H, H$_6$), 3.22 (dd, J=17.9 Hz, J=5.5 Hz, 1H, H$_6$), 3.38-3.42 (m, 1H, H$_{11}$), 5.76 (d, J=5.3 Hz, 1H, H$_8$), 7.58 (dd, J=9.1 Hz, J=2.1 Hz, 1H, H$_2$), 7.72 (d, J=2.1 Hz, 1H, H$_4$), 8.34 (d, J=9.1 Hz, 1H, H$_1$).

$^{13}$C NMR (75 MHz, MeOD): δ=27.4 ($C_{11}$), 28.3 ($C_7$), 28.9 ($C_{10}$), 34.0 ($C_{13}$), 35.6 ($C_6$), 45.0 ($C_{14}$), 115.3 ($C_{11a}$ or $C_{12a}$), 115.4 ($C_{11a}$ or $C_{12a}$), 119.2 ($C_4$), 126.4 ($C_1$), 127.7 ($C_2$), 128.9 ($C_8$), 133.6 ($C_3$), 139.7 ($C_9$), 140.5 ($C_{4a}$ or $C_{12}$), 152.9 ($C_{4a}$ or $C_{12}$), 156.9 ($C_{5a}$), 176.4 ($C_{15}$).

MS (ESI+): m/z (%): 328.33 (100) [M+H]$^+$, 330.20 (33).

IC$_{50}$ rh-AChE: 29.3±3.7 nM.

IC$_{50}$ rh-BuChE: <1% at 1 μM.

EXAMPLE 22

3-Chloro-9-[2-(dimethylamino)ethyl]-6,7,10,11-tetrahydro-7,11-methano cycloocta[b]quinolin-12-amine Ditrifluoroacetic Acid (HUP 21)

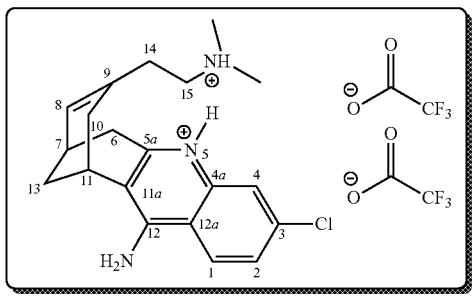

$C_{24}H_{26}ClF_6N_3O_4$
Mol. Wt.: 569.92

A partially soluble suspension of iodinated compound (HUP 7) (61 mg, 0.14 mmol), dimethylamine hydrochloride (147 mg, 1.80 mmol) and sodium bicarbonate (151 mg, 1.8 mmol) AcOEt/MeCN mixture (10 mL/2 mL) was stirred 13 h at reflux. The reaction mixture was concentrated to dryness then purified by preparative HPLC (System A) and freeze dried to afford the di-trifluoroacetate salt of the desired Huprine (HUP 21) as a white solid (11.1 mg, 14%).

Rf (AcOEt/MeOH 8/2, v/v)=0.58.

m.p.=118° C. (decomposition).

IR (KBr): ν=3354, 3174, 2940, 1673, 1591, 1470, 1421, 1201, 1126, 834, 721 cm$^{-1}$.

$^1$H NMR (300 MHz, MeOD): δ=2.00-2.08 (m, 3H, $H_{10}$, $H_{13}$), 2.28-2.32 (m, 2H, $H_{14}$), 2.60 (dd, J=17.0 Hz, J=3.9 Hz, 1H, $H_{13}$), 2.82 (s, 6H, Me$_2$N), 2.82-2.93 (m, 2H, $H_7$, $H_6$), 3.12 (t, J=8.1 Hz, 2H, $H_{15}$), 3.19-3.23 (m, 1H, $H_6$), 3.42-3.46 (m, 1H, $H_{11}$), 5.77 (d, J=5.1 Hz, 1H, $H_8$), 7.61 (dd, J=9.0 Hz, J=1.9 Hz, 1H, $H_2$), 7.75 (d, J=1.5 Hz, 1H, $H_4$), 8.36 (d, J=9.0 Hz, 1H, $H_1$).

$^{13}$C NMR (75 MHz, MeOD): δ=27.3 ($C_{11}$), 28.2 ($C_7$), 28.9 ($C_{10}$), 33.0 ($C_{14}$), 34.3 ($C_{13}$), 35.6 ($C_6$), 43.5 (2C, Me$_2$N), 57.1 ($C_{15}$), 115.1 ($C_{11a}$ or $C_{12a}$), 115.5 ($C_{11a}$ or $C_{12a}$), 119.3 ($C_4$), 126.4 ($C_1$), 127.8 ($C_2$), 128.2 ($C_8$), 133.9 ($C_3$), 139.7 ($C_9$), 140.6 ($C_{4a}$ or $C_{12}$), 152.9 ($C_{4a}$ or $C_{12}$), 156.9 ($C_{5a}$).

MS (ESI+): m/z (%): 342.33 (100) [M+H]$^+$, 344.27 (37).

IC$_{50}$ rh-AChE: 97±10 nM.

IC$_{50}$ rh-BuChE: 2910 nM.

EXAMPLE 23

Methyl 1-[2-(12-amino-3-chloro-6,7,10,11-tetrahydro-7,11-methano cycloocta[b]quinolin-9-yl)ethyl]-1H-1,2,3-triazole-4-carboxylate (HUP 22)

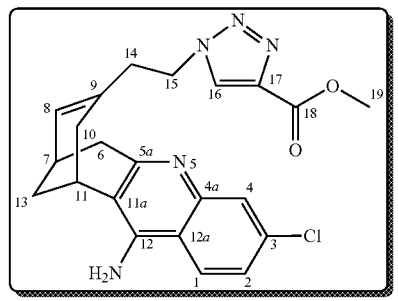

$C_{22}H_{22}ClN_5O_2$
Mol. Wt.: 423.90

A solution of azide (HUP 12) (64 mg, 188 μmol), methyl propionate (18 μL, 200 μmol) and copper iodide (4.4 mg, 22.7 μmol) in MeCN (4 mL) was stirred 25 h at r.t. with light protection. The reaction mixture was concentrated to dryness then purified by flash chromatography (AcOEt/MeOH 10/0 to 9/1, v/v) to afford the desired Huprine (HUP 22) as a yellow solid (47.5 mg, 60%).

Rf (AcOEt/MeOH 9/1, v/v)=0.10.

m.p.=126° C. (decomposition).

IR (KBr): ν=3365, 2927, 1732, 1646, 1609, 1572, 1490, 1435, 1373, 1218, 1109, 929, 770 cm$^{-1}$.

$^1$H NMR (300 MHz, MeOD): δ=1.88-1.99 (m, 2H, $H_{10}$), 2.04-2.09 (m, 1H, $H_{13}$), 2.45-2.52 (m, 3H, $H_{14}$, $H_{13}$), 2.65-2.69 (m, 1H, $H_7$), 2.66 (d, J=17.5 Hz, 1H, $H_6$), 3.00 (dd, J=17.3 Hz, J=5.4 Hz, 1H, $H_6$), 3.29-3.33 (m, 1H, $H_{11}$), 3.84 (s, 3H, $H_{19}$), 4.38 (td, J=2.3 Hz, J=6.8 Hz, 2H, $H_{15}$), 5.49 (d, J=5.1 Hz, 1H, $H_8$), 7.31 (dd, J=8.9 Hz, J=1.7 Hz, 1H, $H_2$), 7.67 (d, J=1.7 Hz, 1H, $H_4$), 8.05 (s, 1H, $H_{16}$), 8.06 (d, J=8.9 Hz, 1H, $H_1$).

$^{13}$C NMR (75 MHz, MeOD): δ=28.1 ($C_{11}$), 29.5 ($C_7$), 29.9 ($C_{10}$), 34.2 ($C_{13}$), 38.2 ($C_{14}$), 39.5 ($C_6$), 49.9 ($C_{15}$), 52.6 ($C_{19}$), 115.2 ($C_{11a}$ or $C_{12a}$), 117.0 ($C_{11a}$ or $C_{12a}$), 125.0 ($C_1$), 125.3 ($C_2$), 125.8 ($C_4$), 129.3 ($C_{16}$), 129.6 ($C_8$), 133.6 ($C_3$), 136.1 ($C_9$), 140.0 ($C_{17}$), 147.3 ($C_{4a}$), 150.1 ($C_{12}$), 158.3 ($C_{5a}$), 162.2 ($C_{18}$).

MS (ESI+): m/z (%): 424.20 (100) [M+H]$^+$, 426.13 (33).

IC$_{50}$ rh-AChE: 130±15 nM.

IC$_{50}$ rh-BuChE: 42% at 1 μM.

EXAMPLE 24

{1-[2-(12-Amino-3-chloro-6,7,10,11-tetrahydro-7,11-methanocycloocta[b]quinolin-9-yl)ethyl]-1H-1,2,3-triazol-4-yl}methanol Trifluoroacetic Acid (HUP 23)

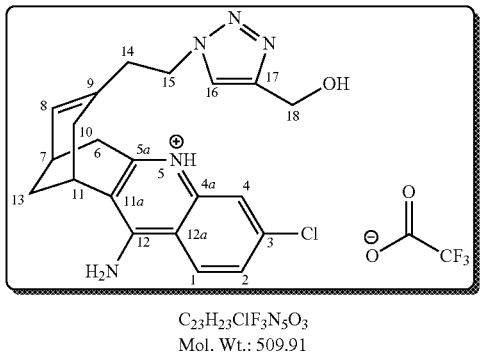

$C_{23}H_{23}ClF_3N_5O_3$
Mol. Wt.: 509.91

To a cooled to 0° C. stirred suspension of LiAlH$_4$ (11 mg, 275 µmol) in THF (500 µL) was added dropwise a solution of triazole (HUP 22) (12.7 mg, 30 µmol) in THF (1 mL). The solution was stirred 30 min (0° C. to r.t.) then quenched carefully at 0° C. by the addition of water (50 µL), then 5 M NaOH solution (50 µL), then water (150 µL). The reaction mixture was stirred 10 min (0° C. to r.t.) concentrated to dryness. The residue was purified by preparative HPLC (System A) and freeze dried to afford the trifluoroacetate salt of the desired Huprine (HUP 23) as a white solid (62.2 mg, 57%).

m.p.=119° C. (decomposition).

$^1$H NMR (300 MHz, MeOD): δ=1.86-2.02 (m, 2H, H$_{10}$), 2.04-2.12 (m, 1H, H$_{13}$), 2.42-2.55 (m, 3H, H$_{14}$, H$_{13}$), 2.58-2.65 (d, J=17.5 Hz, 1H, H$_6$), 2.66-2.70 (m, 1H, H$_7$), 3.10 (dd, J=17.8 Hz, J=5.5 Hz, 1H, H$_6$), 3.34-3.38 (m, 1H, H$_{11}$), 4.33 (t, J=5.8 Hz, 2H, H$_{15}$), 4.50 (s, 1H, H$_{18}$), 5.43 (d, J=5.1 Hz, 1H, H$_8$), 7.59 (s, 1H, H$_{16}$), 7.61 (dd, J=8.9 Hz, J=1.7 Hz, 1H, H$_2$), 7.77 (d, J=1.7 Hz, 1H, H$_4$), 8.36 (d, J=8.9 Hz, 1H, H$_1$).

$^{13}$C NMR (75 MHz, MeOD): δ=27.4 (C$_{11}$), 28.0 (C$_7$), 28.9 (C$_{10}$), 33.2 (C$_{13}$), 35.4 (C$_6$), 38.2 (C$_{14}$), 48.5 (C$_{15}$), 56.4 (C$_{18}$), 115.2 (C$_{11a}$ or C$_{12a}$), 115.5 (C$_{11a}$ or C$_{12a}$), 119.5 (C$_4$), 123.6 (CH$_{16}$), 126.4 (C$_1$), 127.7 (C$_2$), 128.6 (C$_8$), 134.2 (C$_3$), 139.7 (C$_9$), 140.4 (C$_{17}$), 148.9 (C$_{4a}$), 152.7 (C$_{12}$), 156.8 (C$_{5a}$).

MS (ESI+): m/z (%): 396.27 (100) [M+H]$^+$, 114.73 (59), 398.20 (32).

HPLC: tr=13.7 (purity 99%).

IC$_{50}$ rh-AChE: 210±28 nM.

IC$_{50}$ rh-BuChE: 18% at 1 µM.

EXAMPLE 25

9-(2-Aminoethyl)-3-chloro-6,7,10,11-tetrahydro-7,11-methanocycloocta[b]quinolin-12-amine Ditrifluoroacetic Acid (HUP 24)

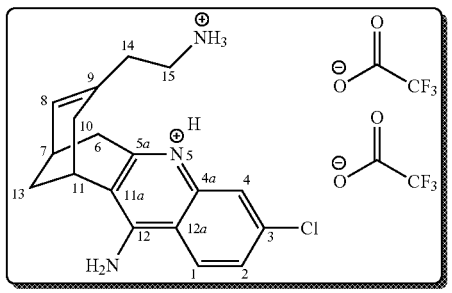

$C_{22}H_{22}ClF_6N_3O_4$
Mol. Wt.: 540.86

A solution of azide (HUP 12) (68 mg, 0.2 mmol) and triphenylphosphine (53 mg, 0.2 mmol) in THF (1 mL) was stirred 2 h at 0° C. and 1 h (0° C. to r.t.). Water (10 µL) was then added at 0° C. and the mixture was stirred at r.t. for 13 h. The reaction mixture was concentrated to dryness then purified by preparative HPLC (System A) and freeze dried to afford the trifluoroacetate salt of the desired Huprine (HUP 24) as a white solid (65 mg, 60%).

m.p.=150° C. (decomposition).

$^1$H NMR (300 MHz, MeOD): δ=1.95-2.04 (m, 2H, H$_{10}$, H$_{13}$), 2.10-2.15 (m, 1H, H$_{10}$), 2.22 (t, J=7.4 Hz, 2H, H$_{13}$), 2.60 (dd, J=17.7 Hz, J=3.8 Hz, 1H, H$_{13}$), 2.86-2.97 (m, 4H, H$_7$, H$_6$, H$_{15}$), 2.24 (dd, J=17.7 Hz, J=5.6 Hz, 1H, H$_6$), 3.41-3.45 (m, 1H, H$_{11}$), 5.74 (d, J=4.9 Hz, 1H, H$_8$), 7.57 (dd, J=9.0 Hz, J=1.9 Hz, 1H, H$_2$), 7.74 (d, J=1.9 Hz, 1H, H$_4$), 8.35 (d, J=9.0 Hz, 1H, H$_1$).

$^{13}$C NMR (75 MHz, MeOD): δ=27.3 (C$_{11}$), 28.1 (C$_7$), 28.9 (C$_{10}$), 34.1 (C$_{13}$), 35.6 (C$_6$), 36.0 (C$_{14}$), 38.8 (C$_{15}$), 115.1 (C$_{11a}$ or C$_{12a}$), 115.4 (C$_{11a}$ or C$_{12a}$), 119.3 (C$_4$), 126.4 (C$_1$), 127.7 (C$_2$), 128.1 (C$_8$), 134.1 (C$_3$), 139.6 (C$_9$), 140.5 (C$_{4a}$ or C$_{12}$), 152.9 (C$_{4a}$ or C$_{12}$), 156.8 (C$_{5a}$).

MS (ESI+): m/z (%): 314.30 (100) [M+H]$^+$, 316.23 (35), 178.05 (31).

IC$_{50}$ rh-AChE: 244±62 nM.

IC$_{50}$ rh-BuChE: 991 nM.

EXAMPLE 26

2-(12-Amino-3-chloro-6,7,10,11-tetrahydro-7,11-methanocycloocta[b]quinolin-9-yl)-N,N,N-trimethylethanaminium Ditrifluoroacetic Acid (HUP 25)

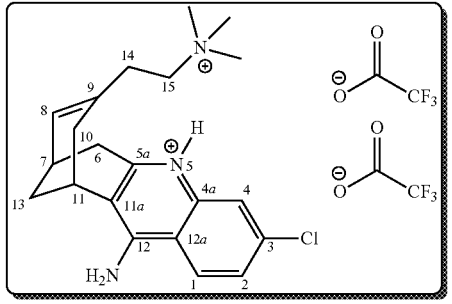

$C_{25}H_{28}ClF_6N_3O_4$
Mol. Wt.: 583.95

To a partially soluble suspension of iodinated compound (HUP 7) (71 mg, 0.167 mmol) in MeCN (2 mL) was added a solution of 1 M trimethylamine in THF (1.7 mL, 1.67 mmol), and the mixture was heated to 55° C. for 13 h. The reaction mixture was concentrated to dryness then purified by preparative HPLC (System A) and freeze dried to afford the ditrifluoroacetate salt of the desired Huprine (HUP 25) as a white solid (26.3 mg, 27%) along with alkene (HUP 3) (37.7 mg, 55%) as β-elimination byproduct.

Rf (AcOEt/MeOH 8/2, v/v)=0.67.

m.p.=188° C. (decomposition).

$^1$H NMR (300 MHz, MeOD): δ=2.00-2.11 (m, 3H, $H_{10}$, $H_{13}$), 2.39 (t, J=6.9 Hz, 2H, $H_{14}$), 2.60 (dd, J=17.1 Hz, J=3.8 Hz, 1H, $H_{13}$), 2.85-2.94 (m, 2H, $H_7$, $H_6$), 3.07 (s, 9H, $Me_3N^+$), 3.18-3.24 (m, 1H, $H_6$), 3.29-3.33 (m, 2H, $H_{15}$), 3.43-3.46 (m, 1H, $H_{11}$), 5.80 (d, J=4.7 Hz, 1H, $H_8$), 7.61 (dd, J=9.0 Hz, J=1.9 Hz, 1H, $H_2$), 7.76 (d, J=1.9 Hz, 1H, $H_4$), 8.37 (d, J=9.0 Hz, 1H, $H_1$).

$^{13}$C NMR (75 MHz, MeOD): δ=27.3 ($C_{11}$), 28.2 ($C_7$), 28.9 ($C_{10}$), 31.1 ($C_{14}$), 34.5 ($C_{13}$), 35.5 ($C_6$), 53.4 ($Me_3N^+$), 53.5 ($Me_3N^+$), 53.6 ($Me_3N^+$), 66.0 ($C_{15}$), 115.1 ($C_{11a}$ or $C_{12a}$), 115.4 ($C_{11a}$ or $C_{12a}$), 119.3 ($C_4$), 126.5 ($C_1$), 127.8 ($C_2$), 128.5 ($C_8$), 133.5 ($C_3$), 139.7 ($C_9$), 140.6 ($C_{4a}$ or $C_{12}$), 152.8 ($C_{4a}$ or $C_{12}$), 156.9 ($C_{5a}$).

MS (ESI+): m/z (%): 356.21 (100) $[M+H]^+$, 178.85 (51) $[M+2H]^{2+}$, 358.20 (33).

$IC_{50}$ rh-AChE: 262±22 nM.

$IC_{50}$ rh-BuChE: <1% at 1 μM.

EXAMPLE 27

Dimethyl [2-(12-Amino-3-chloro-6,7,10,11-tetrahydro-7,11-methano cycloocta[b]quinolin-9-yl)ethyl]malonate (HUP 26)

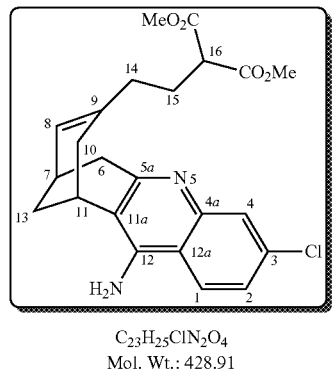

$C_{23}H_{25}ClN_2O_4$
Mol. Wt.: 428.91

To a solution of sodium dimethylmalonate [prepared from sodium (106 mg, 4.6 mmol) and dimethyl malonate (686 μL, 6.0 mmol) in dry THF (4 mL) let for 1 h30 in ultrasounds bath] was added a solution of mesyl compound mesylate (HUP 13) (1.572 g, 4.0 mmol) in dry THF (14 mL). The mixture was stirred at reflux temperature for 5 days. The cooled reaction mixture was then hydrolyzed with water (5 mL) and concentrated to dryness. Water (40 mL) was then added and the product extracted with AcOEt (3×50 mL). The combined organic layers were dried with $Na_2SO_4$ and concentrated under reduced pressure to afford a brown residue (1.877 g). Purification by flash chromatography (petroleum ether/AcOEt/MeOH 10/0/0 to 0/9/1, v/v/v) afforded the desired Huprine (HUP 26) as a white solid (1.098 g, 64%).

Rf (AcOEt/MeOH 8/2, v/v)=0.31.

$^1$H NMR (300 MHz, $CDCl_3$): δ=1.78-1.83 (m, 4H, $H_{14}$, $H_{15}$), 1.87-1.97 (m, 3H, $H_{10}$, $H_{10}$, $H_{13}$), 2.39 (dd, J=16.6 Hz, J=4.0 Hz, 1H, $H_{13}$), 2.67-2.71 (m, 1H, $H_7$), 2.89 (d, J=17.5 Hz, 1H, $H_6$), 3.01-3.10 (m, 2H, $H_6$, $H_{16}$), 3.15-3.17 (m, 1H, $H_{11}$), 3.51 (s, 3H, OMe), 3.63 (s, 3H, OMe), 4.97 (brs, $NH_2$), 5.49 (d, J=5.1 Hz, 1H, $H_8$), 7.19 (dd, J=9.0 Hz, J=2.1 Hz, 1H, $H_2$), 7.63 (d, J=9.0 Hz, 1H, $H_1$), 7.79 (d, J=2.1 Hz, 1H, $H_4$).

$^{13}$C NMR (75 MHz, $CDCl_3$): δ=26.5 ($C_{15}$), 27.4 ($C_{11}$), 28.3 ($C_7$), 29.1 ($C_{10}$), 33.4 ($C_{13}$), 34.7 ($C_{14}$), 39.8 ($C_6$), 50.4 ($C_{16}$), 52.3 (OMe), 52.4 (OMe), 115.0 ($C_{11a}$ or $C_{12a}$), 115.9 ($C_{11a}$ or $C_{12a}$), 121.9 ($C_1$), 124.4 ($C_2$), 126.5 ($C_8$), 127.5 ($C_4$), 134.1 ($C_3$), 134.2 ($C_9$), 145.9 ($C_{4a}$ or $C_{12}$), 147.5 ($C_{4a}$ or $C_{12}$), 158.9 ($C_{5a}$), 169.7 (C=O), 169.8 (C=O).

MS (ESI+): m/z (%): 429.40 (100) $[M+H]^+$, 431.27 (38), 856.80 (35), 858.60 (31).

EXAMPLE 28

Diethyl[2-(12-Amino-3-chloro-6,7,10,11-tetrahydro-7,11-methano cycloocta[b]quinolin-9-yl)ethyl]malonate (HUP 27)

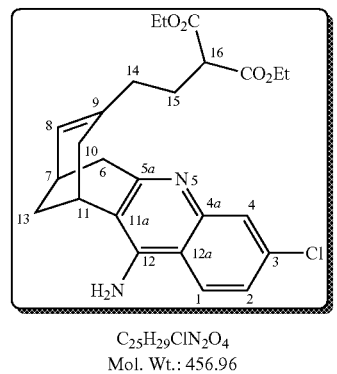

$C_{25}H_{29}ClN_2O_4$
Mol. Wt.: 456.96

To a solution of sodium diethylmalonate [prepared from sodium (13.8 mg, 0.6 mmol) and diethyl malonate (128 μL, 0.84 mmol) in absolute EtOH (0.5 mL)] was added a solution of mesylate (HUP 13) (166 mg, 0.42 mmol) in absolute EtOH (1.5 mL). The mixture was stirred at reflux for 44 h. The cooled reaction mixture was then hydrolyzed with water (2 mL) and concentrated to dryness. Water (15 mL) was then added and the product extracted with AcOEt (3×15 mL). The combined organic layers were dried with $MgSO_4$ and concentrated under reduced pressure to afford a brown residue (209 mg). Purification by flash chromatography (AcOEt/MeOH 10/0 to 9/1, v/v) afforded the desired Huprine)HUP 27) as an almost white solid (112 mg, 58%).

Rf (AcOEt/MeOH 8/2, v/v)=0.61.

$^1$H NMR (300 MHz, MeOD): δ=1.04 (t, J=7.0 Hz, 3H, $CH_3$ of OEt), 1.19 (t, J=7.0 Hz, 3H, $CH_3$ of OEt), 1.70-1.77 (m, 2H, $H_{15}$), 1.80-1.86 (m, 2H, $H_{14}$), 1.92.-2.02 (m, 2H, $H_{10}$, $H_{13}$), 2.06-2.09 (m, 1H, $H_{10}$), 2.38 (d, J=17.1 Hz, 1H, $H_{13}$), 2.65-2.70 (m, 1H, $H_7$), 2.79-2.89 (m, 2H, $H_6$, $H_{16}$), 3.04 (dd, J=17.1 Hz, J=5.3 Hz, 1H, $H_6$), 3.28-3.33 (m, 1H, $H_{11}$), 3.80-3.88 (m, 2H, $CH_2$ of OEt), 4.09 (q, J=7.1 Hz, 2H, $CH_2$ of OEt), 5.51 (d, J=4.3 Hz, 1H, $H_8$), 7.25 (dd, J=9.0 Hz, J=2.1 Hz, 1H, $H_2$), 7.67 (d, J=2.1 Hz, 1H, $H_4$), 8.02 (d, J=9.0 Hz, 1H, $H_1$).

$^{13}$C NMR (75 MHz, MeOD): δ=14.3 ($CH_3$ of OEt), 14.5 ($CH_3$ of OEt), 27.4 ($C_{15}$), 28.4 ($C_{11}$), 29.8 ($C_7$), 30.3 ($C_{10}$), 34.0 ($C_{13}$), 35.3 ($C_{14}$), 40.3 ($C_6$), 51.3 ($C_{16}$), 62.2 ($CH_2$ of OEt), 62.3 ($CH_2$ of OEt), 115.3 ($C_{11a}$ or $C_{12a}$), 117.2 ($C_{11a}$ or $C_{12a}$), 124.8 ($C_1$), 124.9 ($C_2$), 126.4 ($C_4$), 127.9 ($C_8$), 135.6 ($C_3$), 136.2 ($C_9$), 148.1 ($C_{4a}$ or $C_{12}$), 150.0 ($C_{4a}$ or $C_{12}$), 159.2 ($C_{5a}$), 170.8 (C=O), 170.9 (C=O).

MS (ESI+): m/z (%): 457.33 (100), 195.13 (58), 251.00 (48), 459.40 (35), 914.60 (27).

$IC_{50}$ rh-AChE: 6.09±0.42 nM.

$IC_{50}$ rh-BuChE: 319±2 nM.

$IC_{50}$ erythrocyte h-AChE: 46.4 nM.

EXAMPLE 29

2-[2-(12-Amino-3-chloro-6,7,10,11-tetrahydro-7,11-methanocycloocta[b]quinolin-9-yl)ethyl]propane-1,3-diol Trifluoroactic Acid (HUP 28)

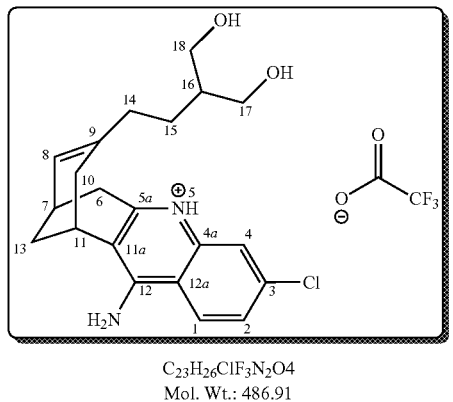

$C_{23}H_{26}ClF_3N_2O_4$
Mol. Wt.: 486.91

To a cooled (0° C.) stirred suspension of anhydrous $LiAlH_4$ (8.6 mg, 214 mol) in dry THF (1 mL) was added dropwise a solution of dimethyl malonate (HUP 26) (46 mg, 107 µmol) in dry THF (4 mL). The solution was stirred 20 h (0° C. to r.t.) then quenched carefully at 0° C. by the addition of water (50 µL), then 5 M NaOH solution (50 µL), then water (150 µL). The reaction mixture was stirred 10 min at r.t. then dried with $Na_2SO_4$. The dried solution and washings (with AcOEt) were filtered and concentrated under reduced pressure to give a yellow solid (97 mg). Purification by preparative HPLC (System B) afforded the trifluoroacetate salt of the desired Huprine (HUP 28) as a light yellow solid (18.0 mg, 45%).

$^1$H NMR (300 MHz, $CDCl_3$): δ=1.32-1.49 (m, 3H, $H_{15}$, $H_{15}$, $H_{16}$), 1.84-2.12 (m, 5H, $H_{10}$, $H_{10}$, $H_{13}$, $H_{14}$, $H_{14}$), 2.52 (d, J=16.9 Hz, 1H, $H_{13}$), 2.80-2.85 (m, 1H, $H_7$), 2.86 (d, J=18.1 Hz, 1H, $H_6$), 3.21 (dd, J=17.9 Hz, J=3.6 Hz, 1H, $H_6$), 3.35-3.52 (m, 3H, $H_{11}$, $H_{18}$, $H_{18}$), 3.73 (t, J=6.6 Hz, 1H, $H_{17}$), 4.25 (dd, J=30.0 Hz, J=5.9 Hz, 1H, $H_{17}$), 5.60-5.66 (m, 1H, $H_8$), 7.59 (dd, J=9.0 Hz, J=2.1 Hz, 1H, $H_2$), 7.73 (d, J=2.1 Hz, 1H, $H_4$), 8.35 (d, J=9.0 Hz, 1H, $H_1$).

$^{13}$C NMR (75 MHz, $CDCl_3$): δ=26.5 ($C_{15}$), 27.5 ($C_{11}$), 28.1 ($C_7$), 29.3 ($C_{10}$), 34.0 ($C_{13}$), 35.6 ($C_{14}$), 36.0 ($C_6$), 40.4 ($C_{16}$), 63.3 ($C_{18}$), 68.9 ($C_{17}$), 115.4 ($C_{11a}$ or $C_{12a}$), 115.5 ($C_{11a}$ or $C_{12a}$), 124.9 ($C_4$), 124.9 ($C_8$), 125.8 ($C_3$), 126.3 ($C_1$), 127.7 ($C_2$), 138.8 ($C_9$), 140.5 ($C_{4a}$ or $C_{12}$), 153.0 ($C_{4a}$ or $C_{12}$), 156.8 ($C_{5a}$).

MS (ESI+): m/z (%): 373.11 (100) [M+H]$^+$, 374.97 (33).

$IC_{50}$ rh-AChE: 24.7±1.2 nM.

$IC_{50}$ rh-BuChE: 37% at 1 µM.

$IC_{50}$ erythrocyte h-AChE: 40.2 nM.

EXAMPLE 30

Methyl 4-(12-Amino-3-chloro-6,7,10,11-tetrahydro-7,11-methano cycloocta[b]quinolin-9-yl)butanoate (HUP 29)

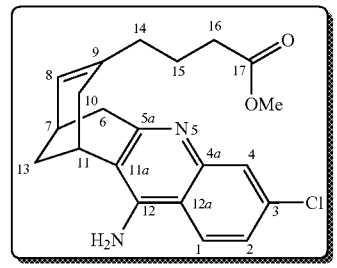

$C_{21}H_{23}ClN_2O_2$
Mol. Wt.: 370.87

A solution of dimethyl malonate (HUP 26) (957 mg, 2.23 mmol), sodium chloride (265 mg, 4.46 mmol) and water (80 µL, 4.40 mmol) in DMSO (2.57 mL) was refluxed 7 h under argon. The cooled reaction mixture was diluted in AcOEt (15 mL) then partionned between water (25 mL) and AcOEt (100 mL). The organic phase was separated and the aqueous one extracted with AcOEt (4×50 mL), DCM (2×50 mL) and again AcOEt (50 mL). The combined organic layers were dried with $Na_2SO_4$ and concentrated under reduced pressure to afford brown oil containing residual DMSO. Purification by flash chromatography (petroleum ether/AcOEt 10/0 to 0/10 then AcOEt/MeOH 9.5/0.5, v/v) afforded the desired Huprine (HUP 29) as yellow crystals (356 mg, 43%).

Rf (AcOEt/MeOH 9/1, v/v)=0.31.

$^1$H NMR (300 MHz, $CDCl_3$): δ=1.51-1.60 (m, 2H, $H_{15}$), 1.80 (t, J=7.5 Hz, 2H, $H_{14}$) 1.92-2.04 (m, 3H, $H_{10}$, $H_{10}$, $H_{13}$), 2.05-2.15 (m, 2H, $H_{16}$), 2.42 (dd, J=16.7 Hz, J=4.1 Hz, 1H, $H_{13}$), 2.70-2.74 (m, 1H, $H_7$), 2.92 (d, J=9.7 Hz, 1H, $H_6$), 3.09 (dd, J=17.5 Hz, J=5.5 Hz, 1H, $H_6$), 3.16-3.19 (m, 1H, $H_{11}$), 3.52 (s, 3H, OMe), 4.86 (brs, $NH_2$), 5.51 (d, J=4.9 Hz, 1H, $H_8$), 7.23 (dd, J=9.0 Hz, J=2.1 Hz, 1H, $H_2$), 7.62 (d, J=9.0 Hz, 1H, $H_1$), 7.82 (d, J=2.1 Hz, 1H, $H_4$).

$^{13}$C NMR (75 MHz, $CDCl_3$): δ=22.5 ($C_{15}$), 27.6 ($C_{11}$), 28.4 ($C_7$), 29.3 ($C_{10}$), 33.1 ($C_{16}$), 33.6 ($C_{13}$), 36.5 ($C_{14}$), 39.9 ($C_6$), 51.4 (OMe), 115.3 ($C_{11a}$ or $C_{12a}$), 115.9 ($C_{11a}$ or $C_{12a}$), 121.7 ($C_1$), 124.6 ($C_2$), 125.8 ($C_8$), 127.6 ($C_4$), 134.3 ($C_3$), 135.0 ($C_9$), 145.8 ($C_{4a}$ or $C_{12}$), 147.4 ($C_{4a}$ or $C_{12}$), 158.8 ($C_{5a}$), 174.2 (C=O).

MS (ESI+): m/z (%): 371.47 (100) [M+H]$^+$, 373.33 (46), 742.87 (7) [2M+2H]$^+$.

$IC_{50}$ rh-AChE: 14.6±1.7 nM.

$IC_{50}$ rh-BuChE: 124±11 nM.

$IC_{50}$ erythrocyte h-AChE: 37.6 nM.

EXAMPLE 31

4-(12-Amino-3-chloro-6,7,10,11-tetrahydro-7,11-methanocycloocta[b]quinolin-9-yl)butan-1-ol (HUP 30)

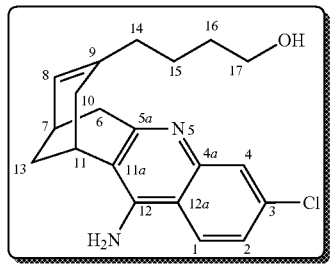

$C_{20}H_{23}ClN_2O$
Mol. Wt.: 342.86

To a cooled (0° C.) stirred suspension of anhydrous LiAlH$_4$ (76 mg, 1.9 mmol) in dry THF (5 mL) was added dropwise a solution of ester (HUP 29) (343 mg, 0.92 mmol) in dry THF (10 mL). The solution was stirred 40 min (0° C. to r.t.) then quenched carefully at 0° C. by the addition of water (0.5 mL), then 5 M NaOH solution (0.5 mL), then water (1.5 mL). The reaction mixture was stirred 10 min at r.t. then dried with Na$_2$SO$_4$. The dried solution and washings (with AcOEt) were filtered and concentrated under reduced pressure to give a yellow solid (534 mg). Purification by flash chromatography (AcOEt/MeOH 100/0 to 92/8) afforded the desired Huprine (HUP 30) as a pale yellow solid (yield calculated at the next step).

Rf (AcOEt/MeOH 8/2, v/v)=0.30.

$^1$H NMR (300 MHz, CDCl$_3$): δ=1.21-1.30 (m, 4H, $H_{14}$, $H_{15}$), 1.75-1.80 (m, 2H, $H_{16}$), 1.90-1.98 (m, 3H, $H_{10}$, $H_{10'}$, $H_{13}$), 2.41 (dd, J=16.9 Hz, J=4.3 Hz, 1H, $H_{13}$), 2.40-2.60 (brs, 1H, OH), 2.68-2.72 (m, 1H, $H_7$), 2.91 (d, J=17.5 Hz, 1H, $H_6$), 3.09 (dd, J=17.4 Hz, J=5.3 Hz, 1H, $H_6$), 3.16-3.19 (m, 1H, $H_{11}$), 3.47 (t, J=17.4 Hz, 2H, $H_{17}$), 4.85 (brs, NH$_2$), 5.48 (d, J=5.1 Hz, 1H, $H_8$), 7.24 (dd, J=9.0 Hz, J=2.1 Hz, 1H, $H_2$), 7.61 (d, J=9.0 Hz, 1H, $H_1$), 7.82 (d, J=2.1 Hz, 1H, $H_4$).

$^{13}$C NMR (75 MHz, CDCl$_3$): δ=23.5 ($C_{15}$), 27.8 ($C_{11}$), 28.4 ($C_7$), 29.4 ($C_{10}$), 32.1 ($C_{14}$), 33.8 ($C_{13}$), 37.0 ($C_{16}$), 40.1 ($C_6$), 62.8 ($C_{17}$), 115.6 ($C_{11a}$ or $C_{12a}$), 115.9 ($C_{11a}$ or $C_{12a}$), 121.5 ($C_1$), 124.8 ($C_2$), 125.3 ($C_8$), 127.8 ($C_4$), 134.4 ($C_3$), 135.8 ($C_9$), 145.6 ($C_{4a}$ or $C_{12}$), 147.5 ($C_{4a}$ or $C_{12}$), 159.0 ($C_{5a}$).

MS (ESI+): m/z (%): 343.40 (100) [M+H]$^+$, 345.27 (35).

IC$_{50}$ rh-AChE: 22.4±1.5 nM.

IC$_{50}$ rh-BuChE: 343±43 nM.

IC$_{50}$ erythrocyte h-AChE: 50.1 nM.

EXAMPLE 32

4-(12-Amino-3-chloro-6,7,10,11-tetrahydro-7,11-methanocycloocta[b]quinolin-9-yl)butyl Methanesulfonate (HUP 31)

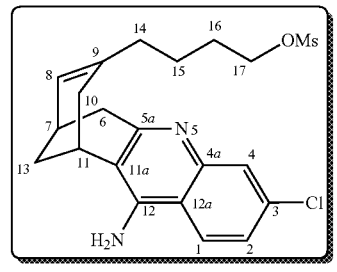

$C_{21}H_{25}ClN_2O_3S$
Mol. Wt.: 420.95

To a cooled (0° C.) stirred solution of alcohol (HUP 30) (332 mg, 0.9 mmol) and triethylamine (253 μL, 1.8 mmol) in dry THF (15 mL) was added Methane sulfonyl chloride (140 μL, 1.8 mmol) dropwise over 5 min. The solution was stirred 30 min (0° C. to r.t.); THF (5 mL) was added to dilute the solution. The reaction mixture was then poured onto a saturated aqueous solution of Na$_2$CO$_3$ and the aqueous phase was extracted with AcOEt (3×40 mL). The combined organic layers were dried with Na$_2$SO$_4$ and concentrated under reduced pressure to give a yellow solid (730 mg). Purification by flash chromatography (AcOEt/MeOH 100/0 to 92/8) afforded the desired Huprine (HUP 31) as a pale yellow solid (296 mg, 87% over two steps).

Rf (AcOEt/MeOH 9/1, v/v)=0.23.

$^1$H NMR (300 MHz, CDCl$_3$): δ=1.32-1.37 (m, 4H, $H_{14}$, $H_{15}$), 1.83-1.87 (m, 2H, $H_{16}$), 1.95-2.02 (m, 3H, $H_{10}$, $H_{10'}$, $H_{13}$), 2.44 (dd, J=16.7 Hz, J=4.7 Hz, 1H, $H_{13}$), 2.74-2.78 (m, 1H, $H_7$), 2.86 (s, 3H, OMs), 2.94 (d, J=17.7 Hz, 1H, $H_6$), 3.14 (dd, J=17.5 Hz, J=5.5 Hz, 1H, $H_6$), 3.20-3.23 (m, 1H, $H_{11}$), 4.00 (m, 2H, $H_{17}$), 4.86 (brs, NH$_2$), 5.54 (d, J=5.3 Hz, 1H, $H_8$), 7.29 (dd, J=9.0 Hz, J=2.1 Hz, 1H, $H_2$), 7.67 (d, J=9.0 Hz, 1H, $H_1$), 7.85 (d, J=2.1 Hz, 1H, $H_4$).

$^{13}$C NMR (75 MHz, CDCl$_3$): δ=23.2 ($C_{15}$), 27.6 ($C_{11}$), 28.3 ($C_{14}$), 28.4 ($C_7$), 29.4 ($C_{10}$), 33.5 ($C_{13}$), 36.4 ($C_{16}$), 37.3 (OMs), 39.9 ($C_6$), 70.1 ($C_{17}$), 115.4 ($C_{11a}$ or $C_{12a}$), 115.9 ($C_{11a}$ or $C_{12a}$), 121.8 ($C_1$), 124.8 ($C_2$), 125.8 ($C_8$), 127.4 ($C_4$), 134.6 ($C_3$), 135.2 ($C_9$), 146.1 ($C_{4a}$ or $C_{12}$), 147.2 ($C_{4a}$ or $C_{12}$), 158.6 ($C_{5a}$).

MS (ESI+): m/z (%): 421.27 (100) [M+H]$^+$, 423.20 (39).

IC$_{50}$ rh-AChE: 4.76±1.68 nM.

IC$_{50}$ rh-BuChE: 243±12 nM.

IC$_{50}$ erythrocyte h-AChE: 13.3 nM.

EXAMPLE 33

9-(4-Azidobutyl)-3-chloro-6,7,10,11-tetrahydro-7,11-methanocycloocta[b]quinolin-12-amine (HUP 32)

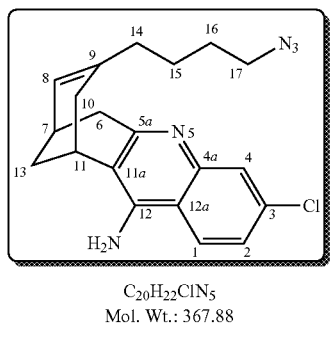

C$_{20}$H$_{22}$ClN$_5$
Mol. Wt.: 367.88

A mixture of mesylate (HUP 31) (282 mg, 0.67 mmol) and sodium azide (163 mg, 2.5 mmol) in dry DMF (3.5 mL) was stirred at 70° C. under argon for 6 h. The cooled reaction mixture was then hydrolyzed with water (5 mL) under stirring. Water (25 mL) was then added and the product extracted with AcOEt (3×30 mL). The combined organic layers were dried with Na$_2$SO$_4$ and concentrated under reduced pressure to afford yellow oil containing residual DMF. Purification by flash chromatography (AcOEt/MeOH 10/0 to 9.5/0.5, v/v) afforded the desired Huprine (HUP 32) as a pale yellow solid (165 mg, 68%).

Rf (AcOEt/MeOH 9/1, v/v)=0.36.

$^1$H NMR (300 MHz, CDCl$_3$): δ=1.28-1.35 (m, 4H, H$_{14}$, H$_{16}$), 1.82 (t, J=6.6 Hz, 2H, H$_{14}$), 1.94-2.02 (m, 3H, H$_{10}$, H$_{10}$, H$_{13}$), 2.45 (dd, J=16.9 Hz, J=4.5 Hz, 1H, H$_{13}$), 2.73-2.77 (m, 1H, H$_7$), 2.93 (d, J=17.5 Hz, 1H, H$_6$), 3.07-3.10 (m, 2H, H$_{17}$), 3.11 (dd, J=17.5 Hz, J=5.6 Hz, 1H, H$_6$), 3.19-3.21 (m, 1H, H$_{11}$), 4.82 (brs, NH$_2$), 5.52 (d, J=5.3 Hz, 1H, H$_8$), 7.27 (dd, J=9.0 Hz, J=2.1 Hz, 1H, H$_2$), 7.63 (d, J=9.0 Hz, 1H, H$_1$), 7.84 (d, J=2.1 Hz, 1H, H$_4$).

$^{13}$C NMR (75 MHz, CDCl$_3$): δ=24.4 (C$_{15}$), 27.7 (C$_{11}$), 28.2 (C$_{16}$), 28.4 (C$_7$), 29.4 (C$_{10}$), 33.7 (C$_{13}$), 36.8 (C$_{14}$), 39.9 (C$_6$), 51.3 (C$_{17}$), 115.4 (C$_{11a}$ or C$_{12a}$), 115.9 (C$_{11a}$ or C$_{12a}$), 121.6 (C$_1$), 124.8 (C$_2$), 125.5 (C$_8$), 127.7 (C$_4$), 134.4 (C$_3$), 135.4 (C$_9$), 145.8 (C$_{4a}$ or C$_{12}$), 147.4 (C$_{4a}$ or C$_{12}$), 158.8 (C$_{5a}$).

MS (ESI+): m/z (%): 368.27 (100) [M+H]$^+$, 370.20 (33).

IC$_{50}$ rh-AChE: 13.1±4.7 nM.

IC$_{50}$ rh-BuChE: 260±12 nM.

IC$_{50}$ erythrocyte h-AChE: 68.1 nM.

EXAMPLE 34

Methyl 1-[4-(12-Amino-3-chloro-6,7,10,11-tetrahydro-7,11-methano cycloocta[b]quinolin-9-yl)butyl]-1H-1,2,3-triazole-4-carboxylate (HUP 33)

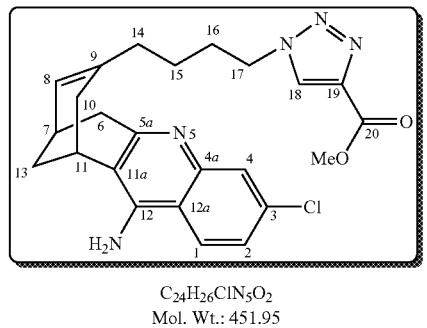

C$_{24}$H$_{26}$ClN$_5$O$_2$
Mol. Wt.: 451.95

A mixture of azide (HUP 32) (74 mg, 0.20 mmol), copper iodide (7.6 mg, 0.04 mmol) and methyl propionate (23 µL, 0.25 mmol) in MeCN (4 mL) was stirred at r.t. with light protection for 23 h. The reaction mixture was concentrated to dryness then purified by flash chromatography (AcOEt/MeOH/[EtOH/NEt$_3$, 9/1]100/0/0 to 92/4/4, v/v/v) to afford the desired Huprine (HUP 33) as white crystals (82 mg, 91%).

Rf (AcOEt/MeOH 8/2, v/v)=0.35.

$^1$H NMR (300 MHz, MeOD): δ=1.22-1.26 (m, 2H, H$_{15}$), 1.45-1.63 (m, 2H, H$_{16}$), 1.85-1.94 (m, 3H, H$_{14}$, H$_{14}$, H$_{10}$), 1.97-2.06 (m, 2H, H$_{10}$, H$_{13}$), 2.37 (dd, J=17.1 Hz, J=4.0 Hz, 1H, H$_{13}$), 2.68-2.71 (m, 1H, H$_7$), 2.82 (d, J=17.5 Hz, 1H, H$_6$), 3.04 (dd, J=17.5 Hz, J=5.5 Hz, 1H, H$_6$), 3.30-3.33 (m, 1H, H$_{11}$), 3.91 (s, 3H, MeO), 4.15 (t, J=7.2 Hz, 2H, H$_{17}$), 5.54 (d, J=5.3 Hz, 1H, H$_8$), 7.25 (dd, J=9.0 Hz, J=2.1 Hz, 1H, H$_2$), 7.62 (d, J=9.0 Hz, 1H, H$_4$), 8.01 (d, J=2.1 Hz, 1H, H$_1$), 8.26 (s, 1H, H$_{18}$).

$^{13}$C NMR (75 MHz, MeOD): δ=24.9 (C$_{15}$), 28.3 (C$_{11}$), 29.7 (C$_7$), 29.9 (C$_{16}$), 30.4 (C$_{10}$), 34.1 (C$_{13}$), 37.3 (C$_{14}$), 40.3 (C$_6$), 51.2 (C$_{17}$), 52.7 (MeO), 115.5 (C$_{11a}$ or C$_{12a}$), 117.0 (C$_{11a}$ or C$_{12a}$), 124.7 (C$_1$), 125.0 (C$_2$), 126.1 (C$_4$), 126.7 (C$_8$), 129.2 (C$_{18}$), 135.8 (C$_3$), 137.2 (C$_9$), 140.2 (C$_{4a}$ or C$_{12}$), 147.8 (C$_{4a}$ or C$_{12}$), 150.2 (C$_{19}$), 158.8 (C$_{5a}$), 162.3 (C$_{20}$).

MS (ESI+): m/z (%): 452.27 (100) [M+H]$^+$, 454.27 (36).

IC$_{50}$ rh-AChE: 0.34±0.12 nM.

IC$_{50}$ rh-BuChE: 291±25 nM.

IC$_{50}$ erythrocyte h-AChE: 10.7 nM.

EXAMPLE 35

{1-[4-(12-Amino-3-chloro-6,7,10,11-tetrahydro-7,11-methanocycloocta[b]quinolin-9-yl)butyl]-1H-1,2,3-triazol-4-yl}methanol Trifluoroacetic Acid (HUP 34)

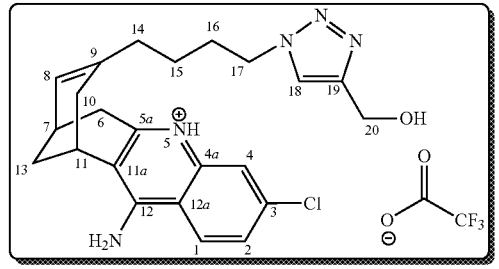

C$_{25}$H$_{27}$ClF$_3$N$_5$O$_3$
Mol. Wt.: 537.96

To a cooled (0° C.) stirred suspension of anhydrous LiAlH$_4$ (13.2 mg, 330 μmol) in dry THF (0.5 mL) was added dropwise a solution of triazole (HUP 33) (58 mg, 128 μmol) in dry THF (3.5 mL). The solution was stirred 20 min (0° C. to r.t.) then quenched at 0° C. by the addition of water (100 μL), then 5 M NaOH solution (100 μL), then water (300 μL). The reaction mixture was stirred 10 min at r.t. then concentrated to dryness and purified by preparative HPLC (system B) to afford the desired Huprine (HUP 34) as a white solid (37 mg, 67%).

$^1$H NMR (300 MHz, MeOD): δ=1.26-1.33 (m, 2H, H$_{15}$), 1.58-1.72 (m, 2H, H$_{16}$), 1.90-2.02 (m, 4H, H$_{14}$, H$_{14}$, H$_{10}$, H$_{13}$), 2.05-2.10 (m, 1H, H$_{10}$), 2.45 (dd, J=17.9 Hz, J=4.1 Hz, 1H, H$_{13}$), 2.78-2.81 (m, 1H, H$_7$), 2.86 (d, J=17.9 Hz, 1H, H$_6$), 3.20 (dd, J=17.7 Hz, J=5.5 Hz, 1H, H$_6$), 3.36-3.40 (m, 1H, H$_{11}$), 4.23 (td, J=7.2 Hz, J=1.9 Hz, 2H, H$_{17}$), 4.66 (s, 2H, H$_{20}$), 5.59 (d, J=4.9 Hz, 1H, H$_8$), 7.57 (dd, J=9.2 Hz, J=2.1 Hz, 1H, H$_2$), 7.72 (d, J=9.2 Hz, 1H, H$_4$), 7.79 (s, 1H, H$_{18}$), 8.34 (d, J=2.1 Hz, 1H, H$_1$)

$^{13}$C NMR (75 MHz, MeOD): δ=25.0 (C$_{15}$), 27.5 (C$_{11}$), 28.1 (C$_7$), 29.3 (C$_{10}$), 30.3 (C$_{16}$), 33.7 (C$_{13}$), 35.9 (C$_6$), 37.2 (C$_{14}$), 50.9 (C$_{17}$), 56.4 (C$_{20}$), 115.3 (C$_{11a}$ or C$_{12a}$), 115.4 (C$_{11a}$ or C$_{12a}$), 119.2 (C$_4$), 124.1 (C$_{18}$), 125.5 (C$_8$), 126.3 (C$_1$), 127.7 (C$_2$), 138.0 (C$_3$), 139.5 (C$_9$), 140.4 (C$_{4a}$ or C$_{12}$), 148.9 (C$_{4a}$ or C$_{12}$), 153.0 (C$_{19}$), 156.7 (C$_{5a}$).

MS (ESI+): m/z (%): 424.33 (100) [M+H]$^+$, 426.27 (40).
IC$_{50}$ rh-AChE: 0.26±0.08 nM.
IC$_{50}$ rh-BuChE: 213±18 nM.
IC$_{50}$ erythrocyte h-AChE: 6.91 nM.

EXAMPLE 36

{1-[4-(12-Amino-3-chloro-6,7,10,11-tetrahydro-7,11-methanocycloocta[b]quinolin-9-yl)butyl]-1H-1,2,3-triazol-4-yl}methyl Trifluoroacetate (HUP 35)

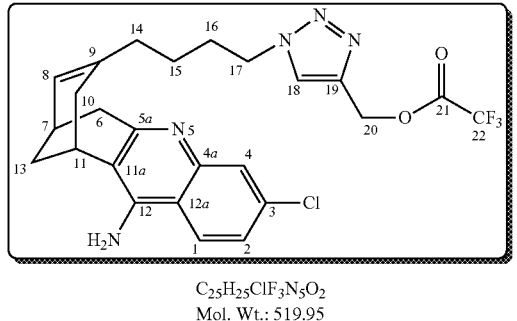

C$_{25}$H$_{25}$ClF$_3$N$_5$O$_2$
Mol. Wt.: 519.95

To a cooled (0° C.) stirred solution of the trifluoroacetate salt of alcohol (HUP 34) (16 mg, 25.8 μmol) and trietylamine (14.7 μL, 105 μmol) in dry THF (1 mL) was added dropwise trifluoroacetic anhydride (8.7 μL, 62.8 μmol). The solution was stirred 40 min at r.t. then concentrated to dryness. The crude mixture was purified by flash chromatography (cyclohexane/AcOEt/MeOH 80/20/0 to 0/88/12, v/v/v, with 1% of Et$_3$N) to afford the desired Huprine (HUP 35) as a white solid (8.0 mg, 60%).

Rf (AcOEt/MeOH 8/2, v/v)=0.25.

$^1$H NMR (300 MHz, CDCl$_3$): δ=0.83-0.98 (m, 2H, H$_{15}$), 1.23-1.35 (m, 2H, H$_{16}$), 1.80-1.88 (m, 3H, H$_{10}$, H$_{10}$, H$_{13}$), 1.97-2.01 (m, 2H, H$_{14}$), 2.30 (dd, J=17.5 Hz, J=5.1 Hz, 1H, H$_{13}$), 2.76-2.79 (m, 1H, H$_7$), 3.09 (d, J=16.4 Hz, 1H, H$_6$), 3.21 (dd, J=17.9 Hz, J=5.3 Hz, 1H, H$_6$), 3.41-3.44 (m, 1H, H$_{11}$), 3.90 (t, J=7.0 Hz, 2H, H$_{17}$), 4.72 (d, J=3.8 Hz, 2H, H$_{20}$), 5.56 (d, J=5.1 Hz, 1H, H$_8$), 7.12 (s, 1H, H$_{18}$), 7.39 (dd, J=9.0 Hz, J=1.9 Hz, 1H, H$_2$), 7.78 (d, J=9.0 Hz, 1H, H$_4$), 7.96 (d, J=1.8 Hz, 1H, H$_1$).

$^{13}$C NMR (75 MHz, CDCl$_3$): δ=23.1 (C$_{15}$), 27.6 (C$_{16}$), 28.2 (C$_7$), 28.4 (C$_{14}$), 28.8 (C$_{11}$), 34.4 (C$_{13}$), 35.5 (C$_{10}$), 40.3 (C$_6$), 49.9 (C$_{17}$), 56.3 (C$_{20}$), 115.5 (C$_{11a}$ or C$_{12a}$), 117.0 (C$_{11a}$ or C$_{12a}$), 122.4 (C$_{18}$), 122.7 (?), 123.9 (C$_1$), 126.8 (C$_8$), 127.5 (C$_2$), 127.5 (C$_4$), 135.0 (C$_3$), 135.4 (C$_9$), 147.3 (C$_{4a}$ or C$_{12}$), 156.4 (C$_{19}$), 156.9 (C$_{5a}$).

$^{19}$F NMR (282 MHz, CDCl$_3$): δ=−74.7.
MS (ESI+): m/z (%): 520.20 (100) [M+H]$^+$, 522.33 (36).
IC$_{50}$ rh-AChE: 34.6±2.6 nM.
IC$_{50}$ rh-BuChE: 23% at 1 μM.
IC$_{50}$ erythrocyte h-AChE: 69.8 nM.

EXAMPLE 37

Ethyl 4-(12-Amino-3-chloro-6-methylene-6,7,10,11-tetrahydro-7,11-methanocycloocta[b]quinolin-9-yl)butanoate (HUP 36)

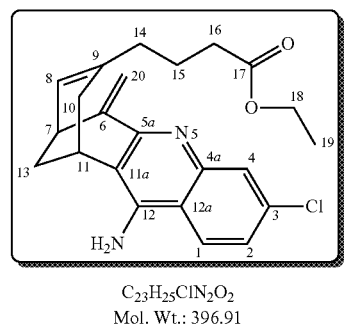

C$_{23}$H$_{25}$ClN$_2$O$_2$
Mol. Wt.: 396.91

To a solution of diethylmalonate (HUP 27) (1.00 g, 2.2 mmol) in DMSO (10 mL) and water (200 μL) was added lithium chloride (400 mg, 9.5 mmol). The suspension was refluxed for 17 h then cooled to r.t. and diluted with AcOEt (20 mL). The organic phase was washed with brine (40 mL), NaHCO$_3$ saturated solution (40 mL) and water (40 mL), dried with Na$_2$SO$_4$ to give a brown solid. Purification by flash chromatography (AcOEt/MeOH 10/0 to 9/1, v/v) afforded the desired Huprine (HUP 36) as a yellow solid (295 mg, 34%).

Rf (AcOEt/MeOH 8/2, v/v)=0.88.

$^1$H NMR (300 MHz, CDCl$_3$): δ=1.16 (t, J=7.2 Hz, 3H, H$_{19}$), 1.53-1.59 (m, 2H, H$_{15}$), 1.56 (t, J=7.5 Hz, 2H, H$_{14}$), 1.90-2.10 (m, 5H, H$_{16}$, H$_{16}$, H$_{10}$, H$_{10}$, H$_{13}$), 2.43 (dd, J=17.0 Hz, J=3.0 Hz, 1H, H$_{13}$), 3.18-3.21 (m, 1H, H$_7$), 3.26-3.30 (m, 1H, H$_{11}$), 3.99 (q, J=6.0 Hz, 2H, H$_{18}$), 4.81 (brs, 2H, NH$_2$), 5.19 (d, J=2.2 Hz, 1H, H$_{20}$), 5.48 (d, J=5.3 Hz, 1H, H$_8$), 6.31 (d, J=2.1 Hz, 1H, H$_{20}$), 7.22 (dd, J=9.0 Hz, J=2.1 Hz, 1H, H$_2$), 7.56 (d, J=9.0 Hz, 1H, H$_1$), 7.89 (d, J=2.1 Hz, 1H, H$_4$).

$^{13}$C NMR (75 MHz, CDCl$_3$): δ=14.2 (C$_{19}$), 22.5 (C$_{15}$), 28.2 (C$_7$), 29.7 (C$_{16}$), 32.8 (C$_{10}$), 33.5 (C$_{13}$), 36.7 (C$_{14}$), 38.0 (C$_{11}$), 60.2 (C$_{18}$), 112.5 (C$_{20}$), 114.9 (C$_{11a}$ or C$_{12a}$), 116.4 (C$_{11a}$ or C$_{12a}$), 121.5 (C$_1$), 124.8 (2C, C$_2$, C$_8$), 128.6 (C$_4$), 134.2 (C$_3$), 134.8 (C$_9$), 146.0 (C$_{4a}$ or C$_{12}$), 146.6 (C$_{4a}$ or C$_{12}$), 147.6 (C$_{5a}$), 157.3 (C$_6$), 173.7 (C$_{17}$).

MS (ESI+): m/z (%): 397.32 (100) [M+H]$^+$, 399.31 (35), 400.31 (9).
IC$_{50}$ rh-AChE: 90.6±8.4 nM.
IC$_{50}$ rh-BuChE: 11% at 1 μM.

EXAMPLE 38

4-(12-Amino-3-chloro-6-methylene-6,7,10,11-tetrahydro-7,11-methano cycloocta[b]quinolin-9-yl)butan-1-ol Trifluoroacetic Acid (HUP 37)

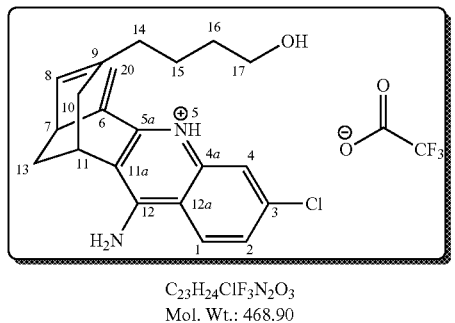

$C_{23}H_{24}ClF_3N_2O_3$
Mol. Wt.: 468.90

To a cooled (0° C.) stirred suspension of anhydrous LiAlH$_4$ (30.4 mg, 760 µmol) in dry THF (2 mL) was added dropwise a solution of ester (HUP 36) (151 mg, 380 µmol) in dry THF (5 mL). The solution was stirred 20 h (0° C. to r.t.) then quenched carefully at 0° C. by the addition of water (150 µL), then 5 M NaOH solution (150 µL), then water (450 µL). The reaction mixture was stirred 10 min at r.t. then dried with Na$_2$SO$_4$. The dried solution and washings (with AcOEt) were filtered and concentrated under reduced pressure to give a yellow solid (276 mg). Purification by two successive flash chromatographies (AcOEt/MeOH 100/0 to 95/5, v/v) afforded a pale yellow solid (55 mg) still containing impurities. Purification by preparative HPLC (System B) afforded a pale orange solid (16.0 mg, 9%) containing the trifluoroacetate salt of the desired Huprine (HUP 37) (70% in NMR) along with another inseparable isomer (30% in NMR).

Rf (free base, AcOEt/MeOH 9/1, v/v)=0.50.

$^1$H NMR (300 MHz, CDCl$_3$): δ=1.23-1.45 (m, 4H, H$_{14}$, H$_{15}$), 1.88-2.00 (m, 2H, H$_{16}$), 2.06-2.19 (m, 3H, H$_{10}$, H$_{10}$, H$_{13}$), 2.57 (d, J=14.3 Hz, 1H, H$_{13}$), 3.30-3.49 (m, 6H, H$_7$, H$_6$, H$_6$, H$_{11}$, H$_{17}$, H$_{17}$), 5.54 (m, 1H, H$_8$), 5.75 (d, J=2.3 Hz, 1H, H$_{18}$), 6.13 (d, J=2.3 Hz, 1H, H$_{18}$), 7.60 (dd, J=9.0 Hz, J=1.9 Hz, 1H, H$_2$), 8.01 (d, J=1.9 Hz, 1H, H$_4$), 8.36 (d, J=9.0 Hz, 1H, H$_1$).

$^{13}$C NMR (75 MHz, CDCl$_3$): δ=24.8 (C$_{15}$), 28.5 (C$_7$), 30.6 (C$_{14}$), 32.8 (C$_{10}$), 33.4 (C$_{13}$), 37.9 (C$_{16}$), 38.9 (C$_{11}$), 62.5 (C$_{17}$), 115.4 (C$_{11a}$ or C$_{12a}$), 115.6 (C$_{11a}$ or C$_{12a}$), 117.3 (C$_{18}$), 119.8 (C$_4$), 123.7 (C$_8$), 126.2 (C$_1$), 128.0 (C$_2$), 138.9 (C$_3$), 139.8 (C$_9$), 141.0 (C$_{4a}$ or C$_{12}$), 142.9 (C$_{4a}$ or C$_{12}$), 146.7 (C$_{5a}$), 157.4 (C$_6$).

IC$_{50}$ rh-AChE: 256±34 nM.

IC$_{50}$ rh-BuChE: 15% at 1 µM.

EXAMPLE 39

{1-[4-(12-Amino-6,7,10,11-tetrahydro-7,11-methanocycloocta[b]quinolin-9-yl)butyl]-1H-1,2,3-triazol-4-yl}methanol Trifluoroacetic Acid (HUP 38)

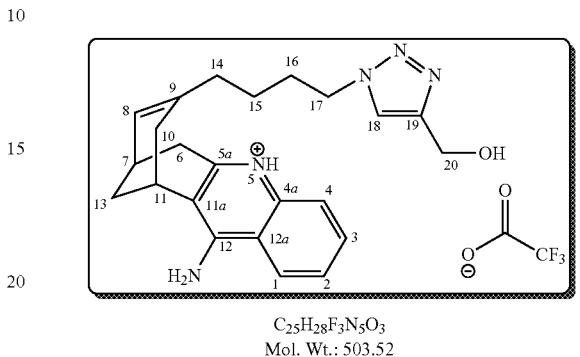

$C_{25}H_{28}F_3N_5O_3$
Mol. Wt.: 503.52

To a cooled (0° C.) stirred suspension of anhydrous LiAlH$_4$ (13.2 mg, 330 mol) in dry THF (0.5 mL) was added dropwise a solution of triazole (HUP 33) (58 mg, 128 µmol) in dry THF (3.5 mL). The solution was stirred 20 min (0° C. to r.t.) then quenched at 0° C. by the addition of water (100 µL), then 5 M NaOH solution (100 µL), then water (300 µL). The reaction mixture was stirred 10 min at r.t. then concentrated to dryness and purified by preparative HPLC (MeOH/TFA 0.1%) to afford the desired Huprine (HUP 38) an off white solid (7.1 mg, 11%).

$^1$H NMR (300 MHz, MeOD): δ=1.26-1.34 (m, 2H, H$_{15}$), 1.59-1.72 (m, 2H, H$_{16}$), 1.91-2.12 (m, 5H, H$_{14}$, H$_{14}$, H$_{10}$, H$_{13}$, H$_{10}$), 2.46 (dd, J=17.7 Hz, J=4.3 Hz, 1H, H$_{13}$), 2.79-2.81 (m, 1H, H$_7$), 2.88 (d, J=17.9 Hz, 1H, H$_6$), 3.21 (dd, J=17.9 Hz, J=5.3 Hz, 1H, H$_6$), 3.38-3.41 (m, 1H, H$_{11}$), 4.23 (td, J=7.2 Hz, J=1.9 Hz, 2H, H$_{17}$), 4.66 (s, 2H, H$_{20}$), 5.59 (d, J=4.7 Hz, 1H, H$_8$), 7.61 (td, J=8.1 Hz, J=0.9 Hz, 1H, H$_2$), 7.71 (d, J=8.3 Hz, 1H, H$_4$), 7.77 (s, 1H, H$_{18}$), 7.86 (td, J=8.3 Hz, J=1.1 Hz, 1H, H$_1$), 8.34 (d, J=8.5 Hz, 1H, H$_1$).

$^{13}$C NMR (75 MHz, MeOD): δ=25.1 (C$_{15}$), 27.6 (C$_{11}$), 28.3 (C$_7$), 29.5 (C$_{10}$), 30.4 (C$_{16}$), 33.9 (C$_{13}$), 35.9 (C$_6$), 37.3 (C$_{14}$), 51.0 (C$_{17}$), 56.4 (C$_{20}$), 114.9 (C$_{11a}$ or C$_{12a}$), 116.8 (C$_{11a}$ or C$_{12a}$), 120.1 (C$_4$), 124.1 (C$_{18}$), 124.2 (C$_1$), 125.6 (C$_8$), 127.2 (C$_2$), 134.5 (C$_3$), 138.1 (C$_9$), 138.1 (C$_{4a}$ or C$_{12}$), 138.9 (C$_{4a}$ or C$_{12}$), 152.4 (C$_{19}$), 156.8 (C$_{5a}$).

MS (ESI+): m/z (%): 390.27 (100) [M+H]$^+$, 391.27 (28).

IC$_{50}$ rh-AChE: 94.1±2.8 nM.

IC$_{50}$ rh-BuChE: 357±16 nM.

EXAMPLE 40

2-(12-Amino-6,7,10,11-tetrahydro-7,11-methanocycloocta[b]quinolin-9-yl) Ethyl Methanesulfonate (HUP 39)

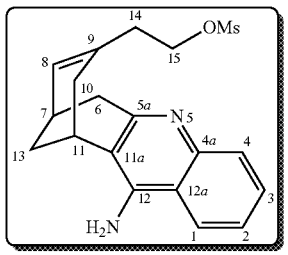

$C_{19}H_{22}N_2O_3S$
Mol. Wt.: 358.45

To a cooled (0° C.) stirred solution of alcohol (HUP 2) (393 mg, 1 mmol) and triethylamine (140 µL, 1.5 mmol) in dry THF/dioxane mixture (90 mL, 2/1, v/v) was added methane sulfonyl chloride (80 µL, 1.5 mmol) dropwise over 5 min. The solution was stirred 1 h (0° C. to r.t.). The reaction mixture was concentrated almost to dryness under reduced pressure then poured onto a saturated aqueous solution of NaHCO$_3$. The aqueous phase was extracted with AcOEt (3×25 mL). The combined organic layers were dried with Na$_2$SO$_4$ and concentrated under reduced pressure to afford a yellow solid. Purification by flash chromatography (petroleum ether/AcOEt 3/7 then AcOEt then AcOEt/MeOH 9/1) afforded the desired Huprine (HUP 39) as an off white solid (322 mg, 90%).

Rf (AcOEt/MeOH 8/2, v/v)=0.11.

$^1$H NMR (300 MHz, CDCl$_3$): δ=1.82-1.95 (m, 3H, H$_{10}$, H$_{10'}$, H$_{13}$), 2.15 (t, J=6.4 Hz, 2H, H$_{14}$), 2.38 (dd, J=16.6 Hz, J=3.2 Hz, 1H, H$_{13}$), 2.54 (s, 3H, OMs), 2.67-2.73 (m, 1H, H$_7$), 2.90 (d, J=17.3 Hz, 1H, H$_6$), 3.08 (dd, J=17.5 Hz, J=5.5 Hz, 1H, H$_6$), 3.14-3.19 (m, 1H, H$_{11}$), 4.01 (t, J=6.6 Hz, 2H, H$_{15}$), 5.12 (brs, 2H, NH$_2$), 5.58 (d, J=5.3 Hz, 1H, H$_8$), 7.26 (t, J=7.5 Hz, 1H, H$_2$), 7.28 (td, J=7.0 Hz, J=0.7 Hz, 1H, H$_3$), 7.7-7.80 (m, 2H, H$_4$, H$_1$).

$^{13}$C NMR (75 MHz, CDCl$_3$): δ=27.2 (C$_{11}$), 28.3 (C$_7$), 28.9 (C$_{10}$), 33.7 (C$_{13}$), 36.4 (C$_{14}$), 36.7 (OMs), 39.3 (C$_6$), 68.2 (C$_{15}$), 114.3 (C$_{11a}$ or C$_{12a}$), 117.3 (C$_{11a}$ or C$_{12a}$), 120.4 (C$_1$), 123.9 (C$_2$), 128.0 (C$_4$), 128.4 (C$_8$), 128.8 (C$_3$), 131.2 (C$_9$), 146.3 (C$_{4a}$ or C$_{12}$), 146.4 (C$_{4a}$ or C$_{12}$), 156.7 (C$_{5a}$).

MS (ESI+): m/z (%): 359.27 (100) [M+H]$^+$, 360.20 (23).

IC$_{50}$ rh-AChE: 149±6 nM.

IC$_{50}$ rh-BuChE: 171±4 nM.

EXAMPLE 41

9-(2-Azidoethyl)-6,7,10,11-tetrahydro-7,11-methanocycloocta[b]quinolin-12-amine (HUP 40)

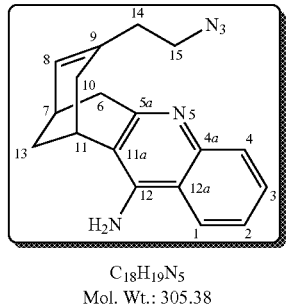

$C_{18}H_{19}N_5$
Mol. Wt.: 305.38

A suspension of mesylate (HUP 39) (286 mg, 0.8 mmol) and sodium azide (208 mg, 3.2 mmol) in dry DMF (2.5 mL) was stirred under argon at 80° C. for 6 h30. The reaction mixture was then cooled to r.t. and water (5 mL) was added under stirring. Additional water (35 mL) and 30% aqueous Na$_2$CO$_3$ solution (10 mL) were added. Aqueous phase was extracted with AcOEt (3×30 mL) and the combined organic layers were dried with Na$_2$SO$_4$. Concentration under reduced pressure afforded a yellow oil. Purification by flash chromatography (AcOEt/MeOH 100/0 to 95/5, v/v, then AcOEt/EtOH/NEt$_3$ 90/9/1, v/v/v) afforded the desired Huprine (HUP 40) as a pale yellow solid (102 mg, 42%).

Rf (AcOEt/MeOH 8/2, v/v)=0.11.

$^1$H NMR (300 MHz, MeOD): δ=1.84-2.10 (m, 5H, H$_{10}$, H$_{10'}$, H$_{13}$, H$_{14}$, H$_{14'}$), 2.46 (dd, J=17.7 Hz, J=4.7 Hz, 1H, H$_{13}$), 2.65-2.70 (m, 1H, H$_7$), 2.86 (d, J=17.5 Hz, 1H, H$_6$), 3.04 (dd, J=17.5 Hz, J=5.5 Hz, 1H, H$_6$), 3.07-3.16 (m, 2H, H$_{15}$), 3.29-3.34 (m, 1H, H$_{11}$), 5.62 (d, J=5.5 Hz, 1H, H$_8$), 7.33 (td, J=6.8 Hz, J=1.1 Hz, 1H, H$_2$), 7.54 (td, J=7.0 Hz, J=1.3 Hz, 1H, H$_3$), 7.68 (dd, J=8.5 Hz, J=0.6 Hz, 1H, H$_4$), 8.05 (dd, J=8.5 Hz, J=0.7 Hz, 1H, H$_1$).

$^{13}$C NMR (75 MHz, MeOD): δ=28.1 (C$_{11}$), 29.5 (C$_7$), 30.0 (C$_{10}$), 34.6 (C$_{13}$), 37.7 (C$_{14}$), 39.2 (C$_6$), 50.3 (C$_{15}$), 114.8 (C$_{11a}$ or C$_{12a}$), 118.3 (C$_{11a}$ or C$_{12a}$), 122.8 (C$_1$), 124.9 (C$_2$), 126.3 (C$_4$), 128.2 (C$_8$), 130.5 (C$_3$), 134.8 (C$_9$), 146.0 (C$_{4a}$ or C$_{12}$), 150.8 (C$_{4a}$ or C$_{12}$), 156.7 (C$_{5a}$).

MS (ESI+): m/z (%): 306.25 (100) [M+H]$^+$, 307.11 (20).

EXAMPLE 42

9-(2-Aminoethyl)-6,7,10,11-tetrahydro-7,11-methanocycloocta[b]quinolin-12-amine Dihydrochloride (HUP 41)

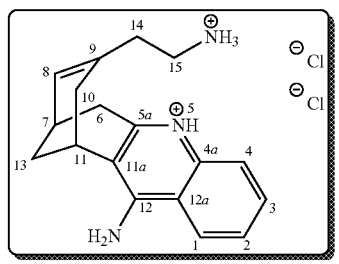

$C_{18}H_{23}Cl_2N_3$
Mol. Wt.: 352.30

A solution of azide (HUP 40) (100 mg, 327 µmol) and triphenylphosphine (86 mg, 327 µmol) in THF (1.6 mL) was stirred 30 min at 0° C. and 1 h (0° C. to r.t.). Water (16 µL) was then added at 0° C. and the mixture was stirred at r.t. for 17 h. The reaction mixture was concentrated to dryness then purified by preparative HPLC (System B) and concentrated under reduced pressure to afford the ditrifluoroacetate salt of the desired Huprine (HUP 41) as a white solid (72 mg, 43%). The ditrifluoroacetate salt was suspended in CHCl$_3$ (3 mL) then converted into free base by addition of ethanol/triethylamine 9/1, v/v solution (2 mL). The solvents were removed and the salts precipitated in chloroform/acetone 3/2, v/v, filtered and washed with CHCl$_3$. The solvents were removed, then the residue was dissolved in MeOH (4 mL) and neutralized by addition of concentrated 37% aqueous HCl solution (2 mL). Evaporation of the solvents afforded the dihydrochloride of the desired Huprine (HUP 41) as a pale grey solid (36 mg, 31%).

$^1$H NMR (300 MHz, MeOD): δ=1.93-2.16 (m, 3H, H$_{10}$, H$_{13}$, H$_{10}$), 2.23 (t, J=7.7 Hz, 2H, H$_{14}$), 2.60 (dd, J=17.7 Hz, J=3.6 Hz, 1H, H$_{13}$), 2.83-2.87 (m, 1H, H$_7$), 2.88-2.97 (m, 3H, H$_6$, H$_{15}$, H$_{15}$), 3.21 (dd, J=18.1 Hz, J=5.5 Hz, 1H, H$_6$), 3.41-3.45 (m, 1H, H$_{11}$), 5.74 (d, J=4.5 Hz, 1H, H$_8$), 7.57 (t, J=7.3 Hz, 1H, H$_2$), 7.71 (d, J=7.9 Hz, 1H, H$_4$), 7.80 (td, J=7.0 Hz, J=0.9 Hz, 1H, H$_3$), 7.32 (d, J=8.5 Hz, 1H, H$_1$).

$^{13}$C NMR (75 MHz, MeOD): δ=27.2 (C$_{11}$), 28.1 (C$_7$), 28.9 (C$_{10}$), 34.1 (C$_{13}$), 35.4 (C$_{14}$), 35.8 (C$_6$), 38.7 (C$_{15}$), 114.4 (C$_{11a}$ or C$_{12a}$), 116.7 (C$_{11a}$ or C$_{12a}$), 120.0 (C$_4$), 124.2 (C$_1$), 127.1 (C$_2$), 128.0 (C$_8$), 134.1 (C$_9$), 134.3 (C$_3$), 138.9 (C$_{4a}$ or C$_{12}$), 152.0 (C$_{4a}$ or C$_{12}$), 156.7 (C$_{5a}$).

MS (ESI+): m/z (%): 280.30 (100) [M+H]$^+$, 281.23 (24), 140.59 (10) [M/2+H]$^{2+}$.

EXAMPLE 43

Ethyl (3,12-dichloro-6,7,10,11-tetrahydro-7,11-methanocycloocta[b]quinolin-9-yl)acetate (HUP 42)

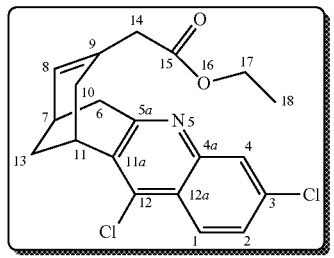

C$_{20}$H$_{19}$Cl$_2$NO$_2$
Mol. Wt.: 376.28

A mixture of 3-ethylacetate-2-oxa-1-adamantyl methanesulfonate (318 mg, 1.0 mmol), anhydrous aluminium trichloride (160 mg, 1.2 mmol) and 4 Å molecular sieve in distilled 1,2-dichloroethane (3 mL) was stirred at reflux temperature for 1 h, then cooled to 30° C. To the reaction mixture was added slowly a solution of 4-chloro-2-aminobenzoic acid (206 mg, 1.2 mmol) in dioxane (5 mL). The white precipitate which formed was stirred at r.t. for 15 min then the mixture was cooled to 0° C. and phosphorous oxychloride (1.86 mL) was added dropwise. The reaction mixture was stirred 5 h at r.t. then 15 h at 90° C. then hydrolyzed at 0° C. with slow addition of water (5 mL), THF (5 mL) and 5 M aqueous NaOH solution (12 mL). After 30 min stirring at r.t., the salts were filtered and the residue washed with DCM. The filtrate was extracted with DCM (3×30 mL). The combined organic layers were dried with Na2SO4 and concentrated under reduced pressure to afford a yellow oil. Purification by flash chromatography (cyclohexane/AcOEt 10/0 to 8/2, v/v) afforded the desired Huprine as a pale yellow solid (165 mg, 44%).

Rf (cyclohexane/AcOEt 7/3, v/v)=0.59.

IR (KBr): ν=2930, 1734, 1608, 1545, 1474, 1396, 1369, 1332, 1294, 1253, 1153, 1074, 1033, 929, 770 cm-1.

$^1$H NMR (300 MHz, CDCl$_3$): δ=0.96 (t, J=7.1 Hz, 3H, H$_{18}$), 1.92-1.99 (m, 1H, H$_{10}$), 2.07-2.14 (m, 1H, H$_{10}$), 2.19 (d, J=17.7 Hz, 1H, H$_{13}$), 2.66 (dd, J=17.7 Hz, J=5.5 Hz, 1H, H$_{13}$), 2.74-2.88 (m, 2H, H7, H$_{14}$), 3.09 (dt, J=17.7 Hz, J=1.9 Hz, 1H, H$_6$), 3.20 (dd, J=17.9 Hz, J=5.3 Hz, 1H, H$_6$), 3.74-3.78 (m, 1H, H$_{11}$), 3.92 (qd, J=7.1 Hz, J=2.3 Hz, 2H, H$_{17}$), 5.69 (d, J=5.5 Hz, 1H, H$_8$), 7.44 (dd, J=9.0 Hz, J=1.9 Hz, 1H, H$_2$), 7.94 (d, J=1.9 Hz, 1H, H$_4$), 8.07 (d, J=9.0 Hz, 1H, H$_1$).

$^{13}$C NMR (75 MHz, CDCl$_3$): δ=14.0 (C$_{18}$), 28.4 (C$_{10}$), 28.5 (C$_7$), 30.6 (C$_{11}$), 35.5 (C$_{13}$), 40.2 (C$_6$), 43.2 (C$_{14}$), 60.6 (C$_{17}$), 124.1 (C$_{11a}$ or C$_{12a}$), 125.5 (C$_1$), 127.5 (C$_2$), 127.6 (C$_4$), 129.2 (C$_8$), 130.3 (C$_{11a}$ or C$_{12a}$), 133.2 (C$_9$), 135.4 (C$_3$), 141.0 (C$_{4a}$ or C$_{12}$), 147.5 (C$_{4a}$ or C$_{12}$), 159.9 (C$_{5a}$), 171.3 (C$_{15}$).

MS (ESI+): m/z (%): 376.33 (100) [M+H]$^+$, 378.20 (67), 380.27 (15).

EXAMPLE 44

3-Chloro-9-(4-{4-[(6,7-dimethoxy-1-phenyl-3,4-dihydroisoquinolin-2(1H)-yl)methyl]-1H-1,2,3-triazol-1-yl}butyl)-6,7,10,11-tetrahydro-7,11-methanocycloocta[b]quinolin-12-amine Ditrifluoroacetic Acid (HUP32-PIQ1)

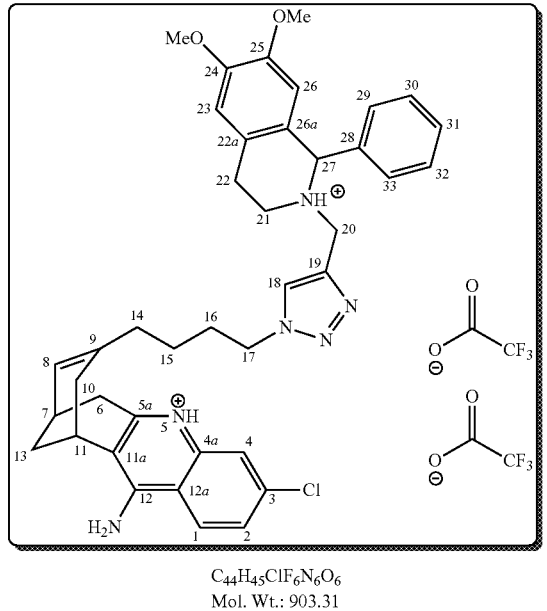

C$_{44}$H$_{45}$ClF$_6$N$_6$O$_6$
Mol. Wt.: 903.31

A mixture of azide (HUP 32) (6.2 mg, 16.3 µmol), 2-Prop-2-yn-1-yl-6,7-dimethoxy-1-phenyl-1,2,3,4-tetrahydroisoquinoline (PIQ 1) (5.1 mg, 16.3 µmol) and copper iodide (2.5 mg, 13.0 µmol) in MeCN (0.5 mL) was stirred at r.t. with light protection for 10 days. The reaction mixture was concentrated to dryness then purified by preparative HPLC (system B) to afford the desired Huprine (HUP32-PIQ1) as a white solid (10.9 mg, 74%).

$^1$H NMR (300 MHz, MeOD): δ=1.25-1.33 (m, 2H, H$_{15}$), 1.59-1.75 (m, 2H, H$_{16}$), 1.93-2.10 (m, 5H, H$_{14}$, H$_{14}$, H$_{10}$, H$_{13}$, H$_{10}$), 2.49 (dd, J=17.7 Hz, J=3.9 Hz, 1H, H$_{13}$), 2.78-2.81 (m,

1H, H$_7$), 2.86 (d, J=19.7 Hz, 1H, H$_6$), 3.20 (dd, J=17.7 Hz, J=5.5 Hz, 1H, H$_6$), 3.20-3.45 (m, 3H, H$_{22}$, H$_{22}$, H$_{11}$), 3.53-3.70 (m, 4H, H$_{20}$, H$_{20}$, H$_{21}$, H$_{21}$), 3.61 (s, 3H, OMe), 3.87 (s, 3H, OMe), 4.26-4.33 (m, 2H, H$_{17}$), 5.61 (d, J=4.3 Hz, 1H, H$_8$), 5.85 (s, 1H, H$_{27}$), 6.36 (s, 1H, H$_{26}$), 6.92 (s, 1H, H$_{23}$), 7.37-7.40 (m, 2H, H$_{29}$, H$_{33}$), 7.49-7.52 (m, 3H, H$_{30}$, H$_{31}$, H$_{32}$), 7.57 (dd, J=9.0 Hz, J=1.7 Hz, 1H, H$_2$), 7.73 (d, J=1.7 Hz, 1H, H$_4$), 8.09 (s, 1H, H$_{18}$), 8.34 (d, J=9.0 Hz, 1H, H$_1$).

$^{13}$C NMR (75 MHz, MeOD): δ=25.1 (C$_{15}$), 27.5 (C$_{11}$), 28.1 (C$_7$), 29.3 (C$_{10}$), 30.4 (C$_{16}$), 30.7 (C$_{22}$), 33.8 (C$_{13}$), 35.9 (C$_6$), 37.2 (C$_{14}$), 48.5 (C$_{21}$), 51.2 (C$_{17}$), 52.3 (C$_{20}$), 56.4 (MeO), 56.5 (MeO), 67.2 (C$_{27}$), 112.3 (2C, C$_{23}$, C$_{26}$), 115.3 (C$_{11a}$ or C$_{12a}$), 115.4 (C$_{11a}$ or C$_{12a}$), 119.3 (C$_4$), 123.3 (C$_{26a}$), 124.0 (C$_{22a}$), 124.8 (C$_{18}$), 125.5 (C$_8$), 126.3 (C$_1$), 127.7 (C$_2$), 130.5 (3C, C$_{30}$, C$_{31}$, C$_{32}$), 131.4 (2C, C$_{29}$, C$_{33}$), 131.1 (C$_{28}$), 138.0 (C$_3$), 139.5 (C$_9$), 140.4 (C$_{4a}$ or C$_{12}$), 150.1 (C$_{4a}$ or C$_{12}$), 151.2 (2C, C$_{24}$, C$_{25}$), 153.0 (C$_{19}$), 156.7 (C$_{5a}$).

MS (ESI+): m/z (%): 675.40 (100) [M+H]$^+$, 338.27 (85) [M/2+H]$^{2+}$, 677.33 (65).

IC$_{50}$ rh-AChE: 3.31±0.2 nM.
IC$_{50}$ rh-BuChE: 20.6±0.2 nM.

EXAMPLE 45

3-Chloro-9-(4-{4-[2-(6,7-dimethoxy-1-phenyl-3,4-dihydroisoquinolin-2(1H)-yl)ethyl]-1H-1,2,3-triazol-1-yl}butyl)-6,7,10,11-tetrahydro-7,11-methanocycloocta[b]quinolin-12-amine Ditrifluoroacetic Acid (HUP32-PIQ2)

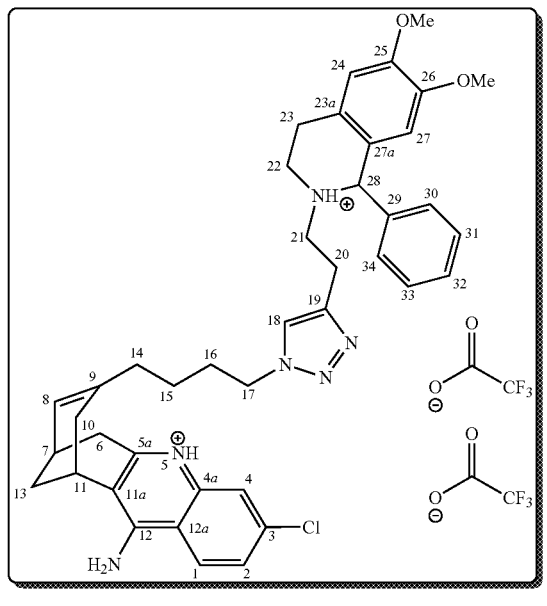

C$_{45}$H$_{47}$ClF$_6$N$_6$O$_6$
Mol. Wt.: 917.33

A mixture of azide (HUP 32) (19.0 mg, 51.6 μmol), 2-But-3-yn-1-yl-6,7-dimethoxy-1-phenyl-1,2,3,4-tetrahydroisoquinoline (PIQ 2) (20.1 mg, 62.5 μmol) and copper iodide (2.0 mg, 10.5 μmol) in MeCN (1 mL) was stirred at r.t. with light protection for 24 h. The reaction mixture was concentrated to dryness then purified by preparative HPLC (system B) to afford the desired Huprine (HUP32-PIQ2) as a light yellow solid (31.1 mg, 66%).

$^1$H NMR (300 MHz, MeOD): δ=1.25-1.35 (m, 2H, H$_{15}$), 1.59-1.73 (m, 2H, H$_{16}$), 1.91-2.10 (m, 5H, H$_{14}$, H$_{14}$, H$_{10}$, H$_{13}$, H$_{10}$), 2.48 (dd, J=17.1 Hz, J=3.4 Hz, 1H, H$_{13}$), 2.78-2.81 (m, 1H, H$_7$), 2.87 (d, J=18.1 Hz, 1H, H$_6$), 3.21 (dd, J=17.9 Hz, J=5.5 Hz, 1H, H$_6$), 3.23-3.36 (m, 6H, H$_{20}$, H$_{21}$, H$_{22}$), 3.37-3.40 (m, 1H, H$_{11}$), 3.50-3.68 (m, 2H, H$_{22}$), 3.62 (s, 3H, OMe), 3.87 (s, 3H, OMe), 4.21 (t, J=6.8 Hz, 2H, H$_{17}$), 5.58 (d, J=4.7 Hz, 1H, H$_8$), 5.87 (s, 1H, H$_{28}$), 6.39 (s, 1H, H$_{27}$), 6.93 (s, 1H, H$_{24}$), 7.35-7.39 (m, 2H, H$_{30}$, H$_{34}$), 7.46-7.51 (m, 3H, H$_{31}$, H$_{32}$, H$_{33}$), 7.56 (dd, J=9.0 Hz, J=1.9 Hz, 1H, H$_2$), 7.73 (d, J=1.9 Hz, 1H, H$_4$), 7.78 (s, 1H, H$_{18}$), 8.34 (d, J=9.0 Hz, 1H, H$_1$).

$^{13}$C NMR (75 MHz, MeOD): δ=21.6 (C$_{20}$), 24.2 (C$_{23}$), 25.0 (C$_{15}$), 27.5 (C$_{11}$), 28.1 (C$_7$), 29.3 (C$_{10}$), 30.4 (C$_{16}$), 33.9 (C$_{13}$), 35.9 (C$_6$), 37.2 (C$_{14}$), 45.9 (C$_{22}$), 51.0 (C$_{17}$), 53.5 (C$_{21}$), 56.4 (MeO), 56.5 (MeO), 67.5 (C$_{28}$), 112.3 (2C, C$_{24}$, C$_{27}$), 115.3 (C$_{11a}$ or C$_{12a}$), 115.4 (C$_{11a}$ or C$_{12a}$), 119.2 (C$_4$), 122.9 (C$_{27a}$), 124.2 (C$_{23a}$), 124.7 (C$_{18}$), 125.4 (C$_8$), 126.3 (C$_1$), 127.7 (C$_2$), 130.4 (3C, C$_{31}$, C$_{32}$, C$_{33}$), 131.4 (2C, C$_{30}$, C$_{34}$), 131.9 (C$_{29}$), 138.0 (C$_3$), 139.5 (C$_9$), 140.4 (C$_{4a}$ or C$_{12}$), 150.1 (C$_{4a}$ or C$_{12}$), 151.2 (2C, C$_{25}$, C$_{26}$), 153.0 (C$_{19}$), 156.7 (C$_{5a}$).

MS (ESI+): m/z (%): 689.27 (100) [M+H]$^+$, 345.13 (37) [M/2+H]$^{2+}$.

IC$_{50}$ rh-AChE: 0.64±0.4 nM.
IC$_{50}$ rh-BuChE: 14.1±0.1 nM.

EXAMPLE 46

3-Chloro-9-(4-{4-[3-(6,7-dimethoxy-1-phenyl-3,4-dihydroisoquinolin-2(1H)-yl)propyl]-1H-1,2,3-triazol-1-yl}butyl)-6,7,10,11-tetrahydro-7,11-methanocycloocta[b]quinolin-12-amine Ditrifluoroacetic Acid (HUP32-PIQ3)

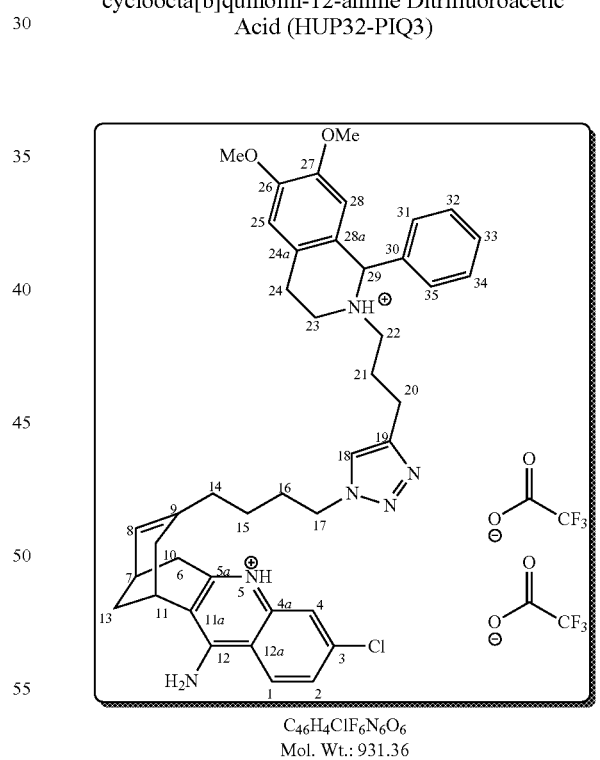

C$_{46}$H$_4$ClF$_6$N$_6$O$_6$
Mol. Wt.: 931.36

A mixture of azide (HUP 32) (19.0 mg, 51.6 μmol), 2-Pent-4-yn-1-yl-6,7-dimethoxy-1-phenyl-1,2,3,4-tetrahydroisoquinoline (PIQ 3) (20.1 mg, 60.0 μmol) and copper iodide (2.0 mg, 10.5 μmol) in MeCN (1 mL) was stirred at r.t. with light protection for 24 h. The reaction mixture was concentrated to dryness then purified by preparative HPLC (system B) to afford the desired Huprine (HUP32-PIQ3) as a white solid (35.3 mg, 74%).

$^1$H NMR (300 MHz, MeOD): δ=1.25-1.36 (m, 2H, H$_{15}$), 1.57-1.74 (m, 2H, H$_{16}$), 1.90-2.10 (m, 5H, H$_{14}$, H$_{14'}$, H$_{10}$, H$_{13}$, H$_{10'}$), 2.10-2.30 (m, 2H, H$_{21}$), 2.49 (dd, J=18.0 Hz, J=4.1 Hz, 1H, H$_{13'}$), 2.68-2.78 (m, 2H, H$_{20}$), 2.78-2.82 (m, 1H, H$_7$), 2.87 (d, J=18.0 Hz, 1H, H$_6$), 3.21 (dd, J=17.9 Hz, J=5.3 Hz, 1H, H$_{6'}$), 3.18-3.35 (m, 4H, H$_{22}$, H$_{24}$), 3.38-3.41 (m, 1H, H$_{11}$), 3.50-3.68 (m, 2H, H$_{23}$), 3.59 (s, 3H, OMe), 3.85 (s, 3H, OMe), 4.20 (t, J=7.0 Hz, 2H, H$_{17}$), 5.59 (d, J=4.9 Hz, 1H, H$_8$), 5.74 (s, 1H, H$_{29}$), 6.31 (s, 1H, H$_{28}$), 6.90 (s, 1H, H$_{25}$), 7.29-7.33 (m, 2H, H$_{31}$, H$_{35}$), 7.43-7.47 (m, 3H, H$_{32}$, H$_{33}$, H$_{34}$), 7.56 (dd, J=9.0 Hz, J=1.9 Hz, 1H, H$_2$), 7.71 (s, 1H, H$_{18}$), 7.73 (d, J=1.9 Hz, 1H, H$_4$), 8.34 (d, J=9.0 Hz, 1H, H$_1$).

$^{13}$C NMR (75 MHz, MeOD): δ=23.3 (C$_{20}$), 24.2 (C$_{24}$), 24.7 (C$_{21}$), 25.1 (C$_{15}$), 27.5 (C$_{11}$), 28.1 (C$_7$), 29.3 (C$_{10}$), 30.4 (C$_{16}$), 33.9 (C$_{13}$), 35.9 (C$_6$), 37.2 (C$_{14}$), 46.1 (C$_{23}$), 51.0 (C$_{17}$), 53.6 (C$_{22}$), 56.3 (MeO), 56.4 (MeO), 67.9 (C$_{29}$), 112.3 (C$_{25}$), 112.4 (C$_{28}$), 115.3 (C$_{11a}$ or C$_{12a}$), 115.4 (C$_{11a}$ or C$_{12a}$), 119.2 (C$_4$), 123.1 (C$_{28a}$), 124.7 (C$_{24a}$), 124.8 (C$_{18}$), 125.4 (C$_8$), 126.3 (C$_1$), 127.7 (C$_2$), 130.4 (3C, C$_{32}$, C$_{33}$, C$_{34}$), 131.3 (2C, C$_{31}$, C$_{35}$), 131.6 (C$_{30}$), 138.0 (C$_3$), 139.5 (C$_9$), 140.4 (C$_{4a}$ or C$_{12}$), 150.0 (C$_{4a}$ or C$_{12}$), 151.1 (2C, C$_{26}$, C$_{27}$), 153.0 (C$_{19}$), 156.7 (C$_{5a}$).

MS (ESI+): m/z (%): 352.40 (100) [M/2+H]$^{2+}$, 703.27 (28) [M+H]$^+$.

IC$_{50}$ rh-AChE: 0.61±0.1 nM.
IC$_{50}$ rh-BuChE: 11.4±0.6 nM.

EXAMPLE 47

3-Chloro-9-(4-{4-[4-(6,7-dimethoxy-1-phenyl-3,4-dihydroisoquinolin-2(1H)-yl)butyl]-1H-1,2,3-triazol-1-yl}butyl)-6,7,10,11-tetrahydro-7,11-methanocycloocta[b]quinolin-12-amine Ditrifluoroacetic Acid (HUP32-PIQ4)

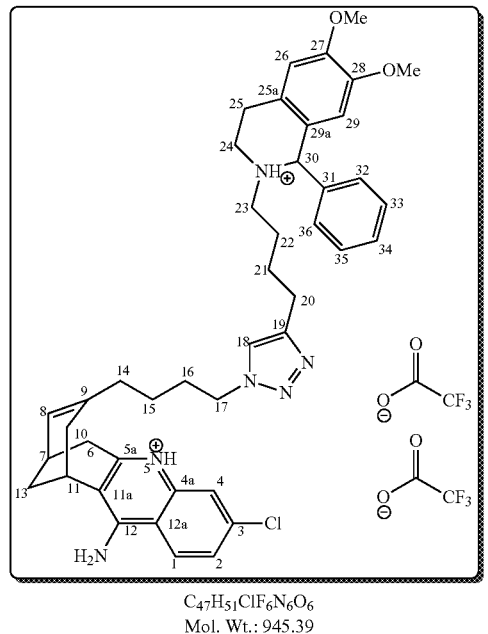

C$_{47}$H$_{51}$ClF$_6$N$_6$O$_6$
Mol. Wt.: 945.39

A mixture of azide (HUP 32) (30.6 mg, 58.0 µmol), 2-Hex-5-yn-1-yl-6,7-dimethoxy-1-phenyl-1,2,3,4-tetrahydroisoquinoline (PIQ 4) (24.8 mg, 72.0 µmol) and copper iodide (3.6 mg, 19.0 µmol) in MeCN (1.2 mL) and MeOH (0.3 mL) was stirred at r.t. with light protection for 16 h. The reaction mixture was concentrated to dryness then purified by preparative HPLC (system B) to afford the desired Huprine (HUP32-PIQ4) as a white solid (21.5 mg, 32%).

$^1$H NMR (300 MHz, MeOD): δ=1.28-1.35 (m, 4H, H$_{15}$, H$_{22}$), 1.60-1.70 (m, 4H, H$_{16}$, H$_{21}$), 1.84-2.00 (m, 5H, H$_{14}$, H$_{14'}$, H$_{10}$, H$_{25}$, H$_{25'}$), 2.00-2.10 (m, 2H, H$_{13}$, H$_{10'}$), 2.48 (dd, J=17.5 Hz, J=3.9 Hz, 1H, H$_{13'}$), 2.65-2.75 (m, 2H, H$_{20}$), 2.78-2.82 (m, 1H, H$_7$), 2.87 (d, J=17.7 Hz, 1H, H$_6$), 3.21 (dd, J=17.7 Hz, J=5.5 Hz, 1H, H$_{6'}$), 3.18-3.31 (m, 4H, H$_{23}$, H$_{25}$), 3.38-3.41 (m, 1H, H$_{11}$), 3.45-3.65 (m, 2H, H$_{24}$), 3.60 (s, 3H, OMe), 3.86 (s, 3H, OMe), 4.20 (t, J=6.8 Hz, 2H, H$_{17}$), 5.59 (d, J=5.1 Hz, 1H, H$_8$), 5.74 (s, 1H, H$_{30}$), 6.33 (s, 1H, H$_{29}$), 6.91 (s, 1H, H$_{26}$), 7.32-7.36 (m, 2H, H$_{32}$, H$_{36}$), 7.47-7.50 (m, 3H, H$_{33}$, H$_{34}$, H$_{35}$), 7.57 (dd, J=9.0 Hz, J=1.9 Hz, 1H, H$_2$), 7.71 (s, 1H, H$_{18}$), 7.72 (d, J=1.9 Hz, 1H, H$_4$), 8.34 (d, J=9.0 Hz, 1H, H$_1$).

$^{13}$C NMR (75 MHz, MeOD): δ=24.7 (C$_{25}$), 25.1 (C$_{15}$), 25.5 (C$_{20}$), 27.3 (C$_{21}$), 27.5 (C$_{11}$), 28.1 (C$_7$), 29.3 (C$_{10}$), 30.4 (C$_{16}$), 22.8 (C$_{22}$), 33.8 (C$_{13}$), 35.9 (C$_6$), 37.2 (C$_{14}$), 49.1 (C$_{24}$), 51.0 (C$_{17}$), 54.0 (C$_{23}$), 56.4 (MeO), 56.5 (MeO), 67.9 (C$_{30}$), 112.3 (2C, C$_{25}$, C$_{28}$), 115.3 (C$_{11a}$ or C$_{12a}$), 115.4 (C$_{11a}$ or C$_{12a}$), 119.2 (C$_4$), 129. (C$_{29a}$), 124.8 (C$_{25a}$), 124.9 (C$_{18}$), 125.5 (C$_8$), 126.3 (C$_1$), 127.7 (C$_2$), 130.4 (3C, C$_{33}$, C$_{34}$, C$_{35}$), 131.3 (2C, C$_{32}$, C$_{36}$), 131.6 (C$_{31}$), 138.0 (C$_3$), 139.5 (C$_9$), 140.4 (C$_{4a}$ or C$_{12}$), 150.0 (C$_{4a}$ or C$_{12}$), 151.1 (2C, C$_{27}$, C$_{28}$), 153.0 (C$_{19}$), 156.7 (C$_{5a}$).

MS (ESI+): m/z (%): 359.33 (100) [M/2+H]$^{2+}$, 717.40 (28) [M+H]$^+$.

IC$_{50}$ rh-AChE: 0.78±0.1 nM.
IC$_{50}$ rh-BuChE: 9.5±0.6 nM.

EXAMPLE 48

4-{4-[4-(7-(dimethylamino)-2-oxo-2H-chromen-4-yl)butyl]-1H-1,2,3-triazol-1-yl}prop-2-yn-1-yl)-6,7,10,11-tetrahydro-7,11-methanocyclo octa[b]quinolin-12-amine Ditrifluoroacetic Acid (HUP32-COU1)

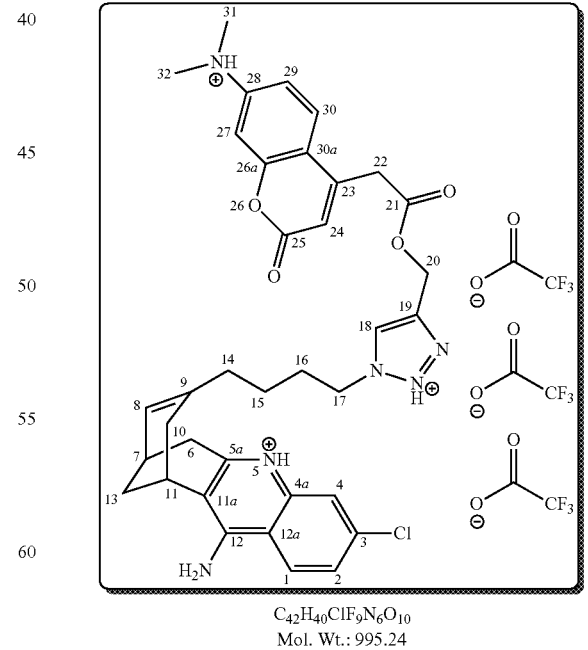

C$_{42}$H$_{40}$ClF$_9$N$_6$O$_{10}$
Mol. Wt.: 995.24

A mixture of azide (HUP32) (21.4 mg, 58 µmol), Prop-2-yn-1-yl[7-(dimethylamino)-2-oxo-2H-chromen-4-yl]acetate (COU1) (free base, 20.0 mg, 70 μmol) and copper iodide (4.4 mg, 23 μmol) in acetonitrile (1 mL) was stirred at r.t. with light protection for 24 h. The reaction mixture was concentrated to dryness then purified by preparative HPLC (system A) to afford the desired huprine (HUP32-COU1) as fluorescent yellow solid (42.7 mg, 64%).

$^1$H NMR (300 MHz, MeOD): δ=1.15-1.34 (m, 2H, $H_{15}$), 1.52-1.68 (m, 2H, $H_{16}$), 1.86-2.0 (m, 5H, $H_{14}$, $H_{14}$, $H_{10}$, $H_{13}$, $H_{10}$), 2.42 (dd, J=17.2 Hz, J=3.6 Hz, 1H, $H_{13}$), 2.78-2.82 (m, 1H, $H_7$), 2.85 (d, J=18.0 Hz, 1H, $H_6$), 3.03 (s, 6H, $H_{31}$, $H_{32}$), 3.19 (dd, J=17.9 Hz, J=5.1 Hz, 1H, $H_6$), 3.33 (m, 1H, $H_{11}$), 3.81 (s, 2H, $H_{22}$), 4.22 (t, J=6.8 Hz, 2H, $H_{17}$), 5.22 (s, 2H, $H_{20}$), 5.55 (d, J=4.7 Hz, 1H, $H_8$), 5.97 (s, 1H, $H_{24}$), 6.46 (d, J=2.5 Hz, 1H, $H_{27}$), 6.61 (dd, J=9.0 Hz, J=2.5 Hz, 1H, $H_{29}$), 7.36 (d, J=9.0 Hz, 1H, $H_{30}$), 7.54 (dd, J=9.0 Hz, J=1.9 Hz, 1H, $H_2$), 7.68 (d, J=1.9 Hz, 1H, $H_4$), 7.81 (s, 1H, $H_{18}$), 8.31 (d, J=9.0 Hz, 1H, $H_1$).

$^{13}$C NMR (75 MHz, MeOD): δ=25.0 ($C_{15}$), 27.5 ($C_{11}$), 28.1 ($C_7$), 29.3 ($C_{10}$), 30.2 ($C_{16}$), 33.8 ($C_{13}$), 35.9 ($C_6$), 37.1 ($C_{14}$), 38.3 ($C_{22}$), 40.2 (2C, $C_{30}$, $C_{31}$), 50.9 ($C_{17}$), 59.0 ($C_{20}$), 98.7 ($C_{27}$), 109.5 ($C_{12a}$), 110.5 (2C, $C_{24}$, $C_{29}$), 115.2 ($C_{11a}$ or $C_{30a}$), 115.3 ($C_{11a}$ or $C_{30a}$), 119.2 ($C_4$), 125.5 ($C_8$), 125.9 ($C_{26a}$ or $C_{12}$ or $C_{19}$), 126.3 ($C_1$), 126.8 ($C_{30}$), 127.7 ($C_2$), 134.0 ($C_3$), 139.4 ($C_9$), 140.4 ($C_{4a}$), 151.4 ($C_{13}$), 153.0 ($C_{28}$), 154.7 ($C_{26a}$ or $C_{12}$ or $C_{19}$), 157.0 ($C_{26a}$ or $C_{19}$), 157.1 ($C_{5a}$), 164.0 ($C_{25}$), 170.6 ($C_{21}$).

MS (ESI+): m/z (%): 655.27 (32), 653.27 (100) [M+H]$^+$
HPLC: tr=21.4 (purity>95%).

EXAMPLE 49

Preparation of HUP32-COU2

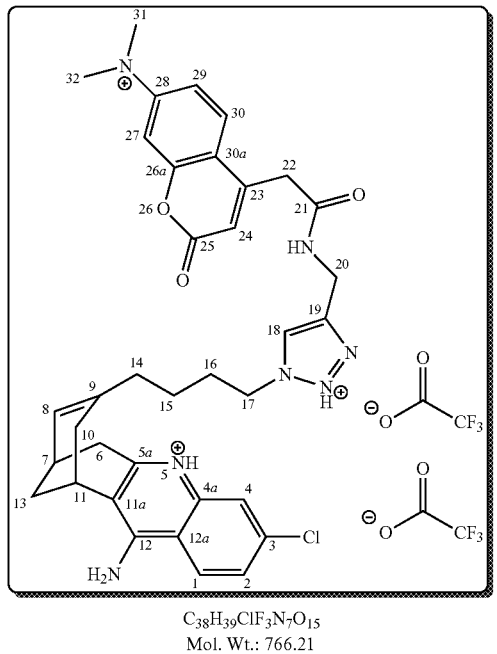

$C_{38}H_{39}ClF_3N_7O_{15}$
Mol. Wt.: 766.21

A mixture of azide (HUP32) (15.0 mg, 40.8 μmol), Prop-2-yn-1-yl [7-(dimethylamino)-2-oxo-2H-chromen-4-yl]amide (COU2) (free base, 14.0 mg, 49.0 μmol) and copper iodide (1.9 mg, 10 μmol) in acetonitrile (0.5 mL) was stirred at r.t. with light protection for 48 h. The reaction mixture was concentrated to dryness then purified by preparative HPLC (system A) to afford the desired Huprine (HUP32-COU2) as fluorescent yellow solid (9.6 mg, 31%).

$^1$H NMR (300 MHz, MeOD): δ=1.16-1.37 (m, 2H, $H_{15}$), 1.53-1.65 (m, 2H, $H_{16}$), 1.85-2.01 (m, 4H, $H_{14}$, $H_{14}$, $H_{10}$, $H_{10}$), 2.01-2.07 (m, 1H, $H_{13}$), 2.34 (dd, J=17.2 Hz, J=3.6 Hz, 1H, $H_{13}$), 2.78-2.82 (m, 1H, $H_7$), 2.85 (d, J=18.0 Hz, 1H, $H_6$), 3.07 (s, 6H, $H_{31}$, $H_{32}$), 3.17 (dd, J=17.9 Hz, J=5.1 Hz, 1H, $H_6$), 3.31 (m, 1H, $H_{11}$), 3.72 (s, 2H, $H_{22}$), 4.19 (t, J=6.8 Hz, 2H, $H_{17}$), 4.26 (s, 2H, $H_{20}$), 5.53 (d, J=4.7 Hz, 1H, $H_8$), 6.01 (s, 1H, $H_{24}$), 6.49 (d, J=2.5 Hz, 1H, $H_{27}$), 6.67 (dd, J=9.0 Hz, J=2.5 Hz, 1H, $H_{29}$), 7.48 (d, J=9.0 Hz, 1H, $H_{30}$), 7.55 (dd, J=9.0 Hz, J=1.9 Hz, 1H, $H_2$), 7.62 (s, 1H, $H_{18}$), 7.68 (d, J=1.9 Hz, 1H, $H_4$), 8.31 (d, J=9.0 Hz, 1H, $H_1$).

$^{13}$C NMR (75 MHz, MeOD): δ=24.8 ($C_{15}$), 27.4 ($C_{11}$), 28.1 ($C_7$), 29.3 ($C_{10}$), 30.1 ($C_{16}$), 33.6 ($C_{13}$), 35.9 ($C_6$), 37.1 ($C_{14}$), 39.9 ($C_{22}$), 40.2 (2C, $C_{31}$, $C_{32}$), 50.8 ($C_{17}$), 59.8 ($C_{20}$), 98.7 ($C_{27}$), 109.7 ($C_{12a}$), 110.4 (2C, $C_{24}$, $C_{29}$), 115.2 ($C_{11a}$ or $C_{30a}$), 115.3 ($C_{11a}$ or $C_{30a}$), 119.2 ($C_4$), 123.9 ($C_{26a}$ or $C_{12}$ or $C_{19}$), 125.5 ($C_8$), 126.3 ($C_1$), 126.9 ($C_{30}$), 127.7 ($C_2$), 137.9 ($C_3$), 139.4 ($C_9$), 140.4 ($C_{4a}$), 152.7 ($C_{13}$ or $C_{28}$), 152.9 ($C_{13}$ or $C_{28}$), 154.7 ($C_{26a}$ or $C_{12}$ or $C_{19}$), 156.7 ($C_{26a}$ or $C_{12}$ or $C_{19}$), 157.1 ($C_{5a}$), 164.1 ($C_{25}$), 171.2 ($C_{21}$).

MS (ESI+): m/z (%): 652.33 (100) [M+H]$^+$.

EXAMPLE 50

Preparation of HUP32-IND1

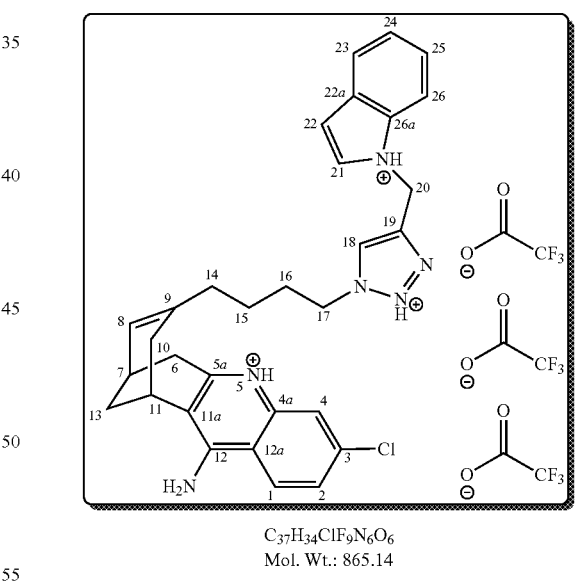

$C_{37}H_{34}ClF_9N_6O_6$
Mol. Wt.: 865.14

A mixture of azide (HUP32) (21.4 mg, 58.2 μmol), 1-(Prop-2-ynyl)-1H-indole(IND1) (15.5 mg, 100 μmol) and copper iodide (6.0 mg, 31 μmol) in acetonitrile (1 mL) was stirred at r.t. with light protection for 24 h. The reaction mixture was concentrated to dryness then purified by preparative HPLC (system A) to afford the desired huprine (HUP32-IND1) as a light red solid (30.7 mg, 61%).

MS (ESI+): m/z (%): 262.13 (28) [M/2+H]$^{2+}$, 523.24 (100) [M+H]$^+$.

HPLC: tr=23.5 (purity >95%).

EXAMPLE 51

Preparation of HUP32-IND2

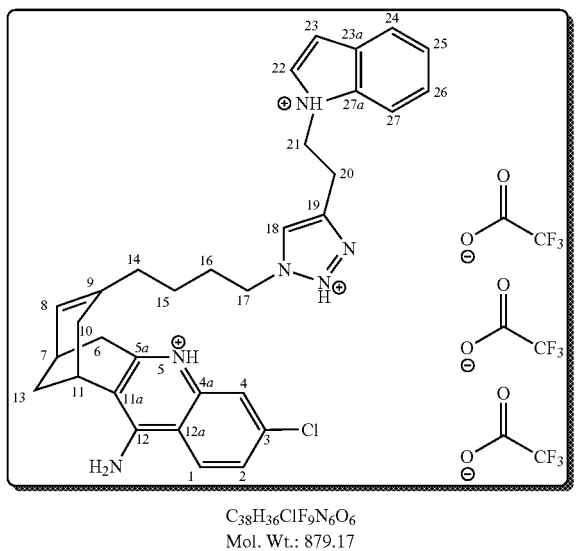

C38H36ClF9N6O6
Mol. Wt.: 879.17

A mixture of azide (HUP32) (21.4 mg, 58.2 μmol), 1-(But-3-ynyl)-1H-indole (IND2) (16.9 mg, 100 μmol) and copper iodide (6.0 mg, 31 μmol) in actetonitrile (1 mL) was stirred at r.t. with light protection for 24 h. The reaction mixture was concentrated to dryness then purified by preparative HPLC (system A) to afford the desired huprine (HUP32-IND2) as a light red solid (4.3 mg, 5%).

MS (ESI+): m/z (%): 269.40 (100) [M/2+H]$^{2+}$, 539.26 (24) [M+H]$^+$.

HPLC: tr=23.8 (purity 86%).

EXAMPLE 52

Preparation of HUP32-TPI1

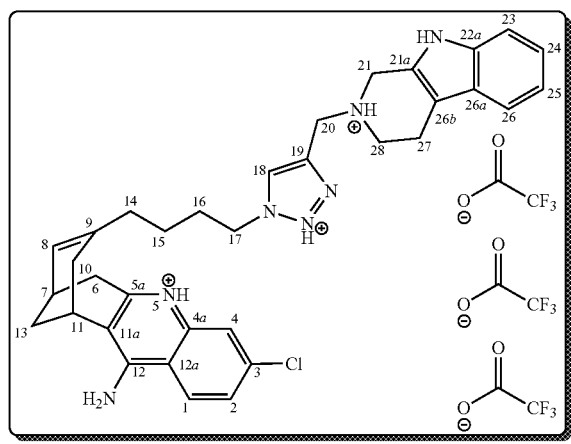

C40H39ClF9N7O6
Mol. Wt.: 920.22

A mixture of azide (HUP32) (21.4 mg, 58.2 μmol), 2,3,4,9-Tetrahydro-2-(prop-2-ynyl)-1H-pyrido[3,4-b]indole (TPI1) (21.0 mg, 100 μmol) and copper iodide (6.0 mg, 31 μmol) in actetonitrile (1 mL) was stirred at r.t. with light protection for 24 h. The reaction mixture was concentrated to dryness then purified by preparative HPLC (system A) to afford the desired huprine (HUP32-TPI1) as a white solid (34.2 mg, 64%).

MS (ESI+): m/z (%): 289.60 (100) [M/2+H]$^{2+}$, 578.29 (28) [M+H]$^+$.

HPLC: tr=18.5 (purity >95%).

EXAMPLE 53

Effect of HUP-COUA1 on Amyloid-Bata Peptide

HUP32-COU1 effect on amyloid-beta peptide aggregation is drastic, all the more in the presence of AChE. The measuring of thioflavin T fluorescence allowed monitoring amyloid-beta peptide aggregation over time, at various concentrations of HUP32-COU1 (330 pM to 67 nM), with or without AChE (experiments performed at 25 μM Aβ±1 μM AChE). Thioflavin T fluorescence reveals not only the formation of fibrils, but also that of other beta-sheets pleated, amyloid-beta peptide oligomers. The results show that HUP32-COU1 interacts with amyloid-beta peptide even in the absence of AChE, reducing amyloid-species formation; this is evidenced by a concentration-dependant increase in the lag-time before the onset of ThT fluorescence. The results moreover suggest that HUP32-COU1 is able to breakdown amyloid-species, as evidenced by a concentration-dependent decrease in the lag-time before the drop in ThT fluorescence. The concentrations at which these effects are at their half-maxima were estimated to 180 and 50 nM, respectively, in the framework of a first-order inhibition model. In the presence of AChE, amyloid-species formation comparatively appears anecdotical, as suggested by the 10-fold decrease in ThT average fluorescence. The complex formed by AChE and HUP32-COU1 displays an apparent negative-effect on amyloid-species formation, which reaches its half maximum at 8 mM HUP32-COU1.

In summary, our results put forward HUP32-COU1 as a potent inhibitor of amyloid-beta peptide and amyloid-beta peptide+AChE aggregation (into oligomers and/or fibrils) and as an amyloid-beta peptide/fibrils breaker. Moreover, they strongly suggest that the AChE-HUP32-COU1 complex is an inhibitor of amyloid-beta peptide amyloid-species formation.

EXAMPLE 54

Preparation of an Affinity Resin

Coupling Method

The ligand (HUP 24; di-TFA salt; 50 mg; 90 μmoles) was dissolved in H$_2$O/15% MeOH, at pH 5.0 was contacted with ECH-Sepharose 4B resin (GE-Healthcare; 6 ml, 90 μmoles of active sites) with a ratio ligand/active group of 1. The coupling was catalysed with an excess of carbodiimide (0.1 M final). Then, the resin was thoroughly rinced with water buffered with 20 mM Tris, 200 mM NaCl, pH 7.4 and placed in a column.

Purification

The BuChE partially purified (containing albumin) in a buffer 20 mM Tris, 200 mM NaCl, pH 7.4 is passed through the column. The main part of the active BuChE is retained in the column contrary to the main part of the proteic fraction (albumin). Further more stringent washing with 20 mM Tris, 500 mM NaCl, pH 7.4 allow removing the remaining albumin. Elution is completed with a buffer 20 mM Tris pH 7.4, 1M NaCl, Tetramethylammonium 0.5 M, Decamethonium 1 mM. 95% pure BuChE is obtained, with a recovery of >90% of the introduced BuChE (verified by standard Elmann based colorimetric assay).

The invention claimed is:

1. A method for purifying a cholinesterase sample, comprising performing an affinity chromatography step comprising contacting a sample containing a cholinesterase with a support material comprising a compound of formula I:

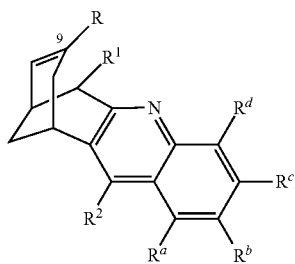

(I)

wherein,
R is a moiety of formula -A-Y-Z,
wherein,
A is $C_1$-$C_4$ alkylene;
Y is a single bond, —O—, —C(O)—, —C(O)O—, —OC(O)—, —OS(O)$_2$—, —NH—, —N($R^4$)— or

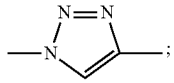

Z is H, halo, cyano, hydroxyl, azide, hydrazinyl, —$OR^5$, —C(O)$OR^6$, —$NR^6R^7$, —$N^+R^6R^7R^8$, —CH(COO$R^6$)$_2$, —CH(CH$_2$OH)$_2$, —CH$_2$—OC(O)—$R^9$, $C_1$-$C_4$ alkyl, $C_1$-$C_4$ alkyl substituted with halogen or hydroxyl, $C_2$-$C_4$ alkenyl or $C_2$-$C_4$ alkenyl substituted with halogen or hydroxyl;
$R^4$ and $R^5$ are $C_1$-$C_4$ alkyl or $C_1$-$C_4$ alkyloxycarbonyl;
$R^6$, $R^7$ and $R^8$ are independently H or $C_1$-$C_4$ alkyl; and
$R^9$ is $C_1$-$C_4$ alkyl or $C_1$-$C_4$ alkyl substituted with halogen;
with the proviso that R is not alkyl;
$R^a$, $R^b$, $R^c$ and $R^d$ are independently H, halogen, cyano, carboxyl, —O($C_1$-$C_4$ alkyl), —S($C_1$-$C_4$ alkyl), or —CH$_2$S($C_1$-$C_4$ alkyl);
$R^1$ is H or =CH$_2$; and
$R^2$ is Cl or $NR^3R^{i3}$ wherein $R^3$ and $R^{i3}$ are independently H, acetyl, $C_1$-$C_4$ alkyl, —CO($C_1$-$C_4$ alkyl);
and pharmaceutically acceptable salts thereof.

2. The method of claim 1, wherein the cholinesterase is chosen from acetylcholinesterase and butyrylcholinesterase.

3. The method of claim 1, wherein R is selected from the group consisting of:
—CH$_2$—COO—C$_2$H$_5$,
—(CH$_2$)$_2$—OH,
—(CH$_2$)$_2$—OCO—CH$_3$,
—(CH$_2$)$_2$—OCO—CF$_3$,
—(CH$_2$)$_2$—O—CH$_3$,
—(CH$_2$)$_2$—I,
—(CH$_2$)$_2$—CN,
—(CH$_2$)$_2$—Cl,
—(CH$_2$)$_2$—F,
—CH$_2$—COOH,
—(CH$_2$)$_2$—N$_3$,
—(CH$_2$)$_2$—OSO$_2$—CH$_3$,
—(CH$_2$)$_2$—NH—NH$_2$,
—(CH$_2$)$_2$—NH—OH,
—(CH$_2$)$_2$—N(boc)-O(boc),
—(CH$_2$)$_2$—OCO—NH$_2$,
—(CH$_2$)$_2$—OCO—CH=CH$_2$,
—CH$_2$—CO—N(CH$_3$)$_2$,
—CH$_2$—CONH$_2$,
—(CH$_2$)$_2$—N$^+$H(CH3)$_2$,
—(CH$_2$)$_2$—(C$_2$H$_2$N$_3$)—COOCH$_3$,
—(CH$_2$)$_2$—(C$_2$H$_2$N3)-CH$_2$OH,
—(CH$_2$)$_2$—N$^+$H$_3$,
—(CH$_2$)$_2$—N$^+$(CH$_3$)$_3$,
—(CH$_2$)$_2$—CH—(COOCH$_3$)$_2$,
—(CH$_2$)$_2$—CH—(COOC$_2$H$_5$)$_2$,
—(CH$_2$)$_2$—CH—(CH$_2$OH)$_2$,
—(CH$_2$)$_3$—COO—CH3,
—(CH$_2$)$_4$—OH,
—(CH$_2$)$_4$—OSO$_2$—CH$_3$,
—(CH$_2$)$_4$—N$_3$,
—(CH$_2$)$_4$—(C$_2$H$_2$N$_3$)—COOCH$_3$,
—(CH$_2$)$_4$—(C$_2$H$_2$N$_3$)—CH$_2$OH,
—(CH$_2$)$_4$—(C$_2$H$_2$N$_3$)—CH$_2$OCOCF$_3$,
—(CH$_2$)$_3$—COO—C$_2$H$_5$.

4. The method according to claim 1, wherein $R^2$ is $NR^3R^{i3}$.

5. The method according to claim 1, wherein $R^a$, $R^b$, $R^d$ and $R^c$ are H or $R^a$, $R^b$ and $R^d$ are H and $R^c$ is Cl.

6. The method according to claim 1, wherein $R^1$ is H.

7. The method according to claim 1, wherein the compound of formula I is selected from the group consisting of:

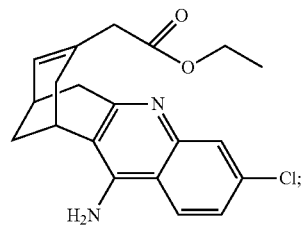

(HUP 1)

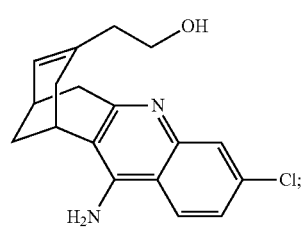

(HUP 2)

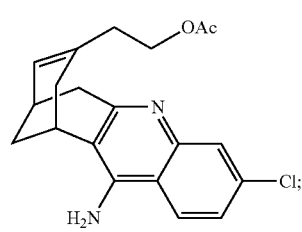

(HUP 4)

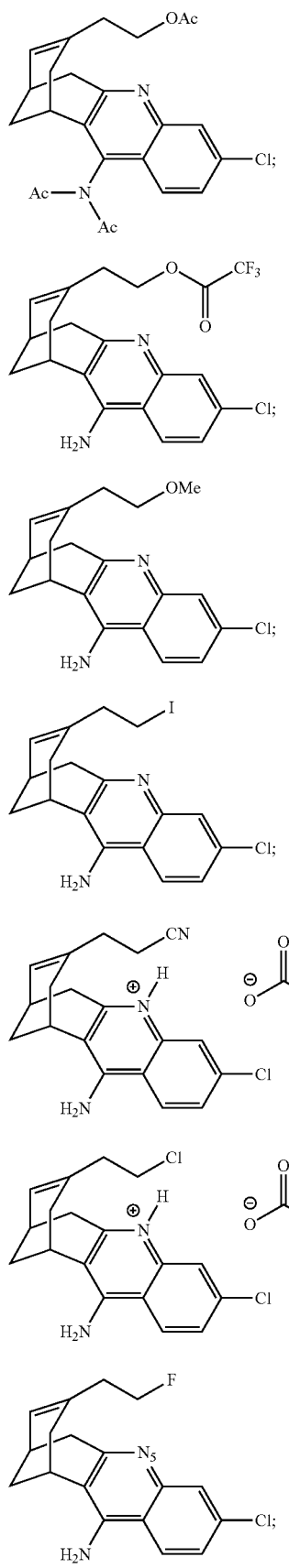
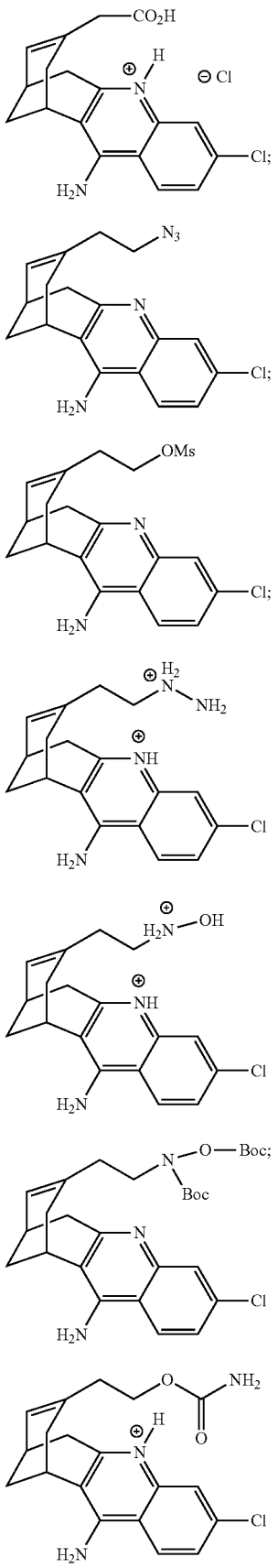

(HUP 18)
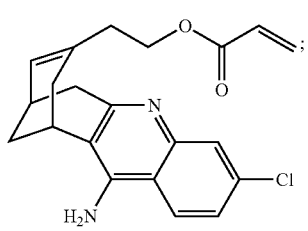
(HUP 19)
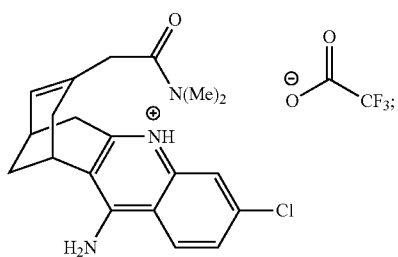
(HUP 20)
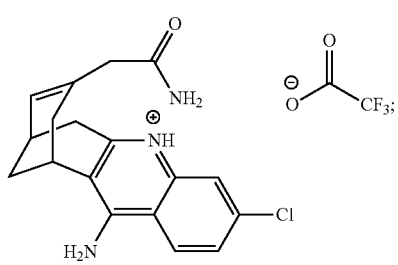
(HUP 21)
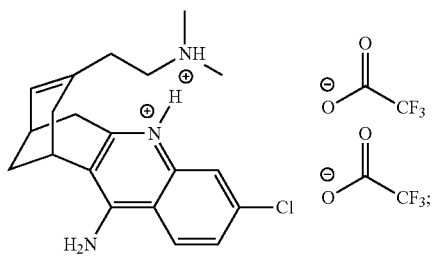
(HUP 22)
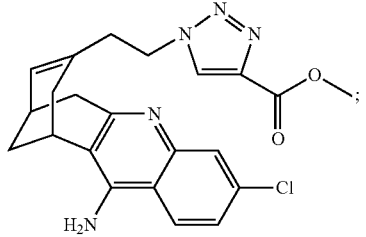
(HUP 23)
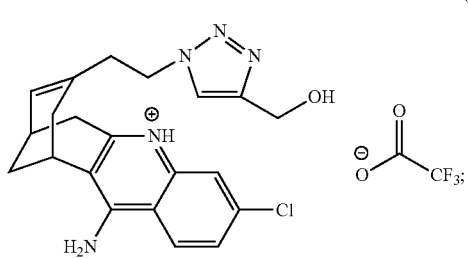
(HUP 24)
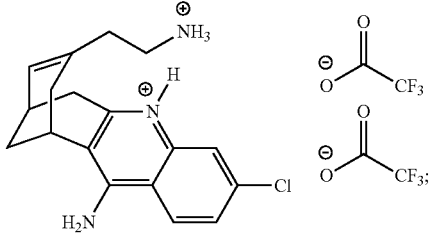
(HUP 25)
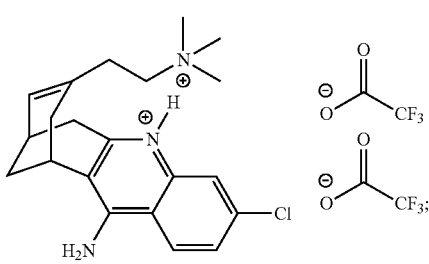
(HUP 26)
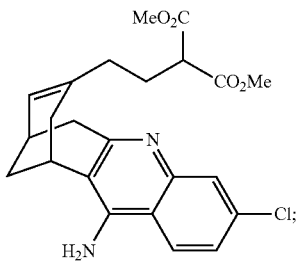
(HUP 27)
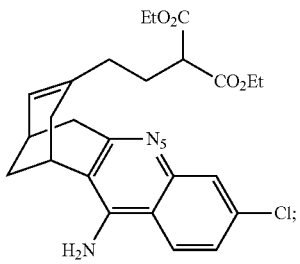
(HUP 28)
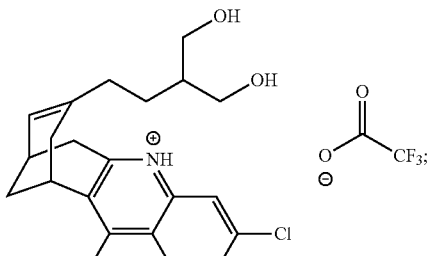
(HUP 29)
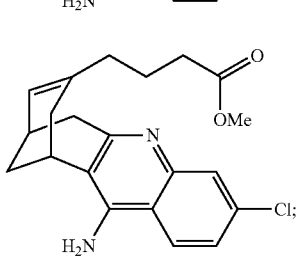

81
-continued
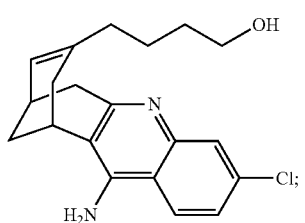
(HUP 30)
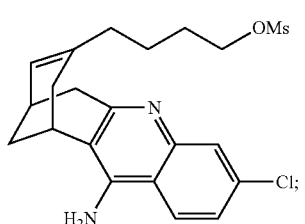
(HUP 31)
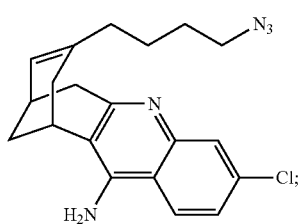
(HUP 32)
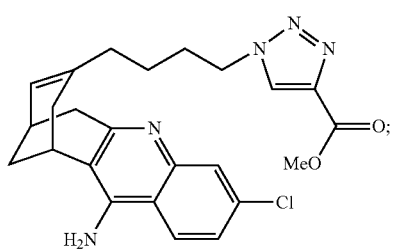
(HUP 33)
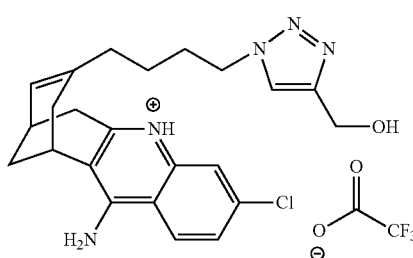
(HUP 34)
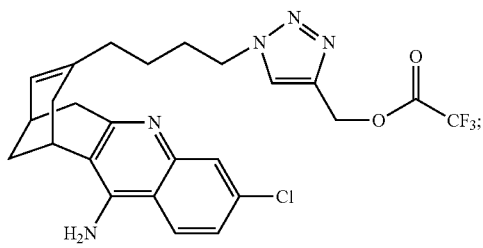
(HUP 35)
82
-continued
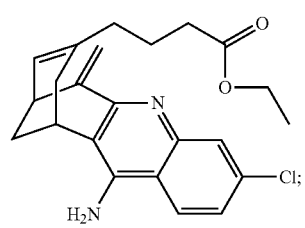
(HUP 36)
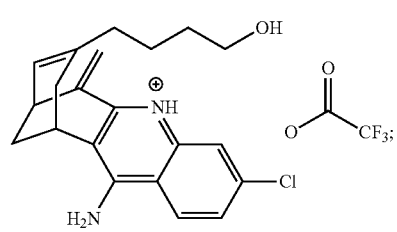
(HUP 37)
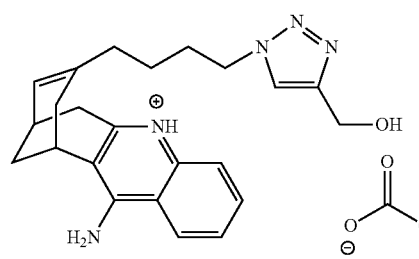
(HUP 38)
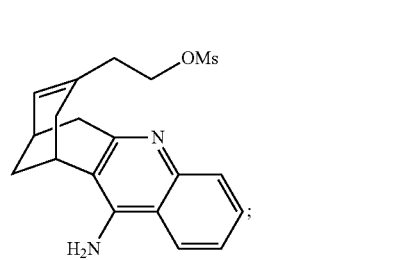
(HUP 39)
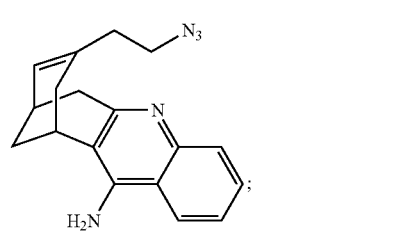
(HUP 40)
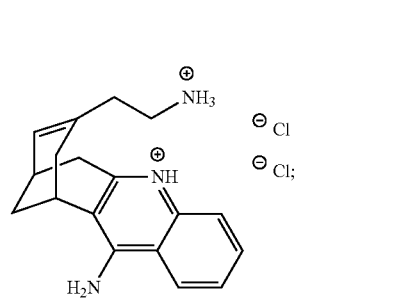
(HUP 41)

-continued

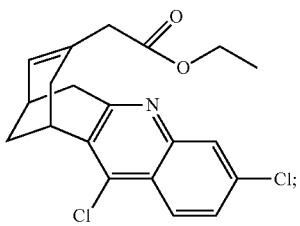

(HUP 42)

and pharmaceutically acceptable salts thereof.

8. The method according to claim 1, wherein the support material is a polymeric support material, and the compound of formula I is fixed on the polymeric support material via a reactive linker in radical R suitable for covalent grafting onto the polymeric support.

9. The method according to claim 8, wherein the polymeric support material is a polymeric resin.

10. The method according to claim 8, wherein the polymeric support material is a sepharose resin.

11. The method according to claim 10, wherein the sepharose resin is ECH-Sepharose 4B resin.

12. The method according to claim 9, wherein the polymeric support material is a sepharose resin.

13. The method according to claim 12, wherein the sepharose resin is ECH-Sepharose 4B resin.

14. The method according to claim 8, wherein the reactive linker in radical R is an amine.

15. The method according to claim 1, wherein,
the support material is a polymeric resin,
the method further comprises the steps of:
coupling the compound of formula I with a polymeric resin,
placing the polymeric resin coupled with the compound of formula I into a column, and
the affinity chromatography step comprises passing a cholinesterase sample through the column of the polymeric resin coupled with the compound of formula I.

16. The method according to claim 15, wherein the step of coupling is performed by mixing the compound of formula I with a polymeric resin in the presence of carbodiimide as a catalyst.

17. The method according to claim 15, further comprising a rinsing step before the step of placing the polymeric resin coupled with the compound of formula I into the column, said rinsing step consisting of rinsing the polymeric resin coupled with the compound of formula I with water buffered with Tris and NaCl at a pH of around 7.4.

18. The method according to claim 15, wherein the cholinesterase sample comprises water buffered with Tris and NaCl at a pH of around 7.4.

19. The method according to claim 18, wherein the affinity chromatography step further comprises, after passing the cholinesterase sample through the column, eluting with a solution comprising Tris, NaCl, tetramethylammonium and decamethonium, at a pH of around 7.4.

* * * * *